US011259874B1

(12) United States Patent
Landon et al.

(10) Patent No.: US 11,259,874 B1
(45) Date of Patent: Mar. 1, 2022

(54) THREE-DIMENSIONAL SELECTIVE BONE MATCHING

(71) Applicant: Smith & Nephew, Inc., Memphis, TN (US)

(72) Inventors: Ryan L. Landon, Olive Branch, MS (US); Daniel Farley, Memphis, TN (US); David Lieberman, Cordova, TN (US); Bilal Ismail, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 64 days.

(21) Appl. No.: 16/789,930

(22) Filed: Feb. 13, 2020

Related U.S. Application Data

(63) Continuation-in-part of application No. 16/387,151, filed on Apr. 17, 2019.
(Continued)

(51) Int. Cl.
*G06T 15/00* (2011.01)
*A61B 34/10* (2016.01)
(Continued)

(52) U.S. Cl.
CPC .......... *A61B 34/10* (2016.02); *A61B 17/1659* (2013.01); *A61F 2/4609* (2013.01); *G06F 30/12* (2020.01); *G06T 7/0012* (2013.01); *G06T 17/00* (2013.01); *G06T 19/20* (2013.01); *G16H 30/40* (2018.01); *G16H 50/50* (2018.01); *A61B 2034/104* (2016.02); *A61B 2034/105* (2016.02);
(Continued)

(58) Field of Classification Search
CPC ... A61B 34/10; A61B 2034/105; A61B 34/20; A61B 2034/107; A61B 2034/108; A61B 2034/102; A61B 2090/365; A61B 17/15
See application file for complete search history.

(56) References Cited

U.S. PATENT DOCUMENTS

2004/0120469 A1  6/2004  Hebecker et al.
2010/0256479 A1  10/2010  Park et al.
(Continued)

FOREIGN PATENT DOCUMENTS

| WO | 2016116946 A2 | 7/2016 |
| WO | 2019180745 A1 | 9/2019 |
| WO | 2019180746 A1 | 9/2019 |

OTHER PUBLICATIONS

YouTube Video "X-rays part 1—Dr Paul Siffri" by SHCCVideo Hoyle, Apr. 2, 2012, https://www.youtube.com/watch?v=0t5gxD99q4E (Year: 2012).

*Primary Examiner* — Weiming He
(74) *Attorney, Agent, or Firm* — Troutman Pepper Hamilton Sanders LLP

(57) ABSTRACT

A method of generating a custom three-dimensional model of a bone is disclosed. A 2D image of the bone is obtained and an orientation and scale of the 2D image are aligned to a pre-determined coordinate system. Based on the 2D image, a representative bone is identified from a library of representative bones that are aligned to the pre-determined coordinate system. Based on the 2D image, an ideal view of a 3D model of the representative bone is selected. Modifications may be made to the 3D model by using additional representative bones from the library. A custom three-dimensional model of the bone is thereby generated.

26 Claims, 43 Drawing Sheets

Related U.S. Application Data

(60) Provisional application No. 62/951,676, filed on Dec. 20, 2019, provisional application No. 62/658,988, filed on Apr. 17, 2018.

(51) Int. Cl.
| | |
|---|---|
| *G16H 30/40* | (2018.01) |
| *G06F 30/12* | (2020.01) |
| *A61B 17/16* | (2006.01) |
| *A61F 2/46* | (2006.01) |
| *G06T 19/20* | (2011.01) |
| *G06T 17/00* | (2006.01) |
| *G06T 7/00* | (2017.01) |
| *G16H 50/50* | (2018.01) |

(52) U.S. Cl.
CPC . *A61B 2034/107* (2016.02); *A61F 2002/4632* (2013.01); *G06T 2200/08* (2013.01); *G06T 2207/30008* (2013.01); *G06T 2219/2004* (2013.01); *G06T 2219/2016* (2013.01)

(56) References Cited

U.S. PATENT DOCUMENTS

| | | |
|---|---|---|
| 2016/0239632 A1 | 8/2016 | Yu et al. |
| 2017/0018082 A1 | 1/2017 | Hu et al. |
| 2017/0258526 A1* | 9/2017 | Lang ................. A61B 17/1703 |
| 2017/0323443 A1 | 11/2017 | Dhruwdas |

* cited by examiner

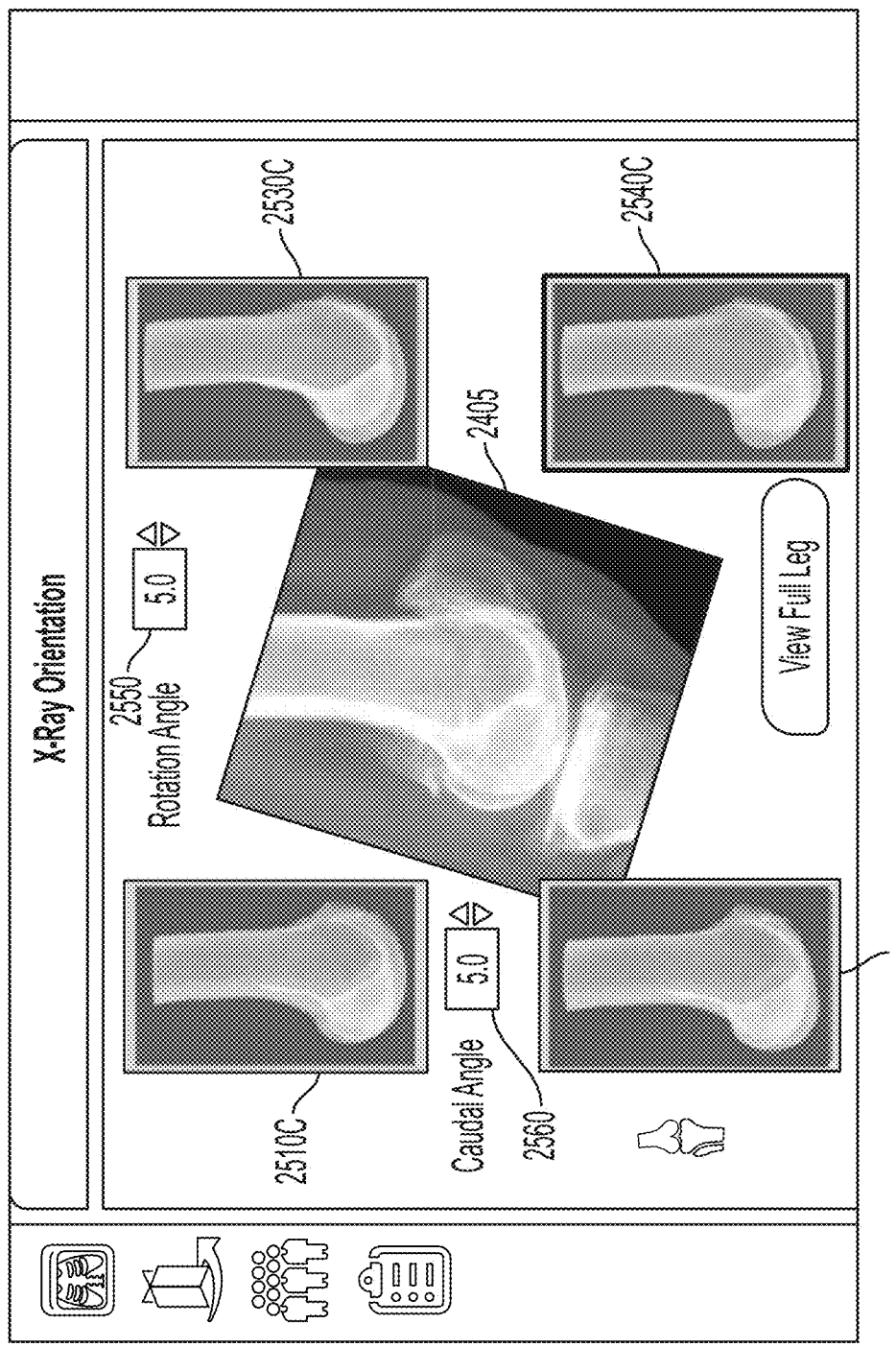

THREE-DIMENSIONAL SELECTIVE BONE MATCHING

CROSS-REFERENCE TO RELATED APPLICATIONS

This application is a continuation in part of U.S. patent application Ser. No. 16/387,151 entitled "Three Dimensional Selective Bone Matching," filed Apr. 17, 2019, which claims the priority benefit of U.S. Provisional Patent Application No. 62/658,988 entitled "Three-Dimensional Guide with Selective Bone Matching," filed Apr. 17, 2018. This application further claims the priority benefit of U.S. Provisional Patent Application No. 62/951,676 entitled "Three-Dimensional Selective Bone Matching from 2D Image Data," filed Dec. 20, 2019. The contents of each of these applications are incorporated herein by reference in their entirety.

TECHNICAL FIELD

The present disclosure relates generally to methods, systems, and apparatuses related to a computer-assisted surgical system that includes various hardware and software components that work together to enhance surgical workflows. The disclosed techniques may be applied to, for example, shoulder, hip, and knee arthroplasties, as well as other surgical interventions such as arthroscopic procedures, spinal procedures, maxillofacial procedures, rotator cuff procedures, ligament repair and replacement procedures. More specifically, the present disclosure relates to methods of creating 3D anatomical models from bi-planar 2D images.

BACKGROUND

As the cost of providing healthcare has continued to rise, many entities are looking for ways to reduce costs. In some cases, insurance companies impose more stringent reimbursement criteria in order to shift away from more expensive treatments. For example, insurance providers may question whether the use of magnetic resonance imaging (MRI) equipment is necessary because of the high cost of using such equipment as compared to other imaging systems, including computed tomography (CT) scanners and X-ray machines. In other cases, less populated or emerging markets may not have access to MRI technology because of the cost of obtaining and operating such systems.

Currently, many patient-specific total joint replacement systems, including Smith & Nephew's VISIONAIRE cutting guides, depend upon the ability to interpret a patient's joint anatomy from a sequence of images produced by an MRI scan. In particular, patient-specific joint replacement procedures require form-fitting surfaces matched to areas that include cartilage surfaces, such as in the knee. MRI scans, which provide three-dimensional images of a scanned anatomical feature including soft tissue, are currently required because other imaging technologies provide insufficient detail for the development of such surfaces. VISIONAIRE is a registered trademark of Smith & Nephew, Inc. of Memphis, Tenn.

Furthermore, the process of converting MRI data into a patient-specific joint replacement instrument may require a significant amount of user intervention and data processing prior to manufacturing the instrument. A user often spends a significant amount of time ensuring that a bone model created using the MRI data matches the patient's bone as closely as possible. In short, the reliance on MRI scans can either preclude certain patients from receiving a joint replacement if an MRI system is not available or inhibit or delay the approval process if an insurance provider denies coverage and requests that other treatments be pursued in advance of total joint replacement.

Prior attempts to create 3D models from 2D imaging data rely heavily on complex mathematical calculations performed by a processor. For example, U.S. Pat. No. 10,217,217 to Dhruwdas discloses a method for obtaining a 3D image using a conventional 2D X-ray image. The method includes determining the camera model (position of the source and the X-ray image with respect to one another) and digital magnification ratio of a 2D X-ray image, extracting contours of a bone from the 2D X-ray image, and identifying 2D anatomical values of the contours. The method further includes importing a 3D template model of the bone, extracting silhouette vertices and their projections according to the camera model, and aligning the 3D template model with respect to the X-ray image. The template is selectively modified to match the 2D anatomical values. A best matching point on the contour is determined for each silhouette vertex projection, which is then back-projected according to the camera model to find a target position closest to the corresponding silhouette vertex. The 3D template model is deformed such that the silhouette vertices achieve the corresponding target positions using a Laplacian Mesh Deformation algorithm. However, the method of Dhruwdas has high computational requirements due to the complex mathematical calculations which must be performed by the processor. Further, the primarily mathematical process results in a highly inefficient approach.

As such, it would be advantageous to have a technology aimed to support the creation of a three-dimensional model of a joint based on X-ray images using a computer-assisted approach and further to support the creation of a bone guide, which may be referred to as a variable bone coupler. It is intended that this approach would alleviate the need for costly 3D imaging (e.g. MRI) while greatly reducing the computational requirements and inefficiencies typically associated with 3D modeling techniques. As such, the approach would not be sensitive to changes in MRI reimbursement and would be available to markets where MRI scans are not readily available.

SUMMARY

A method of generating a custom three-dimensional model of a bone is provided. The method comprises obtaining at least one 2D image of the bone; aligning an orientation and scale of the at least one 2D image to a pre-determined coordinate system; identifying, based on the at least one 2D image, a first representative bone from a library of representative bones, each of the representative bones in the library being aligned to the pre-determined coordinate system; selecting, based on the at least one 2D image, an ideal view of a first 3D model of the first representative bone; and performing one or more modifications to the first 3D model to generate the custom three-dimensional model of the bone, wherein each of the one or more modifications is based on a second representative bone from the library.

According to certain embodiments, performing each of the one or more modifications comprises receiving, based on a user input, an adjustment to one or more points of the first 3D model; identifying, based on the at least one 2D image and the adjustment, a second 3D model of a second representative bone from the library; and updating the first 3D model based on the second 3D model. According to additional embodiments, updating the first 3D model comprises replacing a fragment of the first 3D model including the one or more points with a fragment of the second 3D model including one or more corresponding points. According to additional embodiments, the one or more points comprise at least one of a point on a surface of the first 3D model, a curve on the surface of the first 3D model, a line on surface of the first 3D model, a control point associated with a subdivided segment of the first 3D model, a key point associated with the first 3D model, and a landmark associated with the first 3D model.

According to certain embodiments, aligning an orientation and scale of the at least one 2D image comprises one or more iterations, each iteration comprising modifying the orientation and scale of the at least one 2D image to align the at least one 2D image with a bone template; and selecting, based on the modified at least one 2D image, a potential representative bone from the library. According to additional embodiments, the potential representative bone is the bone template for a subsequent iteration. According to additional embodiments, the first representative bone is the potential representative bone of one of the one or more iterations.

According to certain embodiments, identifying a first representative bone comprises identifying, based on the at least one 2D image, a plurality of potential representative bones from the library of representative bones; and selecting a first representative bone from the plurality of potential representative bones.

According to certain embodiments, the method further comprises identifying one or more key points on the at least one 2D image. According to additional embodiments, identifying a first representative bone is further based on the one or more key points. According to additional embodiments, each of the one or more key points corresponds to at least one of a portion of a bony anatomy, a location of ligament attachment, a bony landmark, an anatomic landmark, a positional extreme, a knee center, a posterior point on a condyle, an anterior notch point, an epicondyle, a point on a femoral AP axis, a mid plane, an intersection point, an expected resection location, an expected position for placement of a surgical tool, a mechanical axis, and an anatomical axis.

According to certain embodiments, selecting an ideal view comprises comparing one or more views of the first 3D model of the first representative bone to the at least one 2D image, each of the one or more views comprising a rotation angle and a caudal angle; and selecting, based on the at least one 2D image, an ideal view of the first representative bone from the one or more views. According to additional embodiments, comparing one or more views comprises adjusting at least one of a rotation angle and a caudal angle of the one or more views, wherein the custom three-dimensional model is based on the ideal view.

A system for generating a custom three-dimensional model of a bone is also provided. The system comprises a processor; and a non-transitory, processor-readable storage medium that stores instructions executable by the processor to obtain at least one 2D image of the bone; align an orientation and scale of the at least one 2D image to a pre-determined coordinate system; identify, based on the at least one 2D image, a first representative bone from a library of representative bones, each of the representative bones in the library being aligned to the pre-determined coordinate system; select, based on the at least one 2D image, an ideal view of a first 3D model of the first representative bone; and perform one or more modifications to the first 3D model to generate the custom three-dimensional model of the bone, wherein each of the one or more modifications is based on a second representative bone from the library.

According to certain embodiments, the instructions are executable by the processor to receive, based on a user input, an adjustment to one or more points of the first 3D model; identify, based on the at least one 2D image and the adjustment, a second 3D model of a second representative bone from the library; and update the first 3D model based on the second 3D model. According to additional embodiments, the instructions are executable by the processor to replace a fragment of the first 3D model including the one or more points with a fragment of the second 3D model including one or more corresponding points. According to additional embodiments, the one or more points comprise at least one of a point on a surface of the first 3D model, a curve on the surface of the first 3D model, a line on surface of the first 3D model, a control point associated with a subdivided segment of the first 3D model, a key point associated with the first 3D model, and a landmark associated with the first 3D model.

According to certain embodiments, the instructions are executable by the processor to complete one or more iterations, each iteration comprising modifying the orientation and scale of the at least one 2D image to align the at least one 2D image with a bone template; and selecting, based on the modified at least one 2D image, a potential representative bone from the library. According to additional embodiments, the potential representative bone is the bone template for a subsequent iteration. According to additional embodiments, the first representative bone is the potential representative bone of one of the one or more iterations.

According to certain embodiments, the instructions are executable by the processor to identify, based on the at least one 2D image, a plurality of potential representative bones from the library of representative bones; and select a first representative bone from the plurality of potential representative bones.

According to certain embodiments, the instructions are further executable by the processor to identify one or more key points on the at least one 2D image. According to additional embodiments, the instructions executable by the processor to identify the first representative bone based on the one or more key points. According to additional embodiments, each of the one or more key points corresponds to at least one of a portion of a bony anatomy, a location of ligament attachment, a bony landmark, an anatomic landmark, a positional extreme, a knee center, a posterior point on a condyle, an anterior notch point, an epicondyle, a point on a femoral AP axis, a mid plane, an intersection point, an expected resection location, an expected position for placement of a surgical tool, a mechanical axis, and an anatomical axis.

According to certain embodiments, the instructions are executable by the processor to compare one or more views of the first 3D model of the first representative bone to the at least one 2D image, each of the one or more views comprising a rotation angle and a caudal angle; and select, based on the at least one 2D image, an ideal view of the first representative bone from the one or more views. According to additional embodiments, the instructions are executable by the processor to adjust at least one of a rotation angle and a caudal angle of the one or more views, wherein the custom three-dimensional model is based on the ideal view.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIGS. 25A-25D depict a process of orienting views of a representative bone from a library relative to a 2D image in accordance with an embodiment.

DETAILED DESCRIPTION

Figure 1:
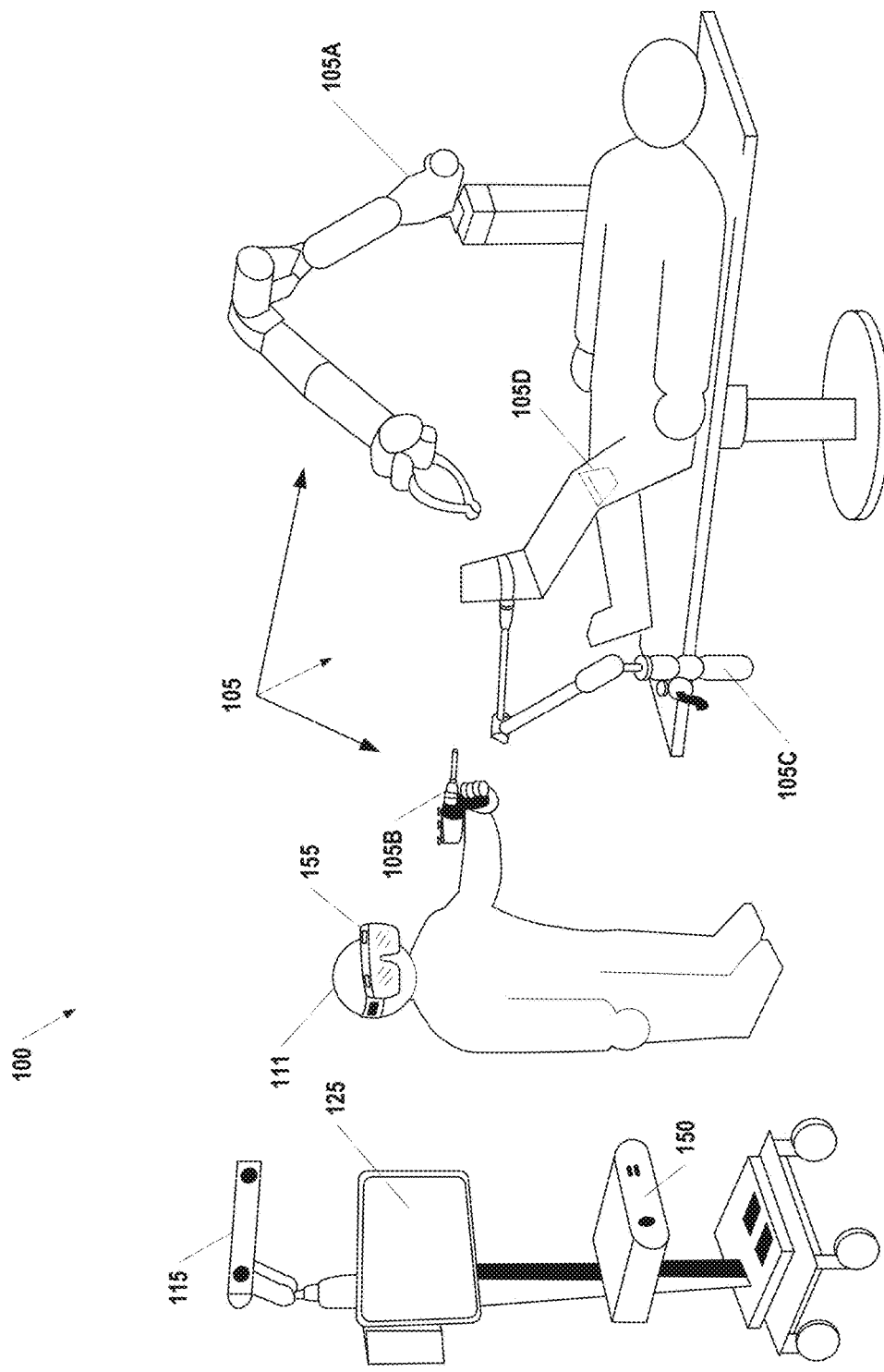
FIG. 1 depicts an operating theatre including an illustrative computer-assisted surgical system (CASS) in accordance with an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon could also apply, in some embodiments to a technician or nurse.

Various embodiments, discussed herein, address the issues discussed above by providing an intermediate stem extension or coupler that couples a femoral or tibial articular component (e.g., tibial tray and articular insert) with a stem extension and/or tracking component. Furthermore, the coupler stem connection means may be offset from the articular component or tracking component at a known distance and orientation and is angled relative to the desired articular component's varus/valgus (V/V) and/or flexion/extension (F/E) desired angular orientation and the desired stem's angular orientation. The invention allows variable alignment to an anatomical or kinematic alignment or to a surgeon-prescribed alignment such as human bone deformities, muscle structures, and/or flexion/extension balance.

In revision knee replacements, the typical femoral component is usually supported by an attached intramedullary (IM) stem. The stem connection means for most revision femoral components are typically fixed at a set varus/valgus (V/V) angle coronally; typically, about six (6) degrees. However, due to variations in bone anatomy, this varus/valgus (V/V) angle can vary from patient to patient. In another embodiment, the variation in bony anatomy may also vary sagitally relative to the articular cartilage geometry (i.e. distal exterior/outside part of the bone) and the position of the IM canal (interior/inside of the bone). It is desirable to place the articular part of the femoral component in an optimal position for a given patient relative to a mechanical or anatomical axis in regards to the V/V angle coronally while optimally positioning the A/P position, M/L position, and to a lesser extent, the internal/external rotation (on a transverse plane) while rigidly fixing a stem to the femoral component in a position such that the stem fits centrally within the intramedullary canal. The intermediate stem couple of the present invention accomplishes all these goals.

CASS Ecosystem Overview

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below).

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 can also include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 can also be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, hand-held tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they can also be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient can also involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process can also include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 can also utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step can also utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon.

In some embodiments, the powered impaction device includes feedback sensors that gather data during instrument use, and send data to a computing device such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill.

Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 can also place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in U.S. Provisional Patent Application No. 62/723,898 filed Aug. 28, 2018 and entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various aspects of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure.

In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 2C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 2A:
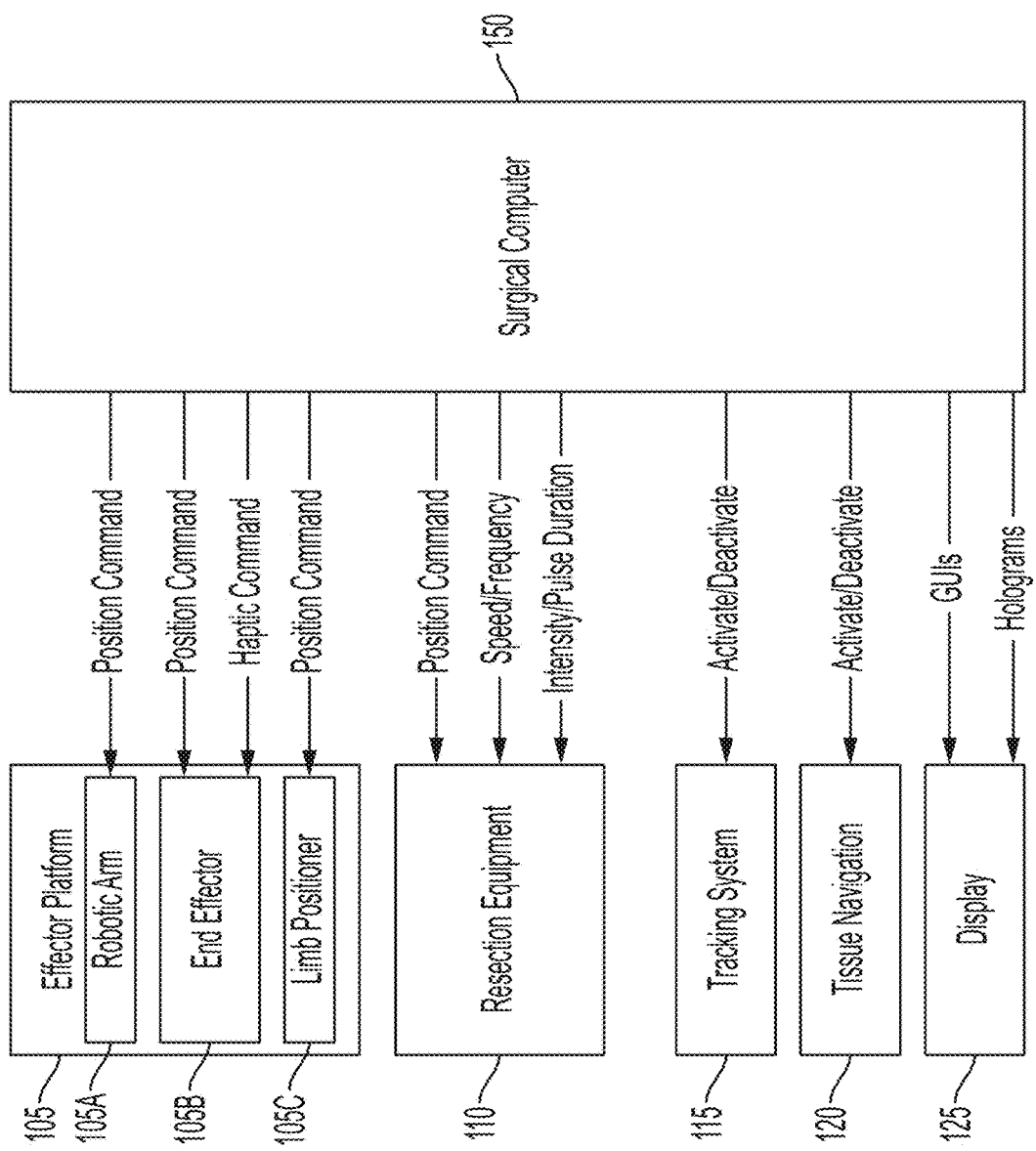
FIG. 2A depicts illustrative control instructions that a surgical computer provides to other components of a CASS in accordance with an embodiment.
Figure 2B:
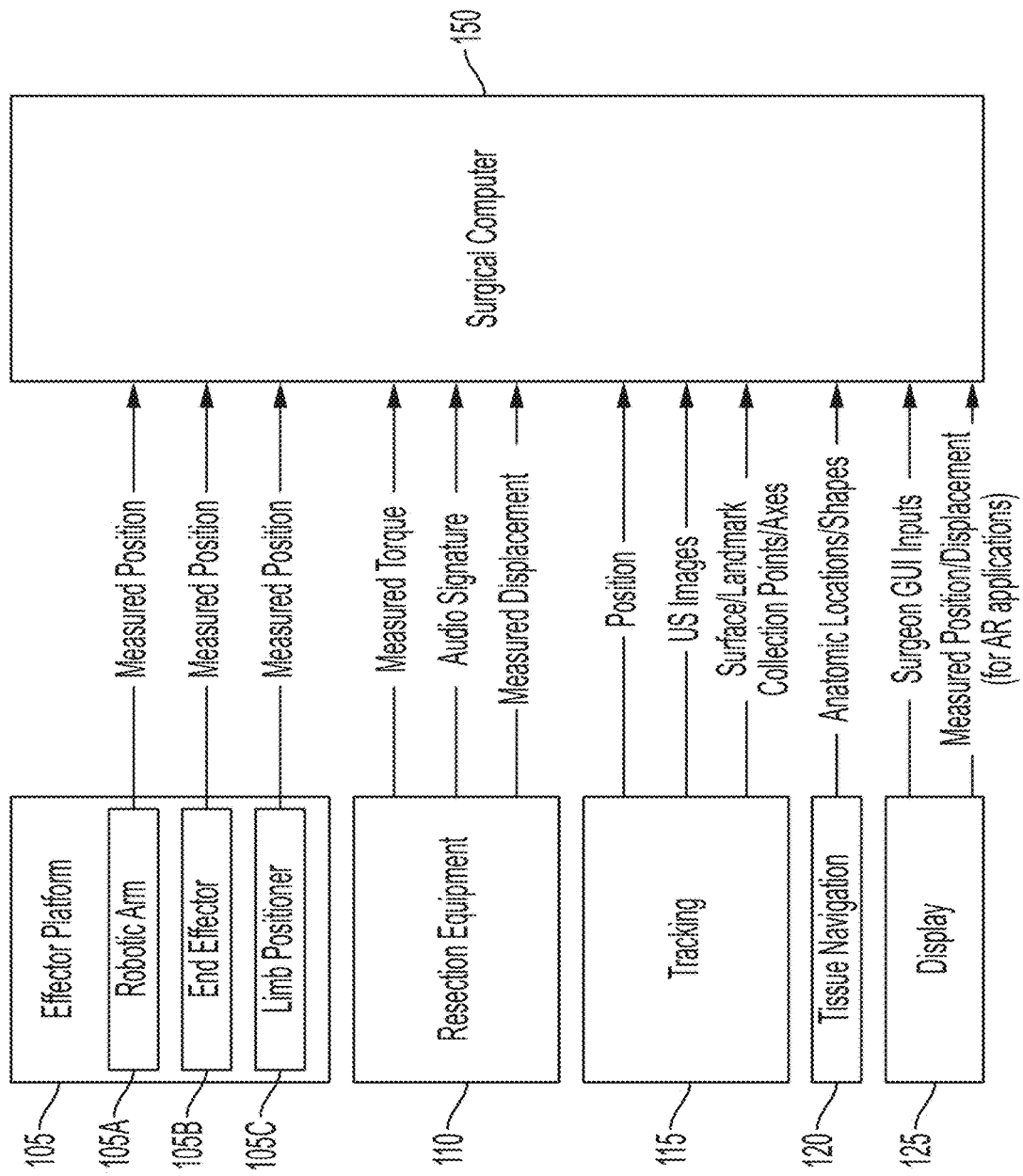
FIG. 2B depicts illustrative control instructions that components of a CASS provide to a surgical computer in accordance with an embodiment.

FIGS. 2A and 2B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 2A shows examples of some of the control instructions that the Surgical Computer 150 provides to other components of the CASS 100, according to some embodiments. Note that the example of FIG. 2A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 2A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 2A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various aspects of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 can also include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 can also provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 can also preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 2C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in U.S. Provisional Patent Application No. 62/719,415 entitled "Patient Specific Surgical Method and System," the entirety of which is incorporated herein by reference.

FIG. 2B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 2B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQ5D-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 2C.

Figure 2C:
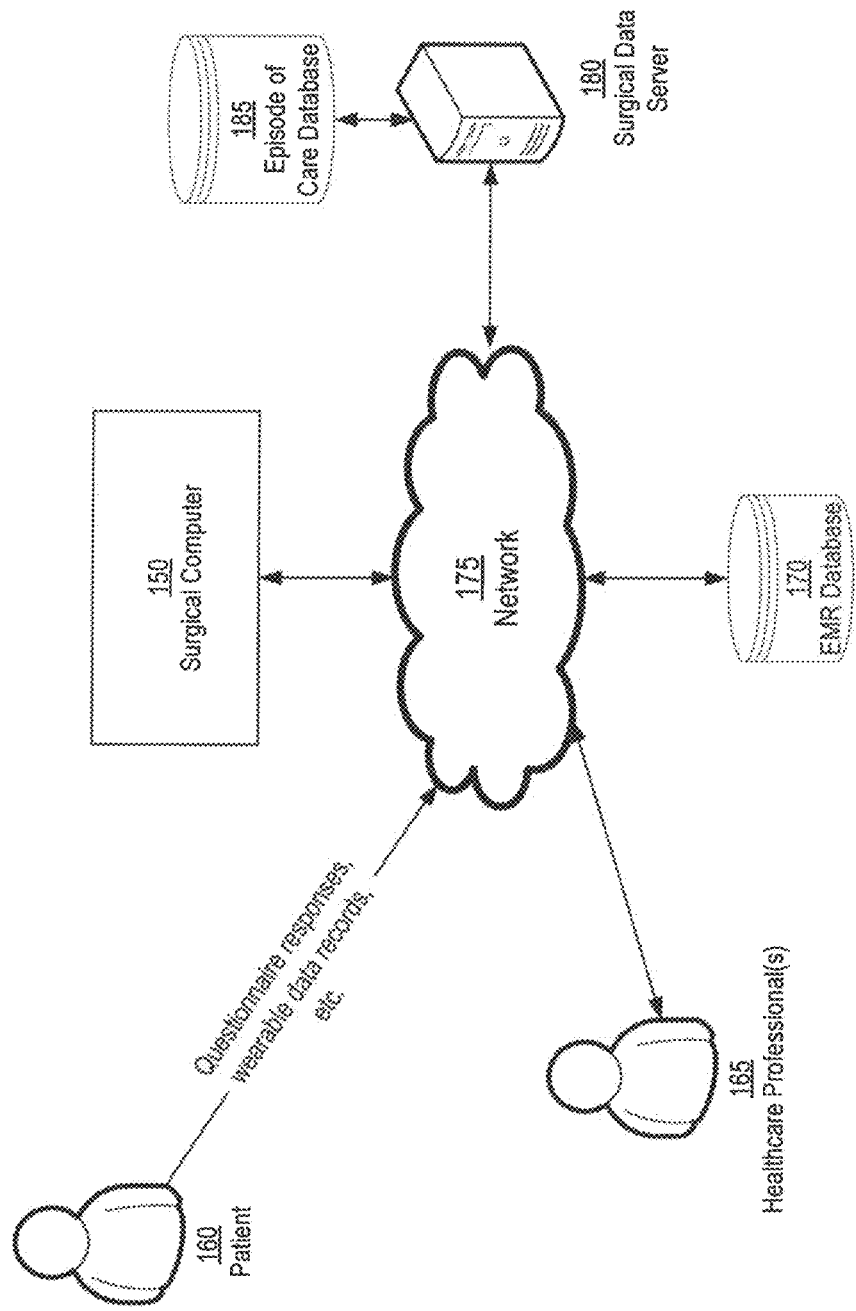
FIG. 2C depicts an illustrative implementation in which a surgical computer is connected to a surgical data server via a network in accordance with an embodiment.

FIG. 2C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 2C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 2C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 2A-2C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patient-centric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in U.S. Patent Application No. 62/783,858 filed Dec. 21, 2018 and entitled "Methods and Systems for Providing an Episode of Care," the entirety of which is incorporated herein by reference.

Open Versus Closed Digital Ecosystems

In some embodiments, the CASS 100 is designed to operate as a self-contained or "closed" digital ecosystem. Each component of the CASS 100 is specifically designed to be used in the closed ecosystem, and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS 100 to ensure that certain compatibility, security, and reliability standards are met. For example, the CASS 100 can be designed such that a new component cannot be used with the CASS unless it is certified by the company.

In other embodiments, the CASS 100 is designed to operate as an "open" digital ecosystem. In these embodiments, components may be produced by a variety of different companies according to standards for activities, such as communication, storage, and security. Thus, by using these standards, any company can freely build an independent, compliant component of the CASS platform. Data may be transferred between components using publicly available application programming interfaces (APIs) and open, shareable data formats.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial component including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation(s) |
|---|---|---|
| Size | Posterior | The largest sized implant that does not overhang medial/lateral bone edges or overhang the anterior femur. A size that does not result in overstuffing the patella femoral joint |
| Implant Position - Medial Lateral | Medial/lateral cortical bone edges | Center the implant evenly between the medial/lateral cortical bone edges |
| Resection Depth - Varus Knee | Distal and posterior lateral | 6 mm of bone |
| Resection Depth - Valgus Knee | Distal and posterior medial | 7 mm of bone |
| Rotation - Varus/Valgus | Mechanical Axis | 1° varus |
| Rotation - External | Transepicondylar Axis | 1° external from the transepicondylar axis |
| Rotation - Flexion | Mechanical Axis | 3° flexed |

Additional examples of parameters that could be optimized for a given TKA tibial implant by the CASS 100 include the following:

| Parameter | Reference | Exemplary Recommendation(s) |
|---|---|---|
| Size | Posterior | The largest sized implant that does not overhang the medial, lateral, anterior, and posterior tibial edges |
| Implant Position | Medial/lateral and anterior/posterior cortical bone edges | Center the implant evenly between the medial/lateral and anterior/posterior cortical bone edges |
| Resection Depth - Varus Knee | Lateral/Medial | 4 mm of bone |
| Resection Depth - Valgus Knee | Lateral/Medial | 5 mm of bone |
| Rotation - Varus/Valgus | Mechanical Axis | 1° valgus |
| Rotation - External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

Operative Patient Care System

Figure 3:
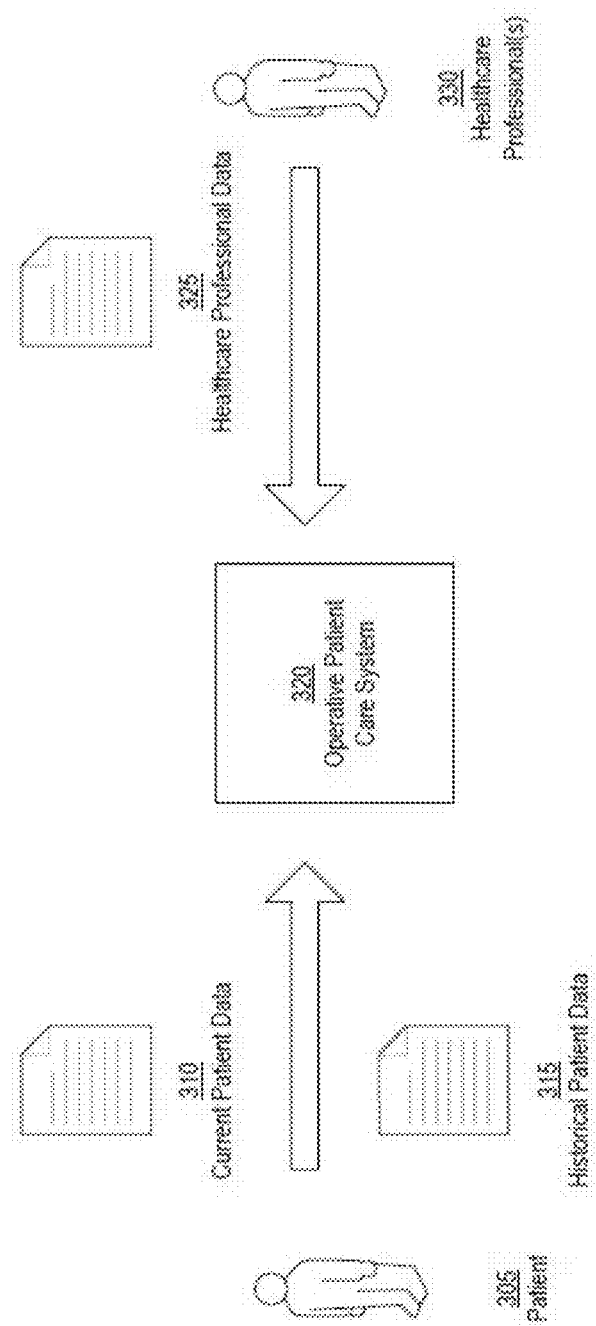
FIG. 3 depicts an operative patient care system and illustrative data sources in accordance with an embodiment.

The general concepts of optimization may be extended to the entire episode of care using an Operative Patient Care System 320 that uses the surgical data, and other data from the Patient 305 and Healthcare Professionals 330 to optimize outcomes and patient satisfaction as depicted in FIG. 3.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care; aligning dynamic patient, healthcare economic, and surgeon preferences with patient-desired outcomes; executing a surgical plan resulting in proper bone alignment and balance, etc.; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 320 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 320 tracks adherence to the suggested or recommended plan, and adapts the plan based on patient/care provider performance. Once the surgical treatment plan is complete, collected data is logged by the Operative Patient Care System 320 in a historical database. This database is accessible for future patients and the development of future treatment plans. In addition to utilizing statistical and mathematical models, simulation tools (e.g., LIFEMOD®) can be used to simulate outcomes, alignment, kinematics, etc. based on a preliminary or proposed surgical plan, and reconfigure the preliminary or proposed plan to achieve desired or optimal results according to a patient's profile or a surgeon's preferences. The Operative Patient Care System 320 ensures that each patient is receiving personalized surgical and rehabilitative care, thereby improving the chance of successful clinical outcomes and lessening the economic burden on the facility associated with near-term revision.

In some embodiments, the Operative Patient Care System 320 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 305 provides inputs such as Current Patient Data 310 and Historical Patient Data 315 to the Operative Patient Care System 320. Various methods generally known in the art may be used to gather such inputs from the Patient 305. For example, in some embodiments, the Patient 305 fills out a paper or digital survey that is parsed by the Operative Patient Care System 320 to extract patient data. In other embodiments, the Operative Patient Care System 320 may extract patient data from existing information sources, such as electronic medical records (EMRs), health history files, and payer/provider historical files. In still other embodiments, the Operative Patient Care System 320 may provide an application program interface (API) that allows the external data source to push data to the Operative Patient Care System. For example, the Patient 305 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 320. Similarly, the Patient 305 may have a digital application on his or her mobile or wearable device that enables data to be collected and transmitted to the Operative Patient Care System 320.

Current Patient Data 310 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 315 can include, but is not limited to, activity level, preexisting conditions, comorbidities, pre-hab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels or pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 330 conducting the procedure or treatment may provide various types of data 325 to the Operative Patient Care System 320. This Healthcare Professional Data 325 may include, for example, a description of a known or preferred surgical technique (e.g., Cruciate Retaining (CR) vs Posterior Stabilized (PS), up- vs down-sizing, tourniquet vs tourniquet-less, femoral stem style, preferred approach for THA, etc.), the level of training of the Healthcare Professional(s) 330 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 325 can be captured, for example, with paper or digital surveys provided to the Healthcare Professional 330, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socioeconomic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFEMOD®, AnyBody, or OpenSIM). It is noted that the data inputs described above may not be available for every patient, and the treatment plan will be generated using the data that is available.

Prior to surgery, the Patient Data 310, 315 and Healthcare Professional Data 325 may be captured and stored in a cloud-based or online database (e.g., the Surgical Data Server 180 shown in FIG. 2C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Once the procedure is complete, all patient data and available outcome data, including the implant size, position and orientation determined by the CASS 100, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (X-ray, CT, MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO® or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 4A:
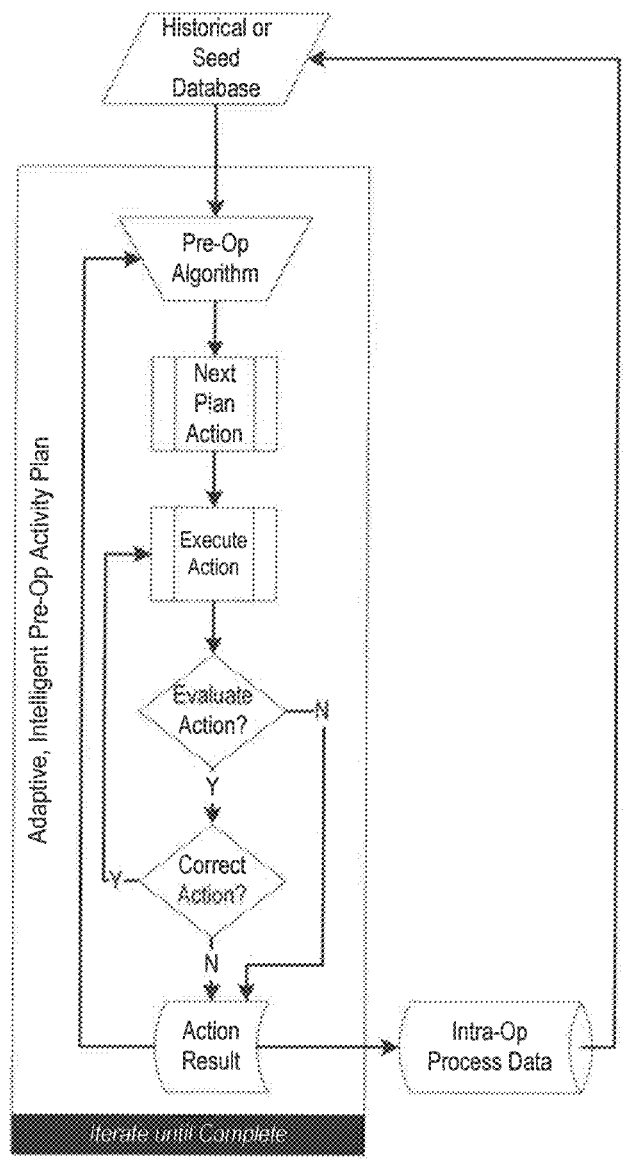
FIG. 4A depicts an illustrative flow diagram for determining a pre-operative surgical plan in accordance with an embodiment.
Figure 4B:
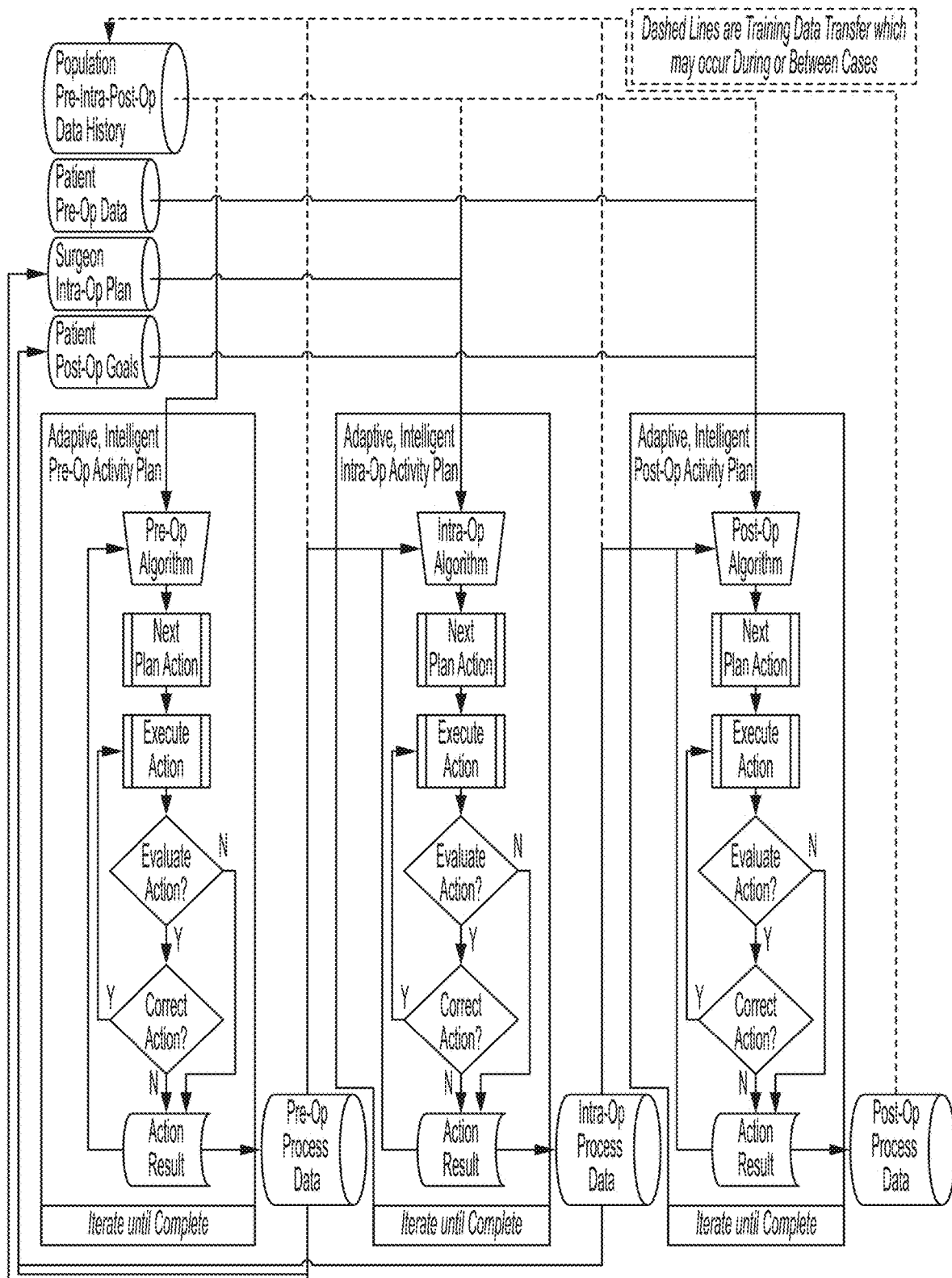
FIG. 4B depicts an illustrative flow diagram for determining an episode of care including pre-operative, intraoperative, and post-operative actions in accordance with an embodiment.

FIG. 4A illustrates how the Operative Patient Care System 320 may be adapted for performing case plan matching services. In this example, data is captured relating to the current patient 310 and is compared to all or portions of a historical database of patient data and associated outcomes 315. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular aspect of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 4B and can be applied to any type of surgery utilizing the CASS 100.

Surgery Process Display

As noted above with respect to FIGS. 1-2C, the various components of the CASS 100 generate detailed data records during surgery. The CASS 100 can track and record various actions and activities of the surgeon during each step of the surgery and compare actual activity to the pre-operative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a playback of the surgical plan or toggle between different aspects of the actual surgery vs. the surgical plan could provide benefits to the surgeon and/or surgical staff, allowing such persons to identify any deficiencies or challenging aspects of a surgery so that they can be modified in future surgeries. Similarly, in academic settings, the aforementioned GUIs can be used as a teaching tool for training future surgeons and/or surgical staff. Additionally, because the data set effectively records many aspects of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, aspects such as implant type and dimension, patient demographics, etc. can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

Figure 4C:
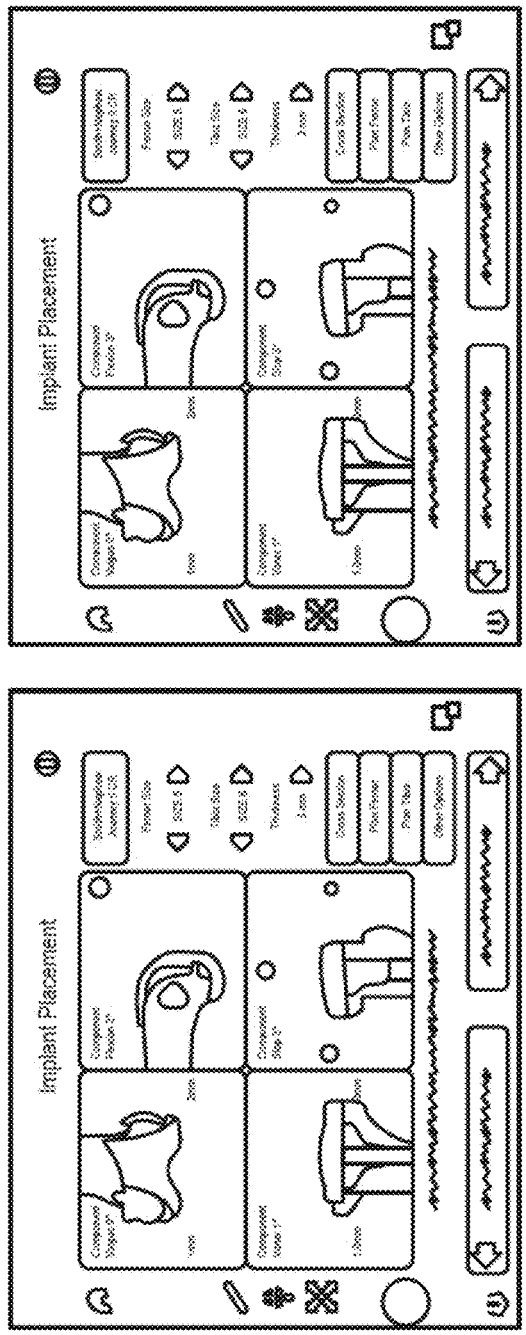
FIG. 4C depicts an illustrative graphical user interfaces including images depicting an implant placement in accordance with an embodiment.
Figure 4C:
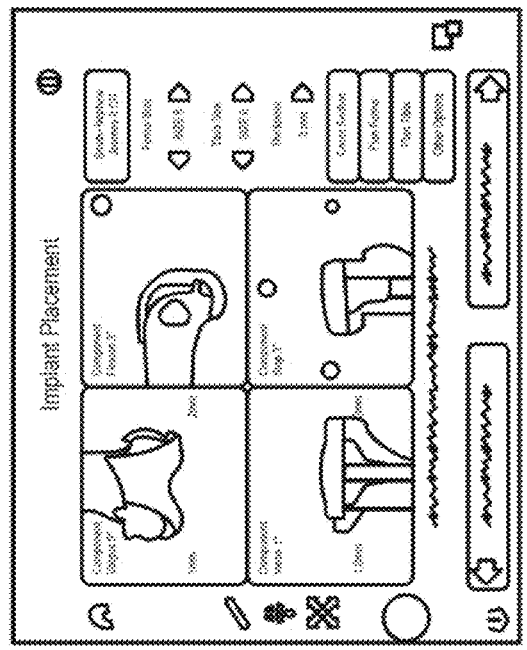

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150 may predict or recommend the state for the next 5 minutes in 30 second increments. Using this information, the surgeon can utilize a "process display" view of the surgery that allows visualization of the future state. For example, FIG. 4C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other aspects of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various aspects of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using the Point Probe to Acquire High-Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. Provisional Patent Application No. 62/658,988, filed Apr. 17, 2018 and entitled "Three Dimensional Guide with Selective Bone Matching," the entirety of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT; thus, in some embodiments, the point probe is used to paint the GT to provide a high resolution view of the area. Similarly, in some embodiments, it may be useful to have a high-resolution view of the Lesser Trochanter (LT). For example, during hip arthroplasty, the Dorr Classification helps to select a stem that will maximize the ability of achieving a press-fit during surgery to prevent micromotion of femoral components post-surgery and ensure optimal bony ingrowth. As is generated understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data could also be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light interferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

As discussed herein, an embodiment may allow for the creation of 3D models from 2D image data that can be more easily acquired than volumetric image data such as MRI or CT. 3D models may include one of CAD, IGES, STL, VRML, DXF, OBJ, or similar files. In some embodiments, subdivision of an anatomical model may create a large library of bone shapes, i.e., more than are available with standard statistical shape model (SSM) techniques. Thus, the semi-automated system as discussed herein may require input from an imaging expert who provides quality control.

Figure 5:
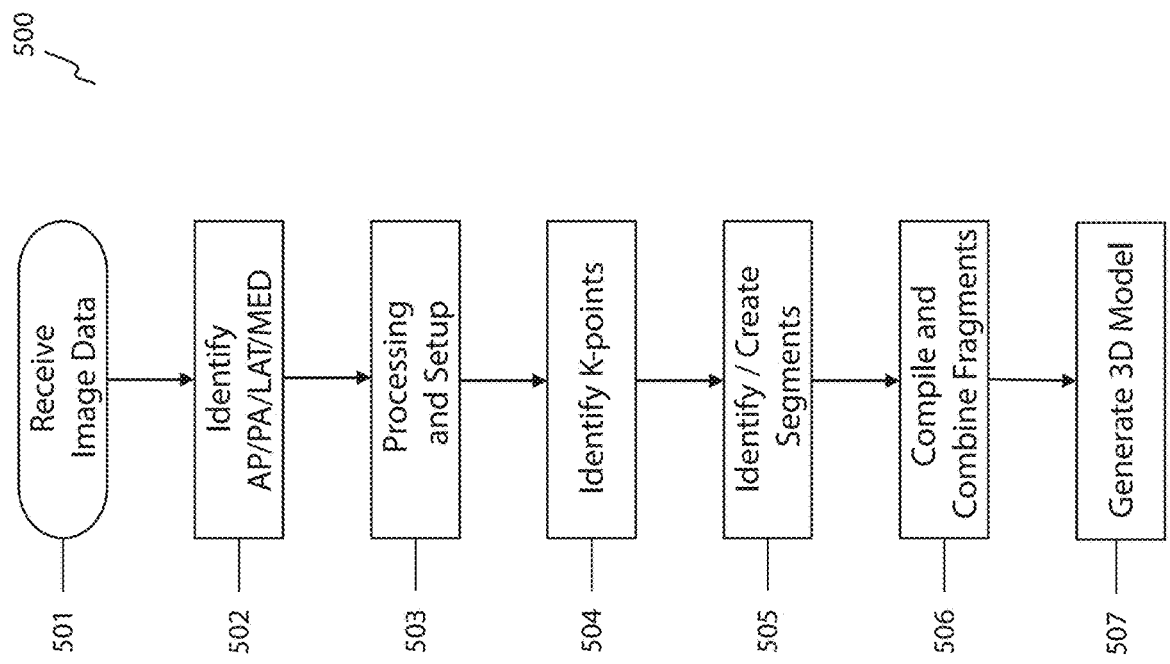
FIG. 5 depicts an illustrative method for generating a 3D model based on 2D patient image data in accordance with an embodiment.
Figure 6B:
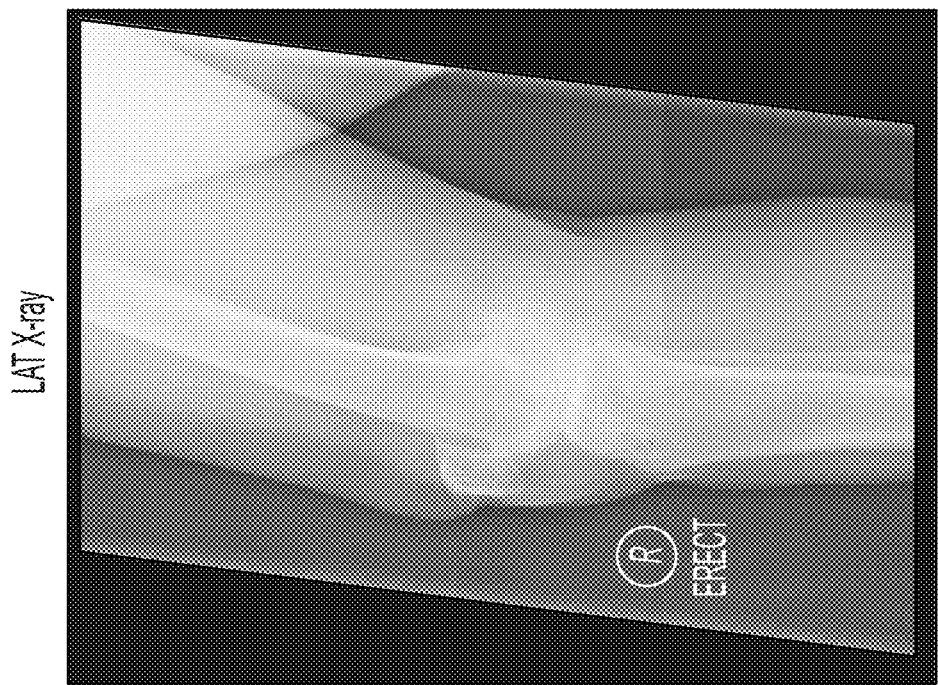
FIG. 6B depicts another illustrative example of one or more 2D medical images in accordance with an embodiment.
Figure 6A:
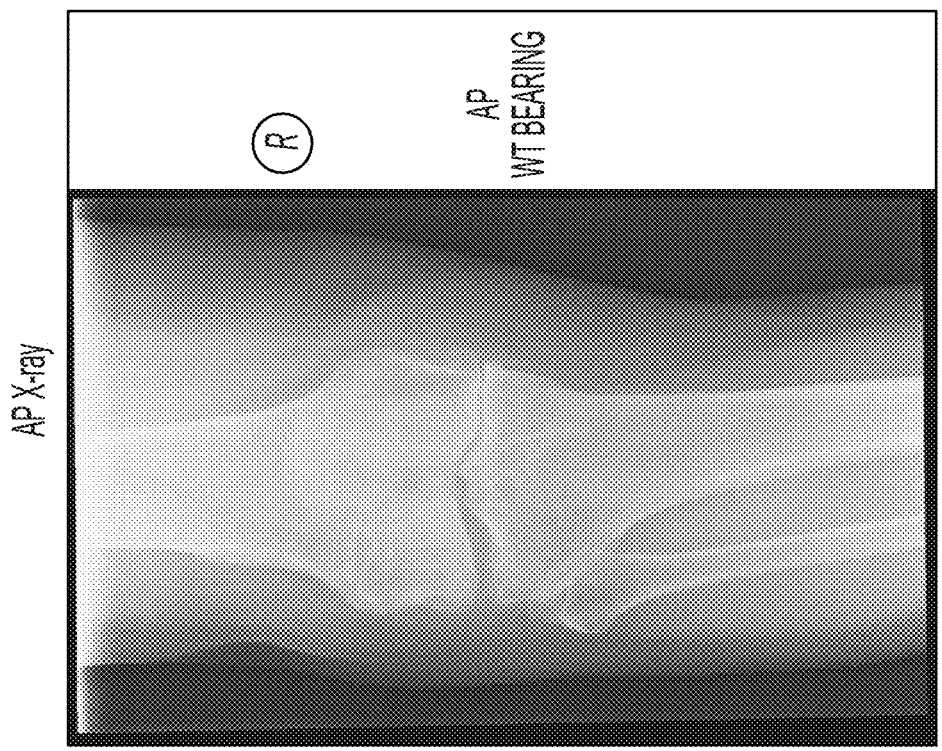
FIG. 6A depicts an illustrative example of one or more 2D medical images in accordance with an embodiment.

Referring now to FIG. 5, an example embodiment 500 may receive a plurality of 2D images of an anatomical feature of a patient 501. In a further embodiment, the anatomical feature (i.e., landmark) may be at least one of an epicondyle, a tibial spine, Whiteside's line, a trans-epicondylar axis, tibial tuberosity, a mechanical axis, an anatomic axis, the medial malleolus, the adductor tubercle, or any other useful anatomical feature known now or in the future. In another embodiment, the received image data may comprise any form of 2D patient image data, such as, for example, X-ray data, fluoroscopy image data, projectional radiograph data, 2D computed tomography images, 2D echocardiography images, and the like. As further discussed herein, the image data may be acquired by a healthcare provider (e.g., surgeon, clinician, nurse, etc.), by a service provider (e.g., healthcare manufacturer), and/or by a third party healthcare source (e.g., a previous hospital, ambulatory surgery center, etc.).

Once the patient image data is received 501, the various images are reviewed and analyzed to ensure proper view, orientation, shape, and classification and to determine whether the one or more 2D images require further processing 502. Thus, in an embodiment, a processor may evaluate the provided images to identify whether the provided images are one or more of: a coronal view, a sagittal view, a posterior/anterior (PA) view, an anterior/posterior (AP) view, a lateral to medial (LAT) view, a medial-to-lateral (MED) view, a load bearing view, and/or a non-load bearing view.

In one embodiment, the review and analysis of the various 2D images 502 may be performed autonomously by using one or more known image analysis techniques including, but not limited to, object recognition, image segmentation, single particle tracking, and the like. In a further embodiment, the system may request or prompt a user to input additional information. It should be understood by those of ordinary skill in the art, that the additional user input may be used to correct or improve the existing software-based analysis. Moreover, in an alternative embodiment, the analysis 502 may be entirely or primarily based on the user input. For example, the plurality of 2D images may contain an advanced deformity or may not be within the bounds of the analysis software.

Once the images are reviewed 502 and a determination has been made as to whether further processing is required, one or more of the 2D patent images may be processed or enhanced 503. As discussed further herein (e.g., with reference to FIGS. 6-13), one or more features of the 2D patient image data may be moved, cropped, rotated, flipped, lightened, darkened, highlighted, and/or identified. In a further embodiment, a plurality of points at or near the expected resections, mid planes, intersection points, and size and direction extremes (e.g., K15 points, bony landmarks, anatomic landmarks, etc.) may be identified 504 within the processed (i.e., updated) plurality of images. In a further embodiment, the plurality of identified points are related to features and/or associated with a portion of an anatomical feature or landmark. Various examples of anatomical landmarks are discussed herein.

In some embodiments, each of the plurality of points may be associated with a subdivided segment. These points, or control points, may be linked to certain anatomic features, such as, for example, the knee center, posterior points on the lateral and medial condyles, an anterior notch point, the lateral and medial epicondyles, points along the femoral AP axis, or the like. Additionally or alternatively, the control points may be linked to, for example, the custom points on the tibia, knee center, lateral and medial low points on the plateau, tibial tubercle, etc.

In one embodiment, the number and location of control points may correspond to the number and location of vertices on the surface of a tessellated bone model. In an additional embodiment, the number of control points may be predetermined, and the tessellated bone model may be disassembled to create the corresponding number of vertices. In some embodiments, the control points may be used for localized morphing of the associated bone shapes. As such, manipulation of the handles may alter the shape of the associated sub-segment. For example, the handles could be moved in a direction of greatest variation across bone shapes in the historical library, thereby allowing the final bone shape to comprise a combination of scaled and interpolated bone segments from the input library based on the region of bone associated with the handle.

Based on the identified points, the anatomical feature(s) of the patient (i.e., the feature(s) depicted in the received image data 501) are segmented into a number of portions 505. Thus, in some embodiments, an anatomical area, which is adjacent to one of the plurality of points, may be mapped or modeled based on the received plurality of images 501. In a further embodiment, a virtual model (e.g., a plurality of estimated values and markers relative to the adaptively derived point(s)) may be created for each segmented portion 505, such that each segment may have one or more characteristics or a shape as dictated by the analysis of the 2D images compared to the virtual model (e.g., steps 502, 503, and 504 of FIG. 5).

In an embodiment, the components of the virtual model may be compared with a library of historical 2D medical images. It should be understood, that any of the various methods of image analysis discussed herein may be utilized to determine and/or identify which, if any, of the images in the historical library closely match the received image data 501. Accordingly, all, or a portion, of the received 2D patient images 501 may be compared with existing 2D patient images to find a best fit or best match. Once a best-fitting historical image(s) is identified, one or more 3D patient images may be accessed that directly correlate to the historical 2D image. Thus, in some embodiments, the library of historical medical images contains one or more 3D images that correspond to each 2D patient image. Stated differently, if a patient were to visit a hospital or medical facility and have both 2D and 3D images taken of their anatomy, those images may be stored in the library of historical medical images for use by the applications discussed herein.

Figure 16:
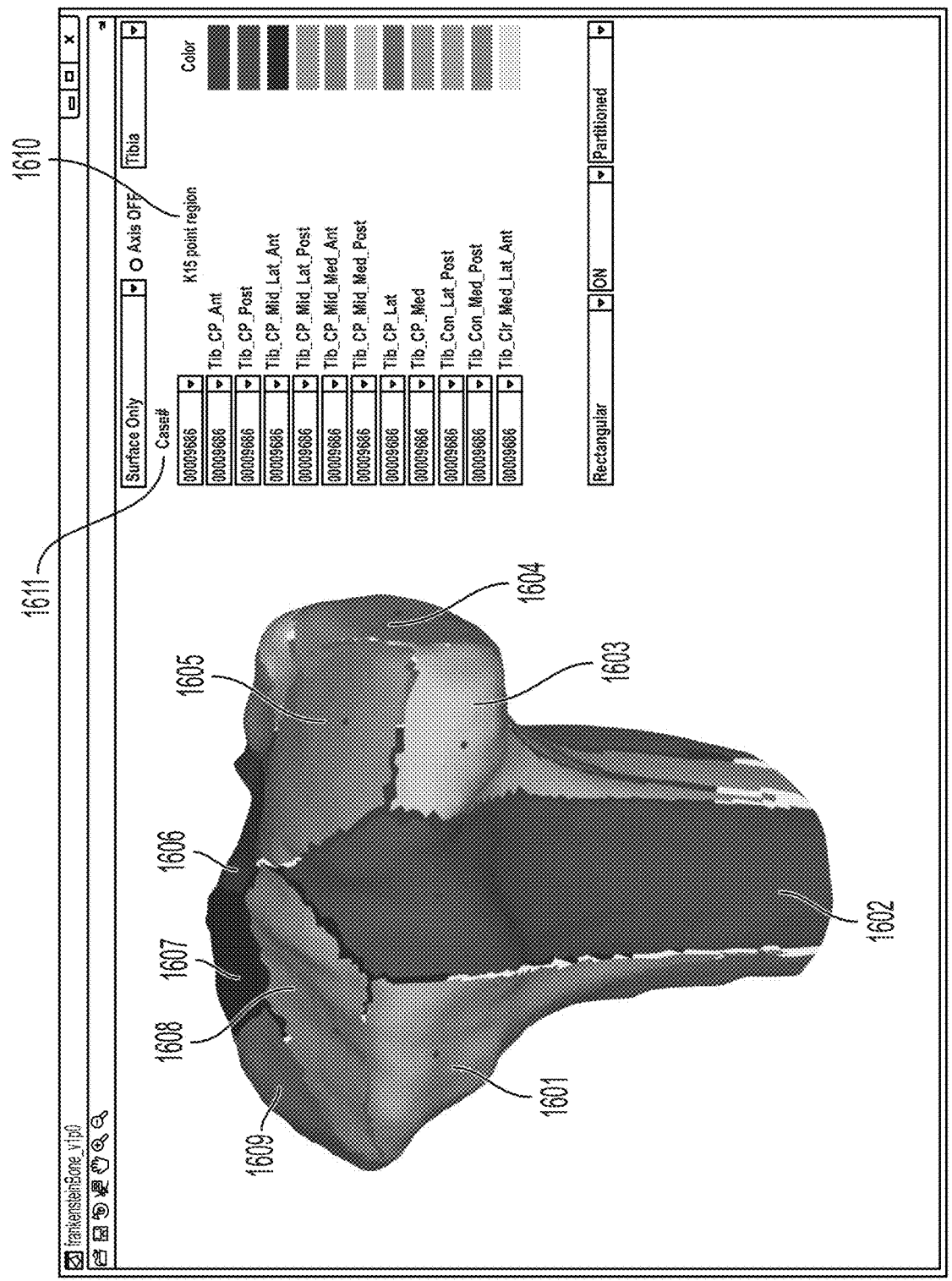
FIG. 16 depicts an illustrative example of a generated 3D model in accordance with an embodiment.

In an embodiment, once a historical image has been found that closely matches each segmented (e.g., fragmented, partitioned, etc.) portion 505, the various 3D image data can be compiled and/or combined to create a hypothetical 3D model of patient's anatomy 506, such as the model shown in FIG. 16. When the fragments are combined, the areas where two or more fragments meet may be normalized or smoothed. As each fragment is processed, a statistical analysis may be performed to generate the most accurate and normalized patient anatomy (e.g., the surface of a patient's bone), thereby ensuring the simulated bone is consistent with the shape(s) of typical bones. In a further embodiment, once the anatomical feature (e.g., bone surface) has been properly combined, a 3D model may be generated 507.

It should be understood that various alternative embodiments are also possible. For example, bone segmentation may not be performed in an embodiment. In this embodiment, a case processing engineer and/or end-user (e.g., a surgeon or other hospital staff) may match the patient's anatomical feature (e.g., bone) to the X-rays using the 3D images of other scans. In a further embodiment, the 3D images of the other scans may be combined with one or more X-ray images. In another embodiment, a synthetic 2D image (e.g., an image generated from a library of known 3D patient bone models) may be generated that matches the patient's 2D images (e.g., A-P X-rays, M-L X-rays, etc.).

In additional embodiments, the historical image library may include segmented bone models, and a user may rely on such models to serve as a surrogate for any subsequent segmentation that would may be needed. Moreover, some embodiments may rely on an outline and/or silhouette. In various other embodiments, the patient's anatomical features may not necessarily be recreated in its entirety. Thus, in some embodiments, a glove-type fit may be created. In other embodiments only discrete arms, pads, and/or other contact features may be included. In further embodiments, some or all of the pre-operative decisions depicted in the pre-op plan, such as, for example, the size, position, and potential pin-hole locations or cut slots may also be represented. In some embodiments, a functional approximation may be created, such that a surgeon or medical staff member has sufficient information to identify location information for a cutting slot, bone marker, pin, cut guide, or the like. As discussed herein, various guides may exist or be used with the embodiments discussed herein. As would be understood by someone of ordinary skill in the art, a guide or alignment tool maybe referred to, herein and in the art, as a variable bone coupler.

As discussed herein, surgically pertinent aspects of a patient feature (e.g., a bone, ligament, cartilage, etc.) may be estimated, rather than forming a comprehensive recreation of the entire feature. Thus, it may not be required to create a complete or full model in some embodiments. Those having ordinary skill in the art will understand that creating 3D geometry from MRI or CT is a known process, However, creating a 3D model from 2D images is less straightforward. Thus, the embodiments disclosed herein, should not be compared to 3D reconstructions using such 3D image capturing systems. Rather, the various embodiments discussed herein more closely relates to a system that uses two or more 2D views.

It is foreseeable that at least some variable bone coupler guides may still be rapid-manufactured and single-use. Thus, in some embodiments, options may be provided for the end user to adjust a size of a suggested variable bone coupler configuration or otherwise revise the instrument. For example, the user can remove a physical (e.g., manufactured) contact point, such as, by breaking off a tab or folding a surface over if the contact point does not seem appropriate. Similarly, the contacts of a variable bone coupler could be raised to increase the resection depth if the user deems the resection depth to be too shallow. In a further embodiment, the contact point or tab (i.e., feature) may be removed or adjusted to allow for existing soft tissue (e.g., meniscus and/or other remnant soft tissue).

Thus, in some embodiments, a repositioning of a custom guide may be possible not only before manufacturing, but also at the time of surgery. In other words, fine adjustment of the cut guide can optionally be performed. As discussed herein, extremely high accuracy and precision, which are major drawbacks of the current patient specific instrumentation market, may not be required. Rather, an improved system and method for approximation of a patient's anatomy that is sufficient for various functions, is described herein. If an end user, such as a surgeon, finds the instrument to be sub-optimal, the end user may make minor adjustments (e.g., removing a contact point) to allow additional degrees of freedom.

Accordingly, the embodiments discussed herein generally relate to an automated, or semi-automated, software tool that can create a 3D representation of a patient's anatomy (e.g., bone and articular cartilage) based on a plurality of bi-planar images. In some embodiments, the model is partitioned into subdivided surfaces (i.e., sub-surfaces) and selectively manipulated by a system, or a user, to adjust the working model to match the received 2D images 501. In some embodiments, the target shape of the model may be dictated by 2D images of the patient's anatomy. In a further embodiment, fine-tuning of the patient's anatomy (e.g., one or more bones) may leverage information gleaned from the starting point bone. That is, in each corresponding area of the bone model, characteristics (e.g., parameters derived) from that area of the initial bone can be used to determine how one or more adjustments are applied. In some embodiments, the 2D images may be used as a measurement tool, even if/when the points and/or segments are outside the radiographs. In another embodiment, the points may best be represented on the bone (e.g., non-cartilaginous area). Areas that are perpendicular to the radiograph may be repositioned in the 2D image, thereby helping determine the remaining bone geometry.

An illustrative example will now be discussed in which the anatomical model is a joint, such as a knee, shoulder, or hip. However, it should be understood that the model could represent various other aspects of the bony anatomy or soft tissue. Potential imaging modalities utilized for creation of an anatomical model may include MRI, CT, X-ray, DEXA, PET, ultrasound, etc. As discussed, the anatomical model may be subsequently subdivided or partitioned into a number of discrete volumes as shown in the figures. Division of the model surfaces creates a library of similarly sub-divided bone shapes. Each of the segments in the model will have a characteristic shape with transition to neighboring segments.

Figure 7:
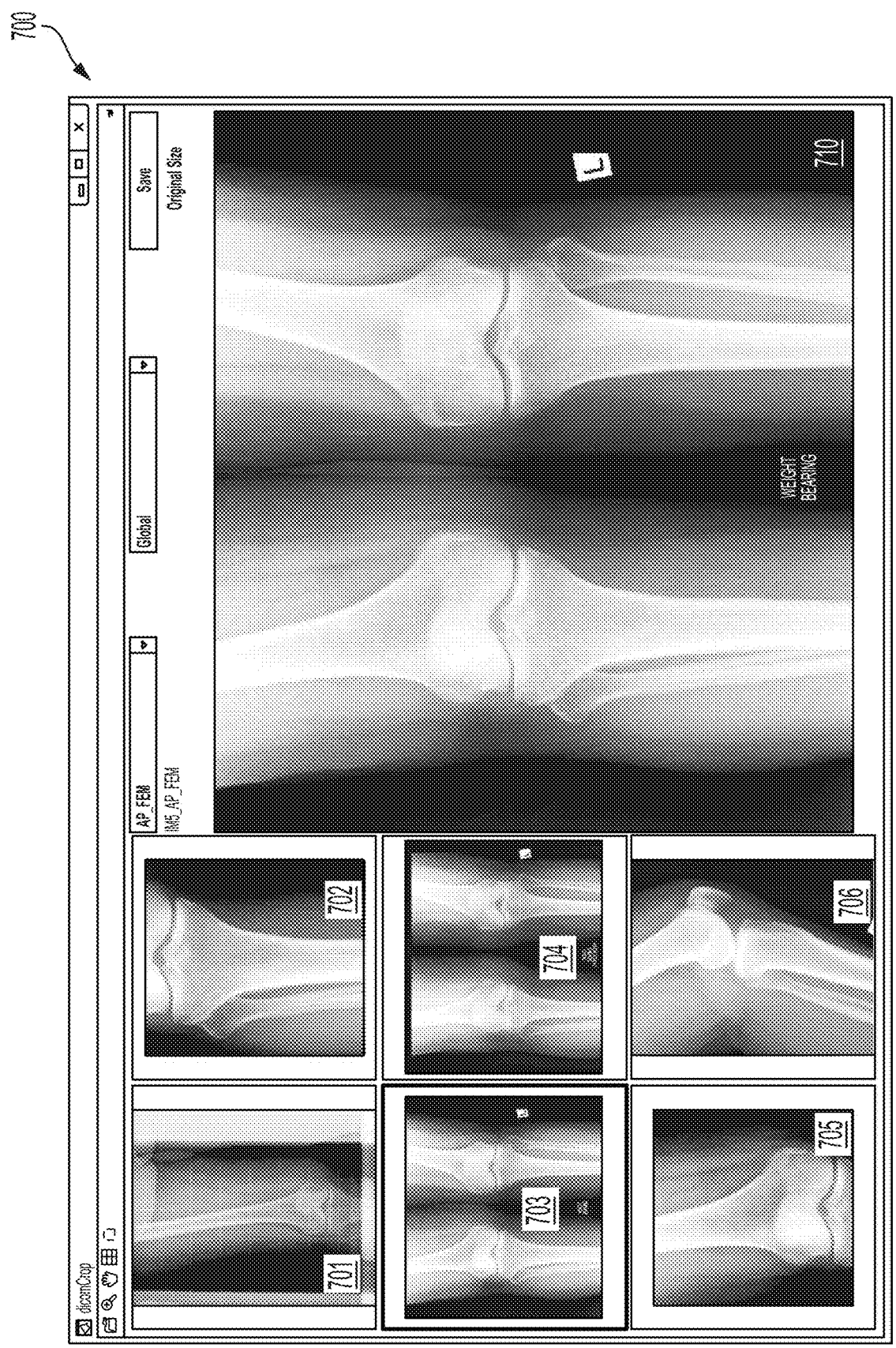
FIG. 7 depicts another illustrative example of one or more 2D medical images in accordance with an embodiment.

It should be understood that although FIGS. 6-15 depict a user interface in which the images are displayed for viewing and/or editing, no user interface or display is required. Rather, some embodiments may be fully automated and require no human intervention or adjustment. FIGS. 6A and 6B illustrate example 2D medical images received by a disclosed system. As shown, FIG. 6A is an anterior-posterior image of the right knee of a patient while standing (i.e., load bearing). FIG. 6B shows a lateral image of the same knee. It should be understood that additional images (e.g., a standing lateral oblique) may also be present and that FIGS. 6A and 6B are merely exemplary. FIG. 7 shows an illustrative display 700, which comprises various additional 2D patient images 701, 702, 703, 704, 705, and 706, wherein image 703 is selected for display in window 710.

Figure 8:
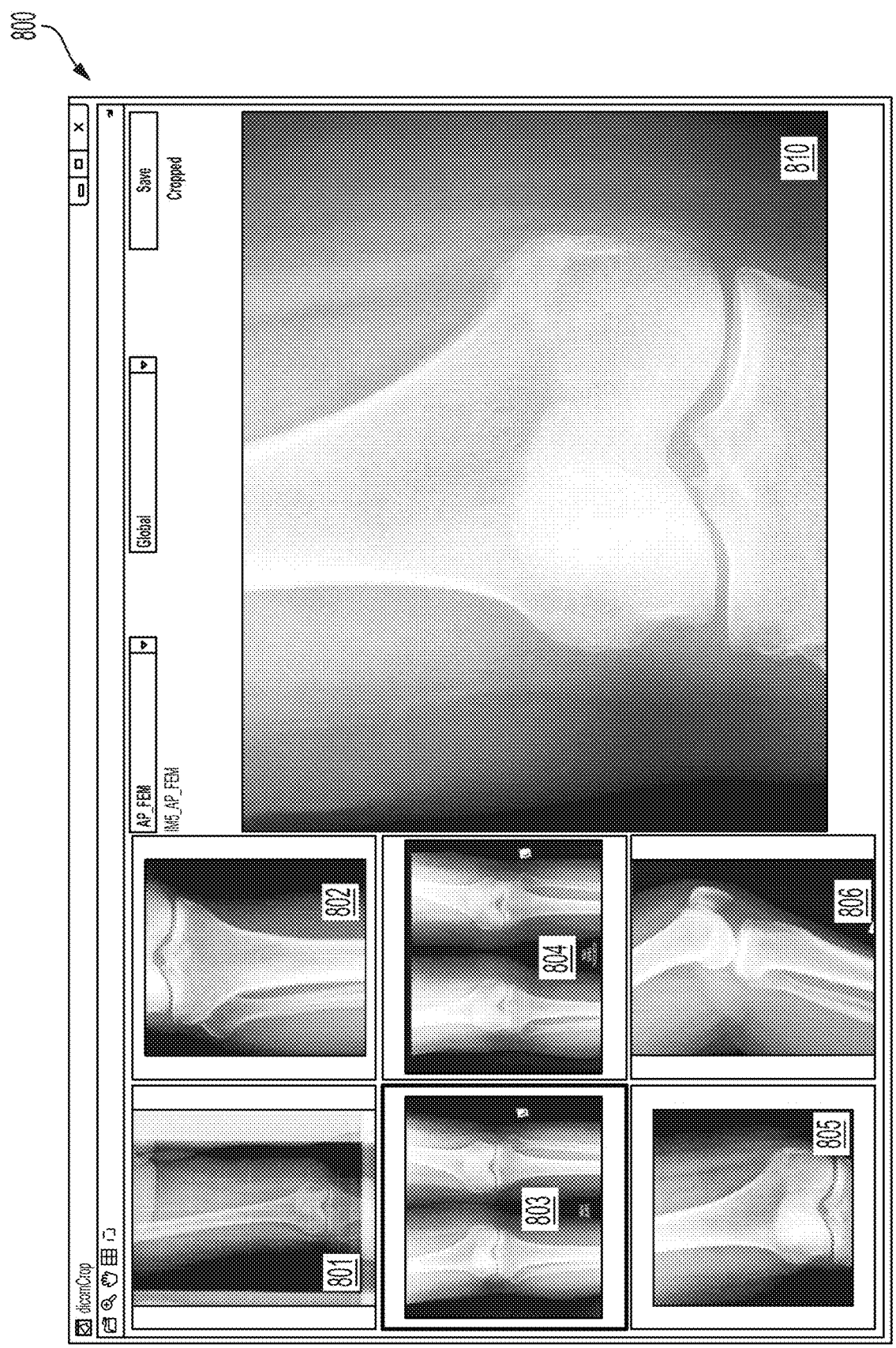
FIG. 8 depicts another illustrative example of one or more 2D medical images in accordance with an embodiment.
Figure 9:
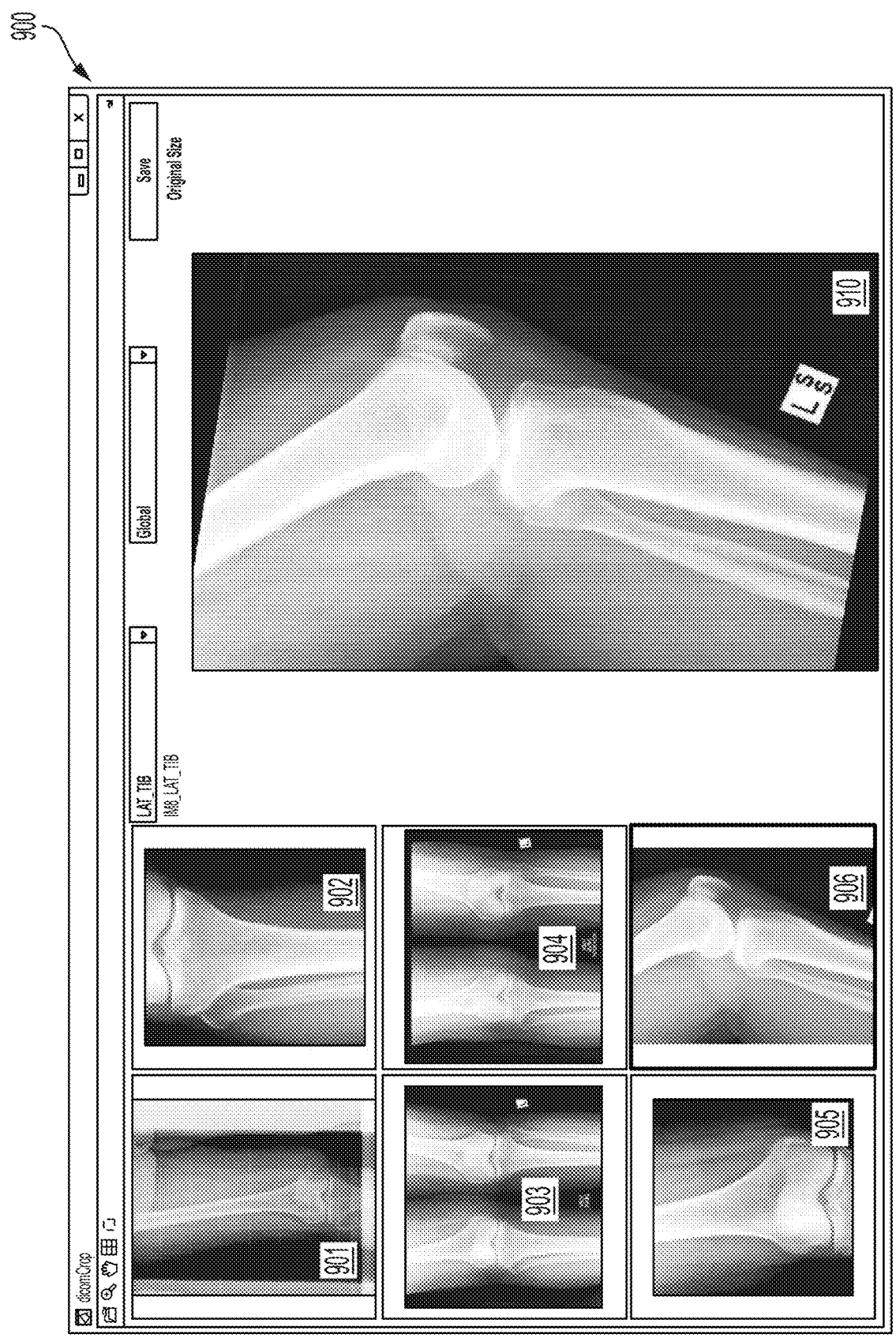
FIG. 9 depicts another illustrative example of one or more 2D medical images in accordance with an embodiment.
Figure 10:
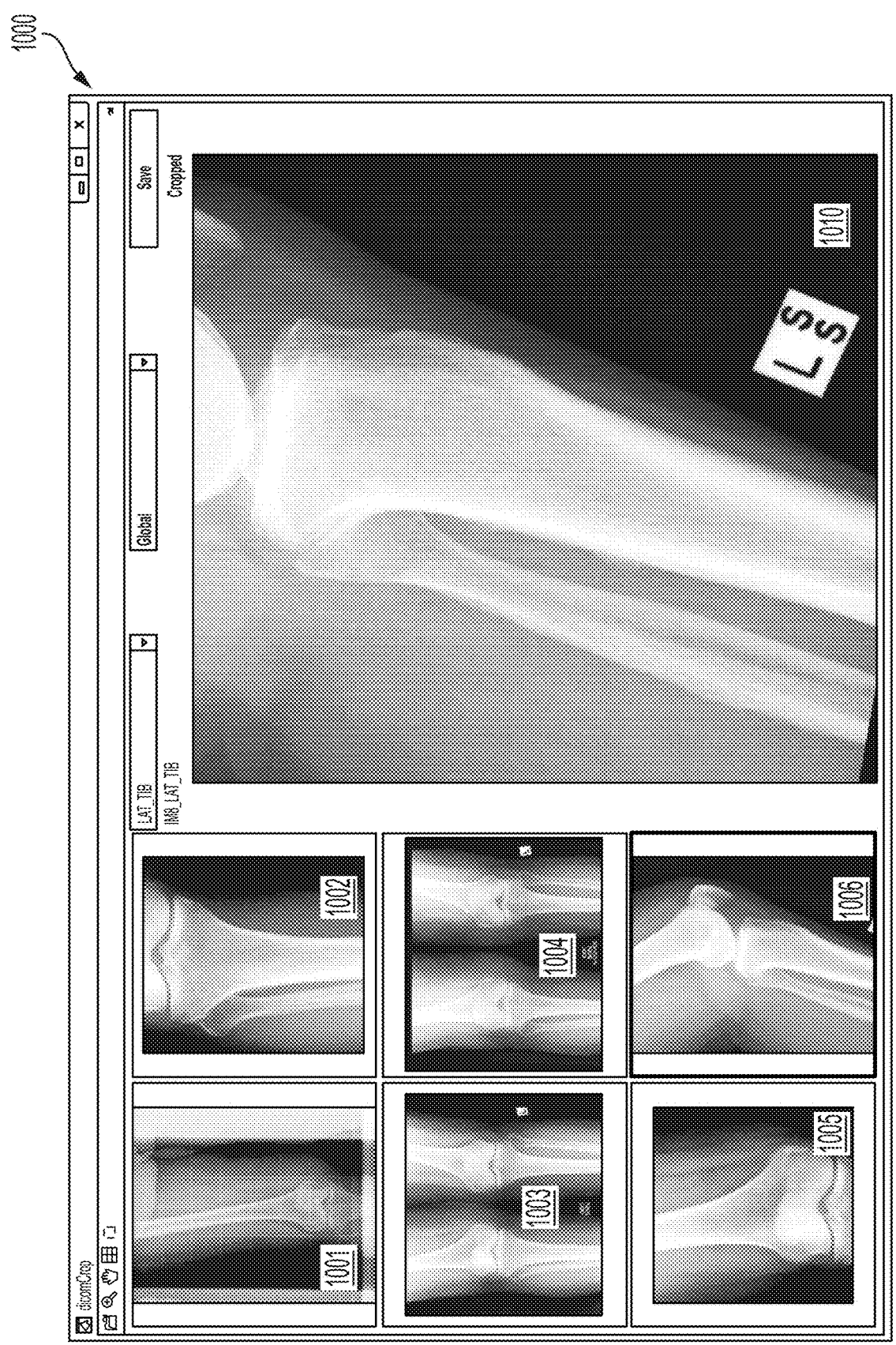
FIG. 10 depicts another illustrative example of one or more 2D medical images in accordance with an embodiment.

Referring now to FIG. 8, a user interface 800 is shown in which a selected FIG. 803 has been altered. More particularly, the image 810 has been enlarged to focus on the knee joint and has been cropped to enhance image analysis and placement of the plurality of points (e.g., K15 points, adaptively or CAD derived points, etc.). In FIG. 9, a new image 906 of the joint has been selected in the user interface 900 for display in display window 910. Similar to FIG. 8, FIG. 10 shows a user interface 1000 with an altered or modified view 1010 of the selected image 1006. Thus, as discussed herein, various processing (e.g., zooming, cropping, rotating, etc.) may be needed in order to best enhance image analysis by a user.

Figure 11B:
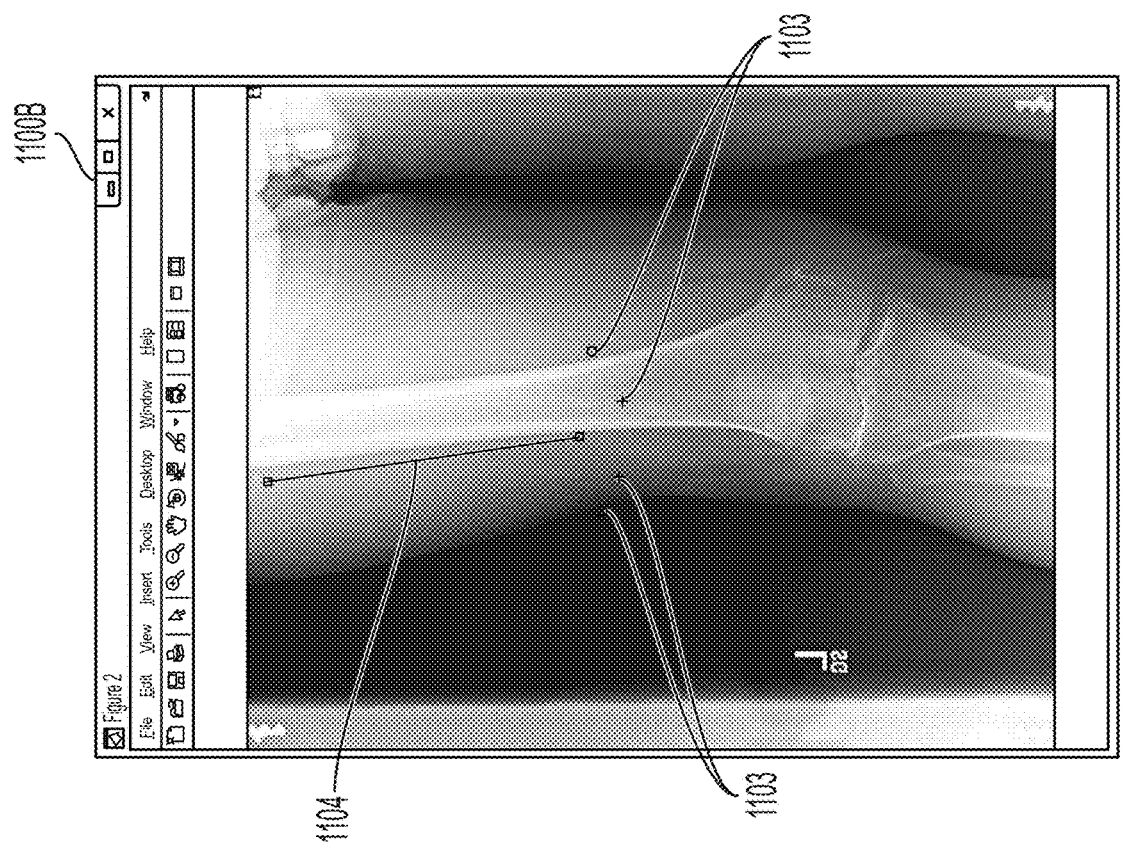
FIG. 11B depicts another illustrative example of one or more 2D medical images in accordance with an embodiment.
Figure 11A:
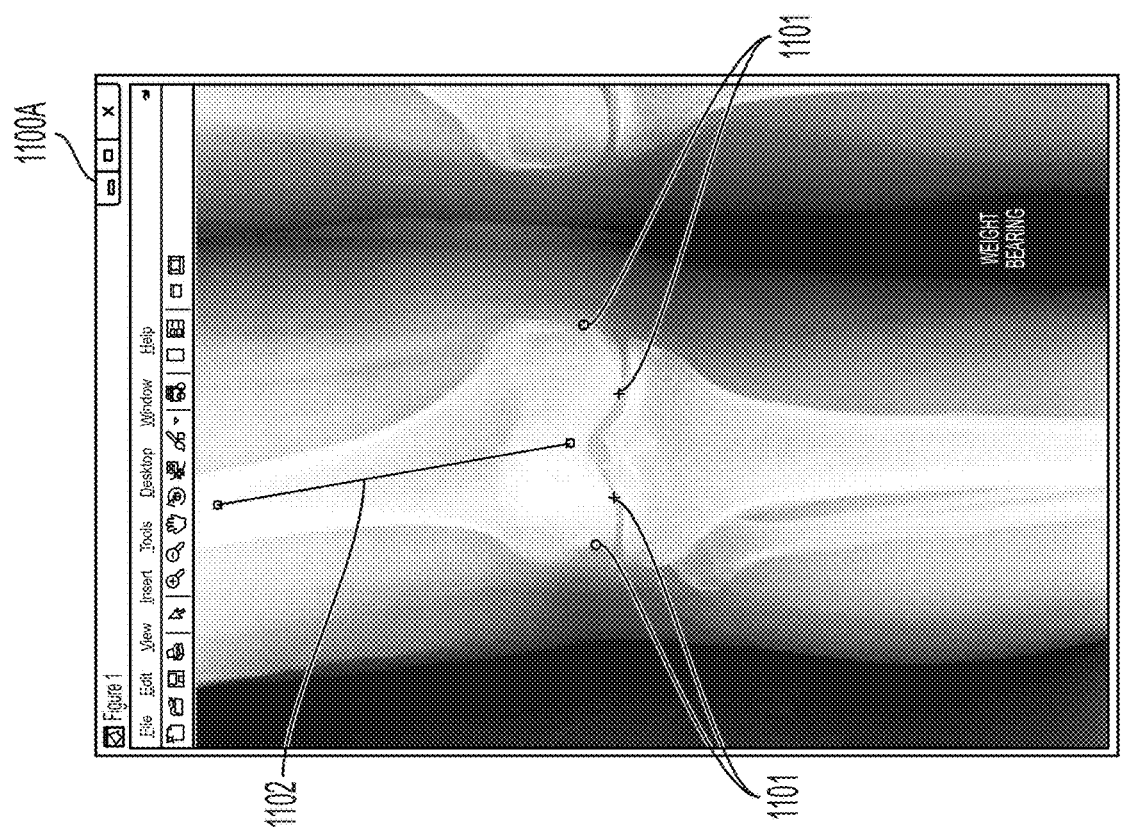
FIG. 11A depicts another illustrative example of one or more 2D medical images in accordance with an embodiment.

In FIGS. 11A and 111B, an example of the image analysis is shown. In some embodiments, a historical medical image (i.e., example femur) 1100A may be identified as being roughly similar to a received 2D image (i.e., femur under test) 1100B. Accordingly, as discussed herein, a plurality of points (e.g., four) K15 points 1101 may be identified in the historical medical image 1100A. Additionally, in some embodiments, an anatomical line 1102 may also be present. Although the image 1100B in FIG. 11B was processed, the image may still not be properly aligned with the K15 points 1104 and the anatomical line 1102, which are designed to replicate the points and line of FIG. 11A (i.e., the historical image).

Figure 12B:
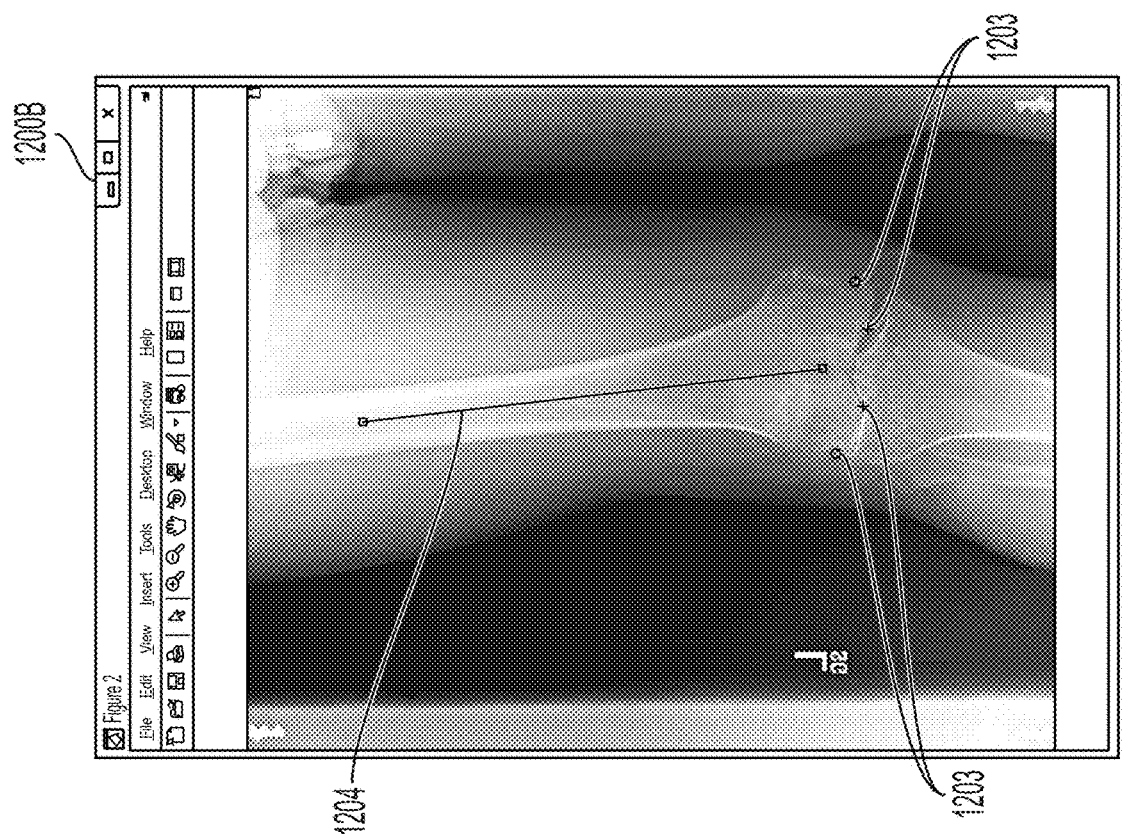
FIG. 12B depicts another illustrative example of one or more 2D medical images in accordance with an embodiment.
Figure 12A:
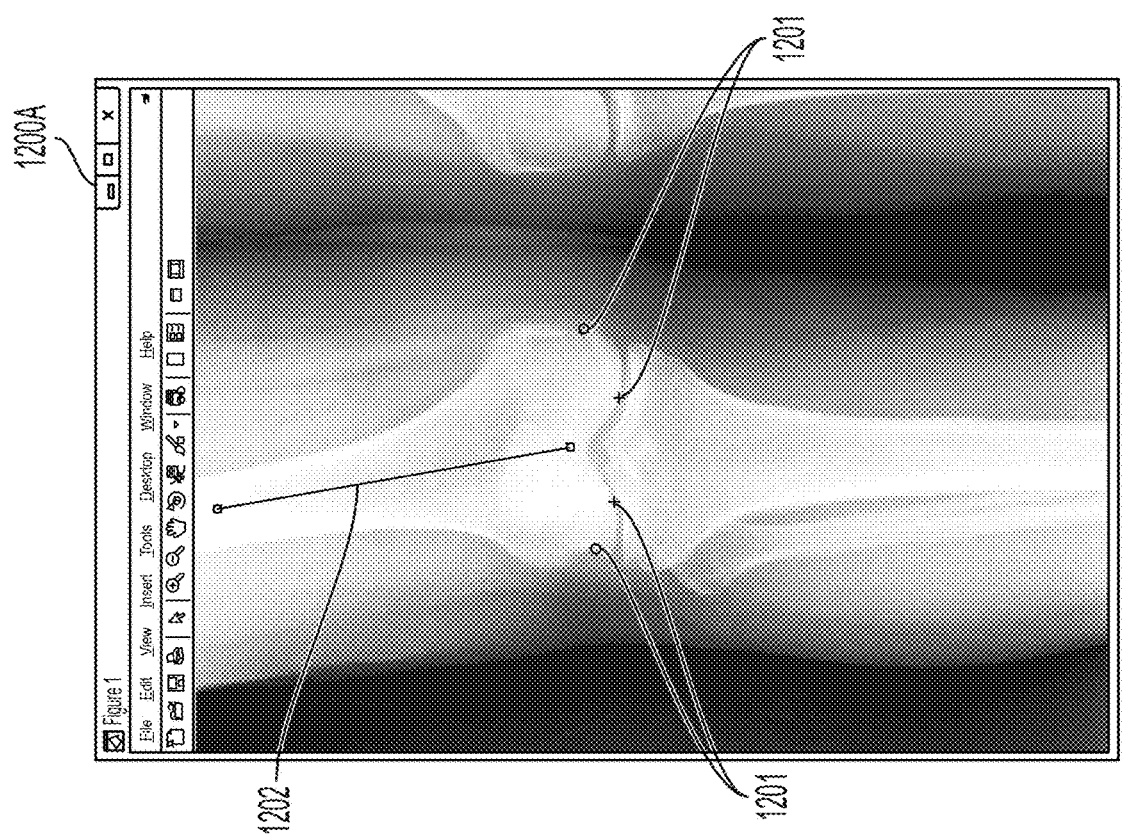
FIG. 12A depicts another illustrative example of one or more 2D medical images in accordance with an embodiment.

In an embodiment, an accurate corresponding point 1103 may be located or identified for each point 1101. FIG. 12 depicts the user interface after such correction has been performed. As such, the plurality of points 1201 and 1203 and the anatomical alignment lines 1202 and 1204 can now be directly compared to verify the accuracy and best fit of the selected historical image 1200A to the test image 1200B.

Figure 13:
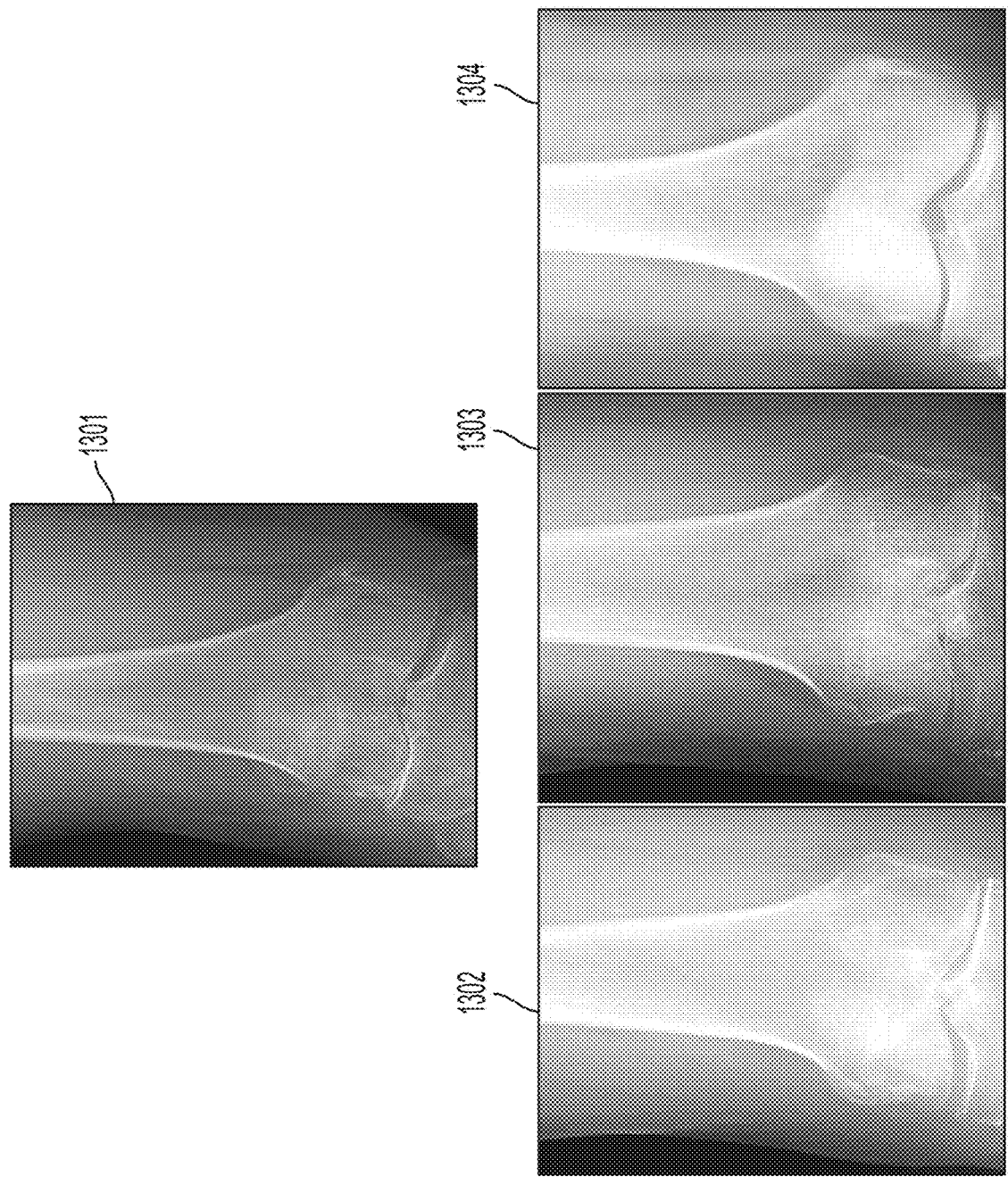
FIG. 13 depicts another illustrative example of one or more 2D medical images in accordance with an embodiment.
Figure 14:
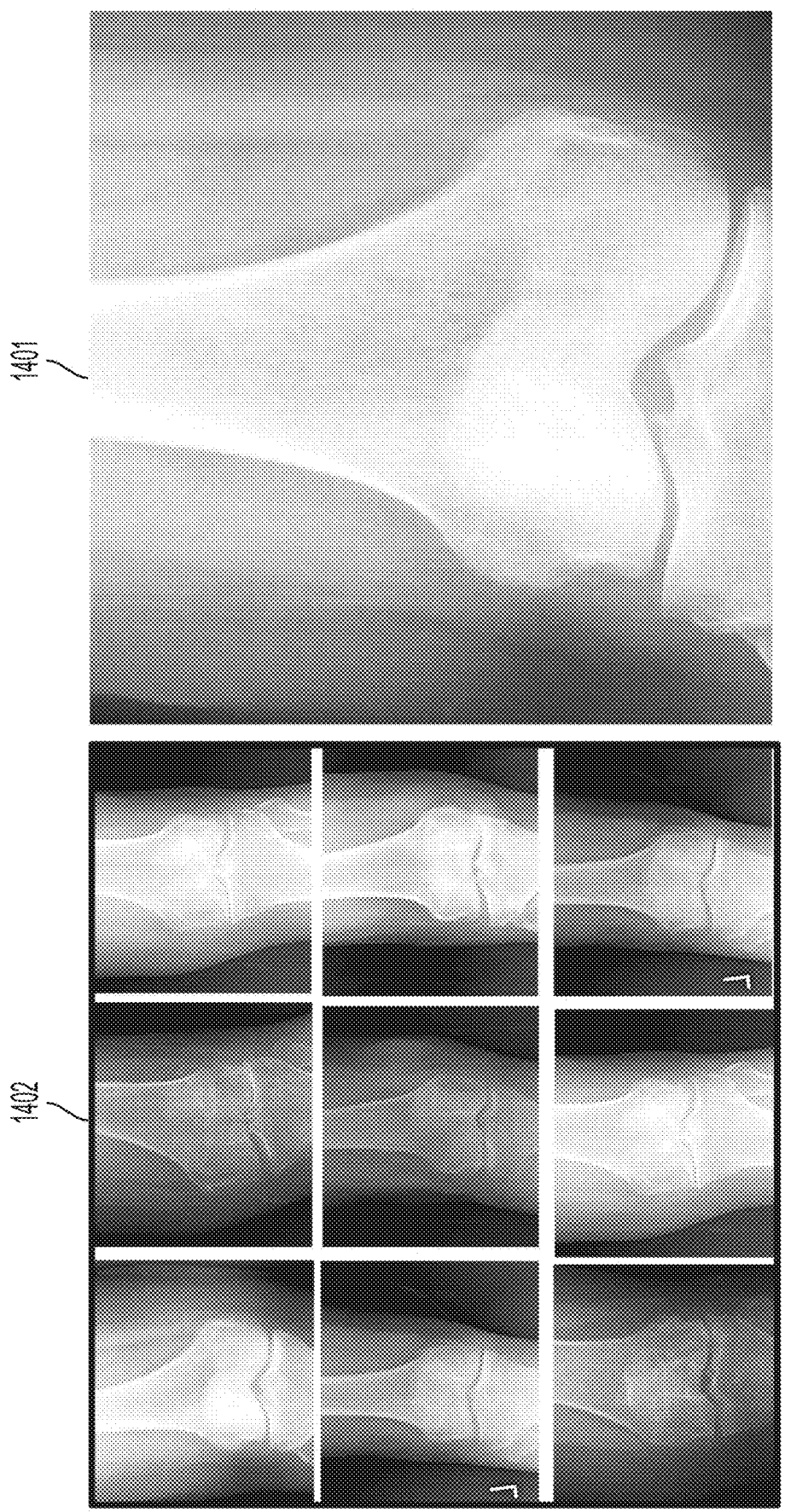
FIG. 14 depicts another illustrative example of one or more 2D medical images in accordance with an embodiment.

Although, the points 1201/1203 and the lines 1202/1204 may appear to be similar, additional 2D images may also be considered as viable candidates. As shown in FIG. 13, a plurality of potential matches 1302, 1303, and 1304 to the test case 1301 may be identified. In a further embodiment, all of the historical images, as well as the test image, may be further modified to select a correct orientation (e.g., using a toggle method, progressive refinement method, or augmented with stereolithography). In some embodiments, additional potential matches may be further identified based on known similarities within the historical library. In other words, once a plurality of potential candidate sets are determined, an embodiment may use a statistical analysis method to identify additional candidates based solely on already identified historical images 1302-1304. As shown in FIG. 14, additional potential candidates 1402 may be identified.

Figure 15:
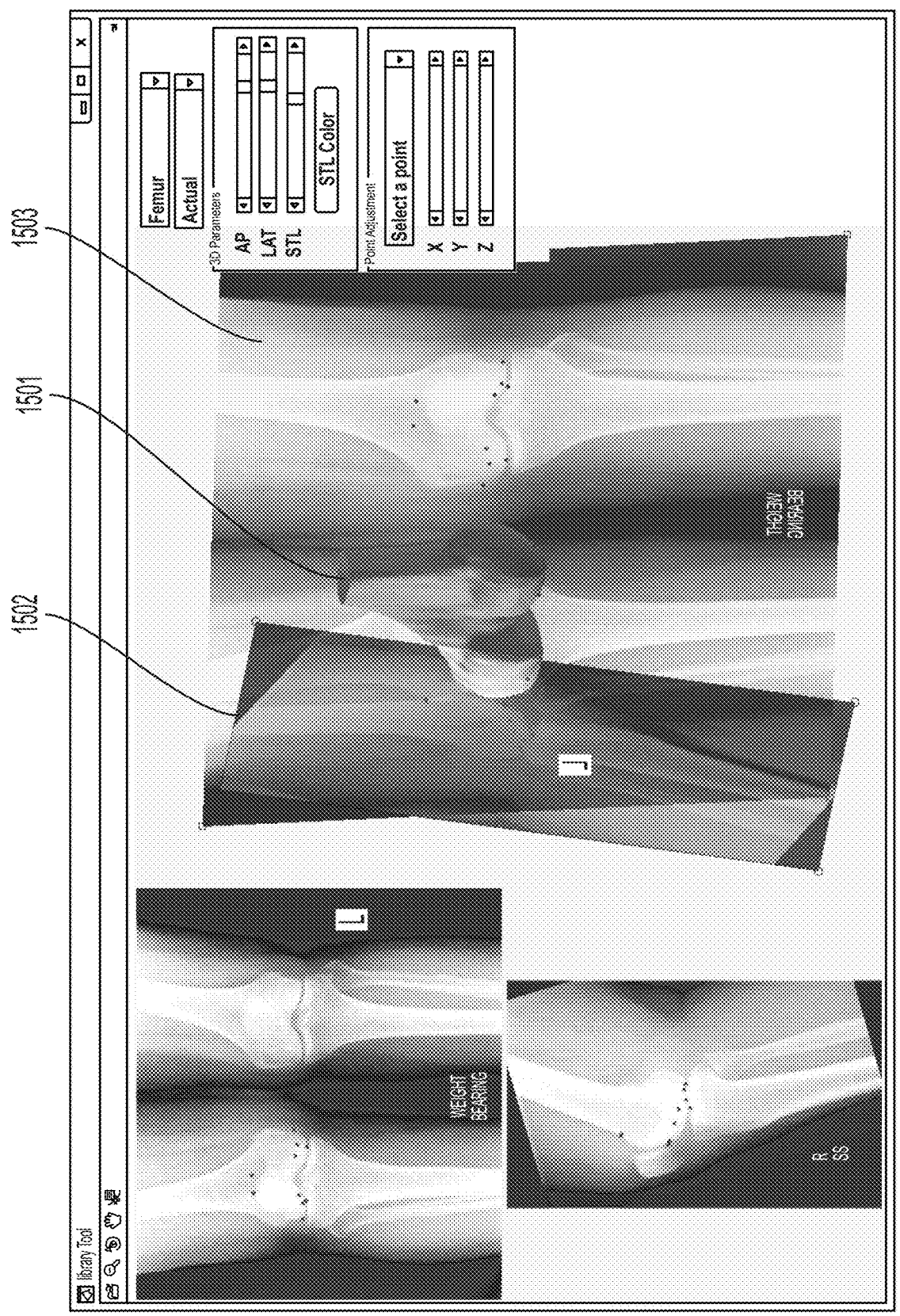
FIG. 15 depicts an illustrative example of one or more 2D medical images overlaid with a generated 3D model in accordance with an embodiment.

Referring now to FIG. 15, an example user interface is shown in which each area associated with a point (e.g., K15 points) has been matched to a level that exceeds a determined threshold. Thus, an initial or rough 3D model 1501 may be created. In some embodiments, the points may be projected onto the 3D bone where they intersect with the surface.

Moreover, in some embodiments, the original 2D images 1502 and 1503 may be overlaid, or super-imposed, on the newly created 3D model to enable a user to move the 3D model relative to the 2D images and ensure that no major errors are present. In some embodiments, the 3D model may remain stationary, and the 2D images may be moved in relation to the 3D model. In a further embodiment, the movement of the 2D or 3D images may be automated, and potential problem areas may be identified autonomously or automatically. In another embodiment, the 2D images may have a known position relative to each other, such that, for example, 2D images 1502 and 1503 may be placed in the proper orientation and angle relative to each other.

Figure 17:
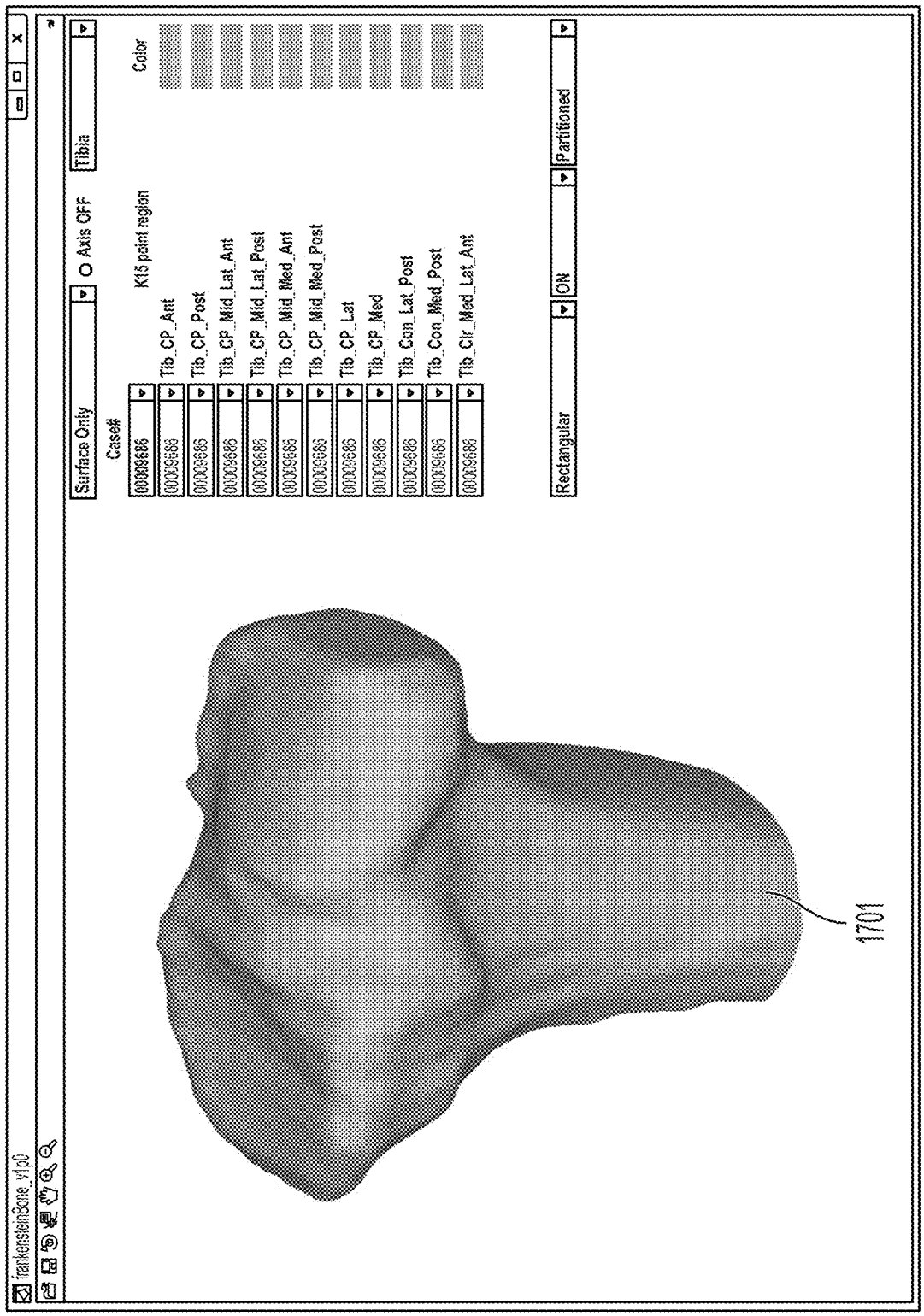
FIG. 17 depicts another illustrative example of a generated 3D model in accordance with an embodiment.

As shown in FIG. 16, once the best-matching historical images are selected for each sub-section of bone, each portion 1601, 1602, 1603 . . . 1609 may be combined together. As shown, each point region 1610 may be identified by anatomic landmark (e.g., CP_Ant, CP_Post, CP_Mid_Lat_Ant, etc.) and historical case number 1611. Once all of the sub-sections are combined, additional fine tuning adjustments may be made to ensure that no deformities or irregularities exist at each intersection of the two sub-sections. Thus, through a normalization process the 3D model may be converted from multiple sub-sections into a single 3D model 1701, such as that shown in FIG. 17.

In another embodiment, the transition region (e.g., seams) between sub-sections, and therefore the net shape of the bone model, may be governed by a spatial mapping between the points (e.g., K15 points), surface tangencies of the segments, pixel/voxel grayscale values of image data, edge detection values between pixels/voxels, models/curves that are representative of the segment surfaces, or some combination thereof. In a further embodiment, the spatial mapping may be provided as inputs to one or more of deep learning or machine learning techniques, including the use of convolutional neural networks. In such an embodiment, a neural network may be trained using various image data including MRI scans and MRI-derived 3D models that have been parameterized with control points (e.g., K15 points) and a corresponding correlation matrix, as well as 2D X-ray data.

Figure 20:
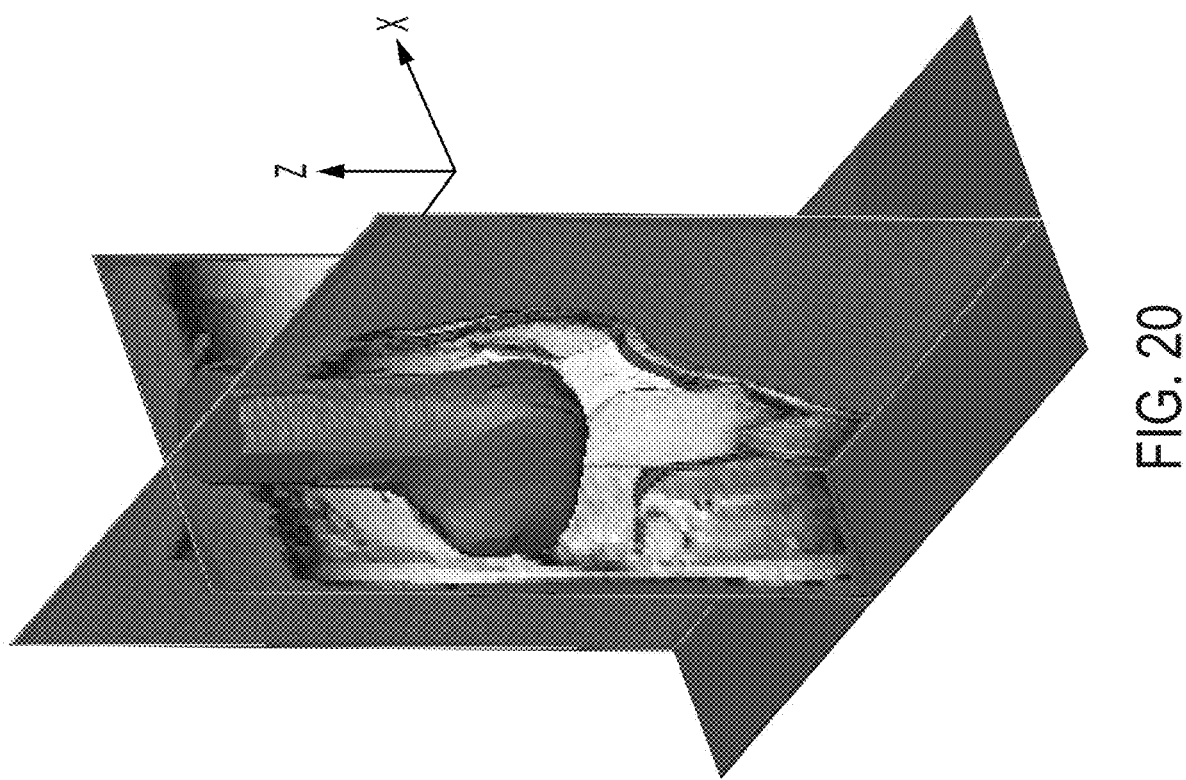
FIG. 20 depicts another illustrative example of a generated 3D model overlaid on the registered 2D images in accordance with an embodiment

As an additional example, a patient scheduled for total knee replacement has received X-ray imaging of the affected knee. As discussed herein, complementary views of X-ray images (e.g., anterior-posterior images, lateral images, or two images that are roughly about 800 to 100° (i.e., normal or perpendicular) to each other) of the joint may be captured and sent to an imaging center via a predetermined data transfer protocol. At the imaging center, the X-ray images may be registered to one another by either manual or automated techniques described herein. An anatomical model of the bone that exhibits a coarse correspondence to the X-ray images (e.g., a coarse model) may be overlaid on the registered 2D images as shown in FIG. 20. In this example, the coarse model is an anatomical model of bone or a portion of bone that is selected from a library of previously segmented bone models.

In some example embodiments, the coarse model may be specified based on a series of landmarks that correspond to features identified in the 2D X-ray images, and an imaging technician may manipulate one or more control points (e.g., K15 points) to improve upon the correspondence of the model to the 2D images. Software may be used to produce a model containing various bone segments from the input library and to create segment transitions based on predetermined correlations and interpolation operations. In a further embodiment, the 3D model may subsequently be used to model and manufacture a variable bone coupler for the patient's knee replacement surgery.

As discussed herein, a coarse bone model may be based on a selection from a collection of actual bone geometries and not a statistical model. Thus, in some embodiments, landmarks on the bones may be used as a means of selecting the bone that most resembles the bone depicted by the X-rays. Those having ordinary skill in the art would understand that landmarks may be, for example, epicondyles, the tibial spine, Whiteside's line, the trans-epicondylar axis, tibial tuberosity, a mechanical axis, an anatomic axis, the medial malleolus, or an adductor tubercle. Alternatively, a statistical model may be used. However, a statistical model may have the drawback of overly smoothing the bone.

As discussed, the coarse model may only be a first-order solution or a starting point. Thus, additional fine-tuning may be performed. In some embodiments, a statistical approach that does not include a mean-bone statistic may be used. Generally, a closed-form optimization that leverages input data (e.g. points on an initial X-ray) and matches it to the library of solutions may make use of statistics from the historical library, at least to aid in finding a maximally likely selection. Thus, statistics (e.g., statistical analysis of the signature or thumbprint of the bone) are used in certain embodiments.

Figure 18:
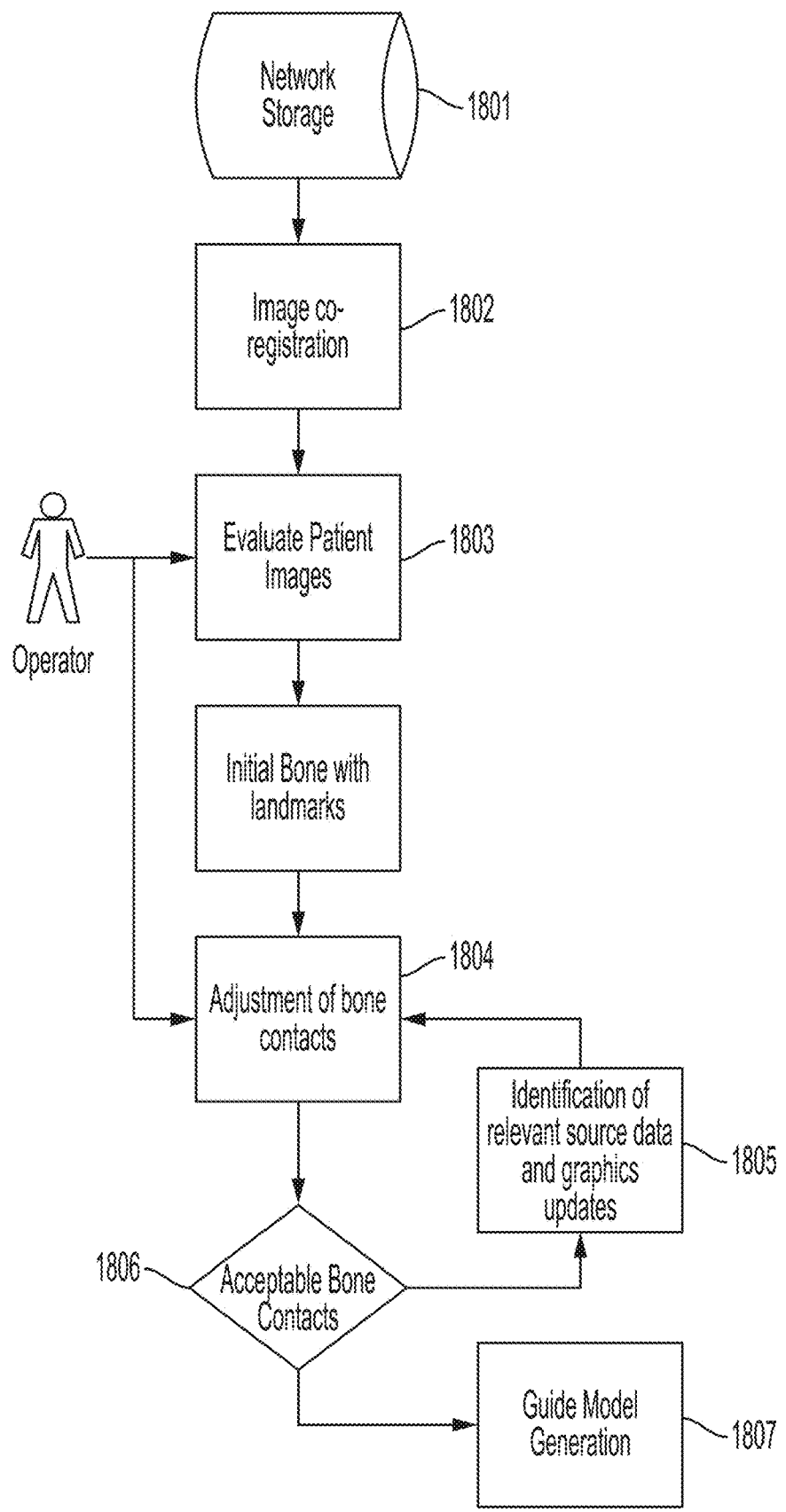
FIG. 18 depicts an illustrative method for guide model generation via 2D to 3D intuition.

FIG. 18 depicts a flowchart for a process of generating the variable bone coupler via 2D to 3D intuition. In step 1801, 2D images and a coarse model are retrieved from network storage. In step 1802, the 2D images and the coarse model are registered in a coordinate system. In step 1803, a user evaluates the coarse model in comparison to the 2D images, and manipulates the coarse model to align specific landmarks of the 2D images. In step 1804, the user manipulates bone contact locations (e.g., adaptive points, visual handles, etc.) of the coarse model. In step 1805, the user iteratively identifies relevant source data and updates the graphical representation. In step 1806, the user determines whether the bone contact locations are acceptable. In step 1807, the user outputs the guide model.

The distinguishing technical effect of the disclosed embodiments is to provide the ability to quickly create a 3D representation of a patient's joint based on 2D X-ray data without time-consuming or user-intensive operations. Accordingly, the proposed embodiments may begin with a coarse model that is the result of training, using a rich data-set of MRI and X-ray scans. In addition, the process may not be fully automated (i.e., it may still require fine tuning adjustments and approval from an imaging expert). These features allow for a bifurcated delivery model that supports design and manufacture of the guides in both clinical and off-site settings, as presented in FIG. 19.

Figure 19:
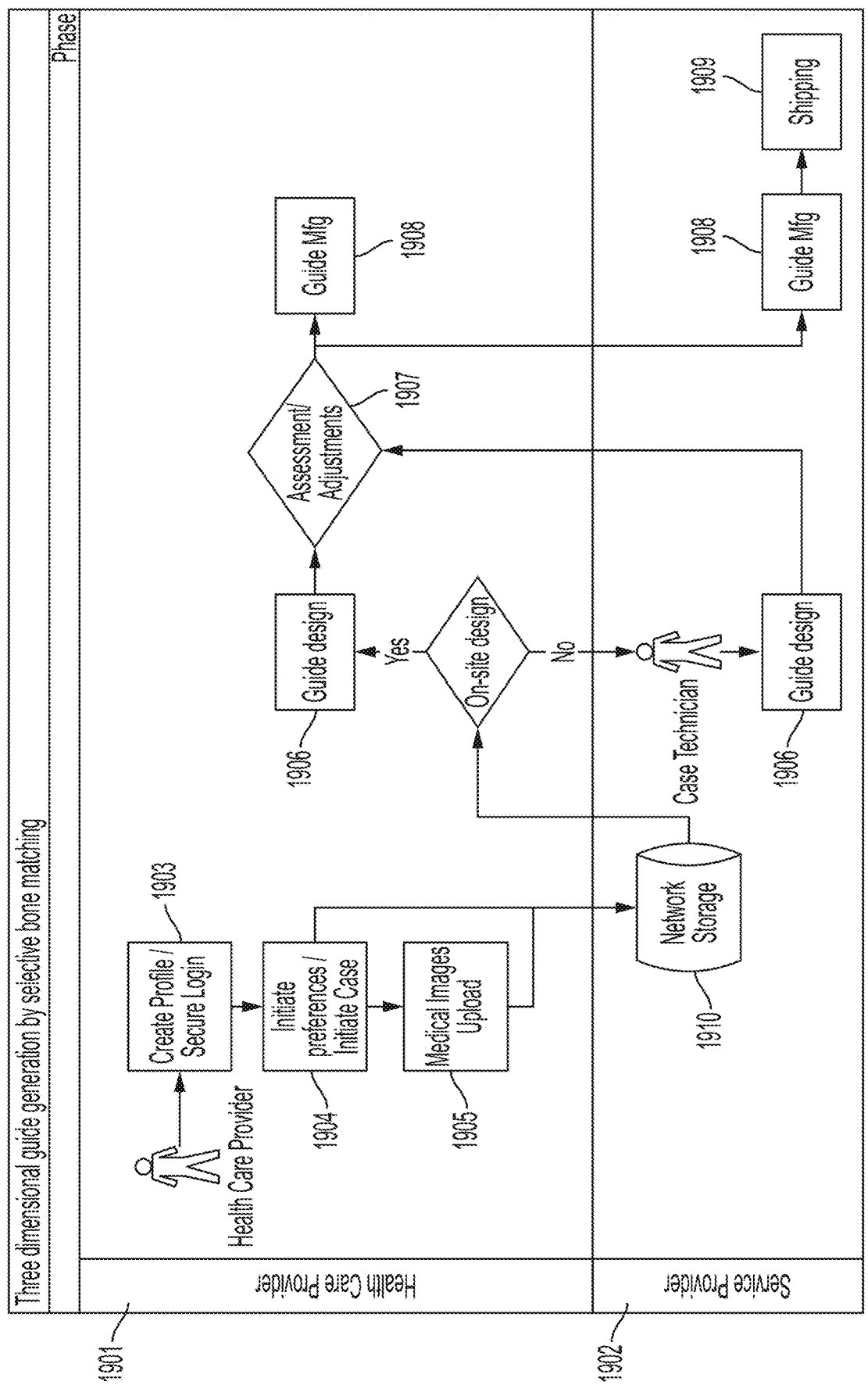
FIG. 19 depicts an illustrative method for surgical guide design and manufacture showing both service-based and HCP-driven models.

FIG. 19 depicts the generation of the variable bone coupler by selective bone matching surgical guide design and manufacture strategy showing both service-based 1902 and health care provider (HCP) driven models 1901. In FIG. 19, certain operations may be performed by a health care provider 1901, such as a surgeon, nurse, hospital, or surgical center, while other operations may be performed by a service provider 1902, such as a manufacturer or engineering design firm. Those of ordinary skill in the art would understand that there may be a plurality of HCPs and/or service providers. In the depicted embodiment, an HCP logs into a system 1903 and creates a patient profile 1904 to initiate a case. In some embodiments, the HCP also may designate initial preferences for a particular patient 1904. As examples, initial preferences may include a surgical approach, desired standard instruments, a desired implant type, or the like. The HCP may upload the patient's X-rays 1905 to a network storage device 1910. The HCP also may upload the patient profile (not shown). Although the network storage device 1910 is shown as being located within the service provider's 1902 domain, it should be understood that the HCP 1907 may alternatively control the network storage device 1910.

In some embodiments, a case technician may retrieve information from the network storage device 1910 and design 1906 and build the variable bone coupler. The variable bone coupler is iteratively assessed and adjusted as needed. The variable bone coupler may then be manufactured 1908. In some embodiments, the variable bone coupler may be 3D printed. In some embodiments, the variable bone coupler may be manufactured 1908 by the HCP 1901. Alternatively, the variable bone coupler may be manufactured 1908 by the service provider 1902. If the guide is manufactured by the service provider 1902, then the variable bone coupler may be shipped 1909 to the HCP 1901.

The variable bone coupler resulting from this process may be designed to interface with existing instruments and locate them with a series of discrete contact features (i.e., instead of a congruent, glove-like fit). As a result, the variable bone coupler may be designed by estimating surgically pertinent aspects of the bone, instead of aiming for a comprehensive recreation of the entire bone. In a further embodiment, a patient-matched stylus may be created in which multiple positioned points (e.g., spring loaded and/or adjustable) are present.

It should be noted that any one of the previously described automated techniques could produce several "close" solutions from which one or more users select the best representation based on their experience or training in radiological imaging. In a further alternative embodiment, a user may manipulate characteristic curves associated with each bone segment shape instead of control points. Such an embodiment could be facilitated using both automated and semi-automated techniques.

As further discussed herein, an embodiment may allow for the creation of one or more 3D models from 2D image data. 2D image data can be acquired with less cost than volumetric image data such as MRI or CT images. It should be understood, that although the term "3D image data" is primarily used herein, that the models may include one or more of CAD, IGES, STL, VRML, DXF, OBJ, or similar file/application types. In some embodiments, as discussed herein, it may be possible, during the subdivision of an anatomical model, to create an extremely large library of bone shapes (i.e., more than are generally available with a database of standard non-permutable bone shapes using a standard statistical shape model (SSM) technique). Accordingly, as discussed herein, some embodiments may utilize a semi-automated system. In some embodiments, the semi-automated system may receive additional input from a user (e.g., a medical imaging expert who provides quality control), thereby leveraging the medical expertise of the user to simplify the computational requirements of the system. In some embodiments, the system may not receive any additional input from a user.

Figure 21:
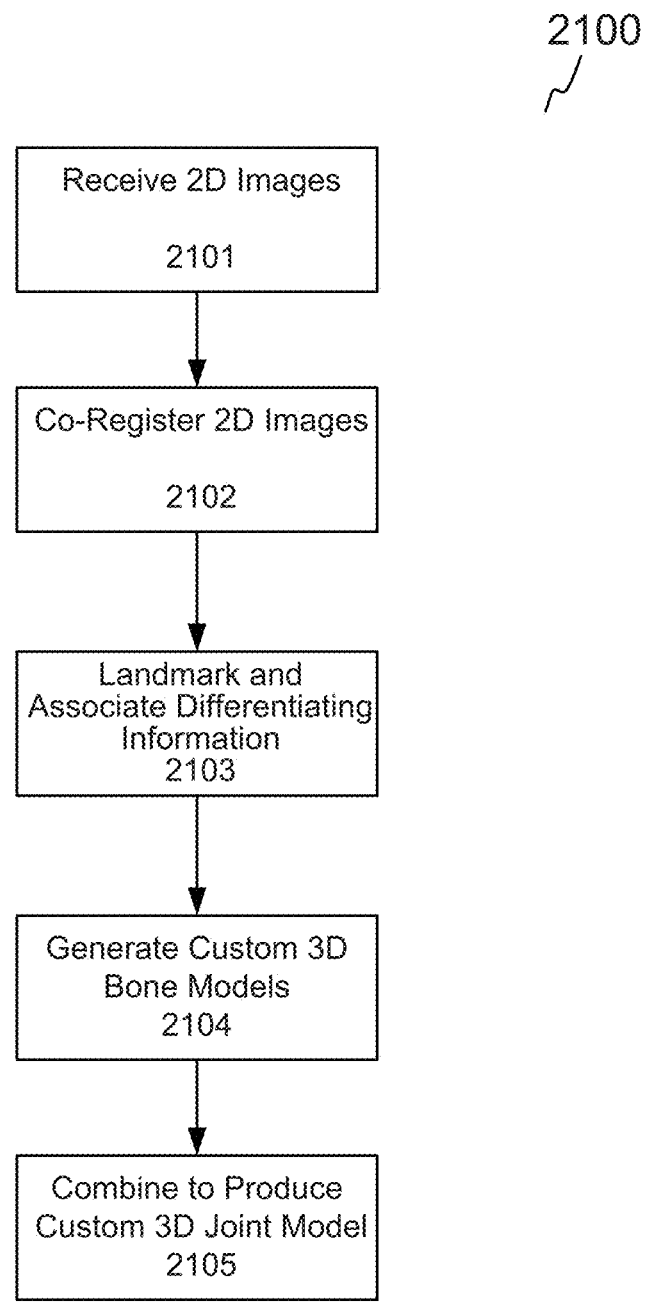
FIG. 21 depicts an illustrative method of producing a custom three-dimensional model of a joint in accordance with an embodiment.

Referring now to FIG. 21, an example embodiment 2100 is shown related to the creation of a 3D model of at least a portion of a patient's anatomy from 2D image data. Thus, in some embodiments, a system may receive 2101 a plurality of 2D images (e.g., projection radiography, fluoroscopy, tomography, echocardiography, ultrasound, or any known or future 2D image format) that capture at least a portion of a patient's bony anatomy (e.g., one or more bones, or bone segments, forming a joint or region of interest). In some embodiments, the user (e.g., a surgeon or medical professional) may utilize a graphical user interface (GUI) to upload one or more 2D images from either a local or a remote storage device. The GUI may be implemented on a variety of platforms (including but not limited to a computer, a tablet, a smartphone or other mobile device) and may be displayed on a variety of means (including but not limited to a display, a headset, a medical image viewer, and a picture archival and communication system (PACS)). In further embodiments, the 2D images may be downloaded directly, or autonomously, by the system from a secondary device, including, but not limited to, a computer, a mobile device, a tablet, a server, a remote database, and the like. In some instances, one or more 2D images may be transmitted by a remote device and received and stored by the system for future use. In other instances, the system may access the remote device and request the 2D images. Further, in addition to the 2D images, differentiating data associated therewith may be received as well. For example, the system may additionally acquire data including one or more properties related to the bones of the 2D image, such as dimensions, measurements, calculated properties, deformities, features, or other differentiating information as described herein. Data relating to properties of the bones may be received with the 2D images, through manual input from a user, from a database, or by other methods known to one having ordinary skill in the art.

Once received 2101, the plurality of 2D images may be co-registered 2102 to create a modified and/or composite 2D image (e.g., FIGS. 23A-23C discussed below). In some embodiments, the co-registration process 2102 may include aligning two or more 2D images to recreate one or more anatomical features of interest. As discussed herein, specifically with reference to FIGS. 23A-23C, a portion of the field of view for each of the received 2D images 2101 may overlap with a portion of the field(s) of view of adjacent (i.e., associated) 2D images. Thus, in some embodiments, these overlapping areas may be analyzed (e.g., autonomously or via human review) to enable common features to be aligned with one another and thus the plurality of 2D images may be "stitched" together to form a composite 2D image. In the embodiment depicted in FIGS. 23A-23C, multiple images are stitched together to form a composite, full-length, leg X-ray image.

In a further embodiment, the system may landmark 2103 the composite image (or at least one of the individual 2D images) and associate the landmarks and any further known differentiating information with the image(s). Landmarking 2103 may be performed by identifying one or more key points with respect to the patient anatomy (e.g., bone, joint, ligament, etc.) in order to further characterize the area of interest. The landmarks may be associated with the composite image and/or individual 2D images to serve as differentiating data in the process as further described herein. As described, landmarking 2103 may also encompass associating any additional data acquired by the system with the images in the same manner, including one or more properties related to the bones of the 2D image, such as dimensions, measurements, calculated properties, deformities, features, or other differentiating information as described herein. Data relating to properties of the bones may be received with the 2D images, through manual input from a user, from a database, or by other methods known to one having ordinary skill in the art.

In some embodiments, the key points may be related to one or more anatomical features and/or associated with a known portion, anatomical feature, or landmark. For example, in some embodiments, the one or more key points may refer to portions of the bony anatomy, locations of ligament attachment, and/or size and direction extremes (e.g., points of the Adaptive Guide VISIONAIRE system, bony landmarks, anatomic landmarks, geometric inflection points, etc.). In a further embodiment, the key points are related to features and/or associated with a portion of an anatomical feature or landmark. In additional embodiments, the key points may be associated with a subdivided segment. In additional embodiments, the key points may be obtained by intersecting projected rays of 2D image landmarks in 3D space relative to a 3D candidate bone model. In still additional embodiments, the 2D or 3D solid is divided into discrete segments such that particular segments or areas which represent the bone may be individually manipulated, as described herein.

In additional embodiments, the one or more key points may be associated with one or more certain anatomical features, such as, for example, a knee center, one or more posterior points on a patient's condyles (e.g., lateral and medial), an anterior notch point, epicondyles (e.g., lateral and medial), points along the femoral AP axis, mid planes, or intersection points, or the like. In further embodiments, a key point may identify an expected resection location or an expected position for one or more surgical tools (e.g., a cut guide, trial implant, etc.) with respect to one or more anatomical features or landmarks. In some embodiments, the key point(s) may be located on an anatomical feature or landmark. In other embodiments, one or more of the key point(s) may be located at a pre-determined offset position from the one or more features or landmarks. Accordingly, in some embodiments, key points may be associated with a feature, a landmark, or a known location (e.g., at a known vector relative to an identifiable anatomical location). Thus, it should be understood that in some embodiments each key point, or set of key points, chosen for identification may vary based on the patient anatomy (e.g., the particular joint) or the type of procedure to be performed.

Once co-registration 2102 is complete, landmarking 2103 may be performed. As discussed further herein, in some embodiments, landmarking 2103 may be performed manually (e.g., via the GUI). In other embodiments, a computing device may identify (i.e., auto-landmark) the one or more key points (e.g., based on machine learning, artificial intelligence, artificial neural networks, or the like). In some embodiments, manual adjustments may be made to the key points. In some embodiments, the set of key points that are chosen for identification may be consistently and accurately identifiable across a plurality of procedures on a plurality of patients. In some embodiments, due to the consistency and accuracy in the landmarking 2103, the system may calculate one or more properties of the bones of the patient. In other embodiments, various dimensions and/or deformities of the bones may be identified and/or calculated. For example, with respect to the knee joint, a system may calculate a varus, valgus, and/or bow angle deformity of the femur, tibia, and/or entire leg. As described, it is further contemplated that while one or more properties are calculated, landmarking 2103 may further encompass associating in the same manner any further differentiating data acquired by the system with the 2D image, including one or more properties related to the bones of the 2D image. For example, data relating to properties of the bones may be received with the 2D images, through manual input from a user, from a database, or by other methods known to one having ordinary skill in the art.

Utilizing the landmarking 2103 and any calculated properties, a custom 3D bone model may be generated 2104 for each of the plurality of patient bones. The 3D bone model(s) may then be combined to produce a custom estimated 3D model of a patient's anatomy 2105 (e.g. a joint comprising the plurality of patient bones).

While identification of key points and calculation of properties of the bones as described herein is beneficial, this step may be omitted in some embodiments. Due to the visual assistance provided by a user for alignment, the identification of key points is not required for generation of the 3D bone models. Still, key points and calculation of various properties may assist the system in more accurately estimating features of the bones and thus more accurately and efficiently providing comparable representative bones as further described below.

Figure 22:
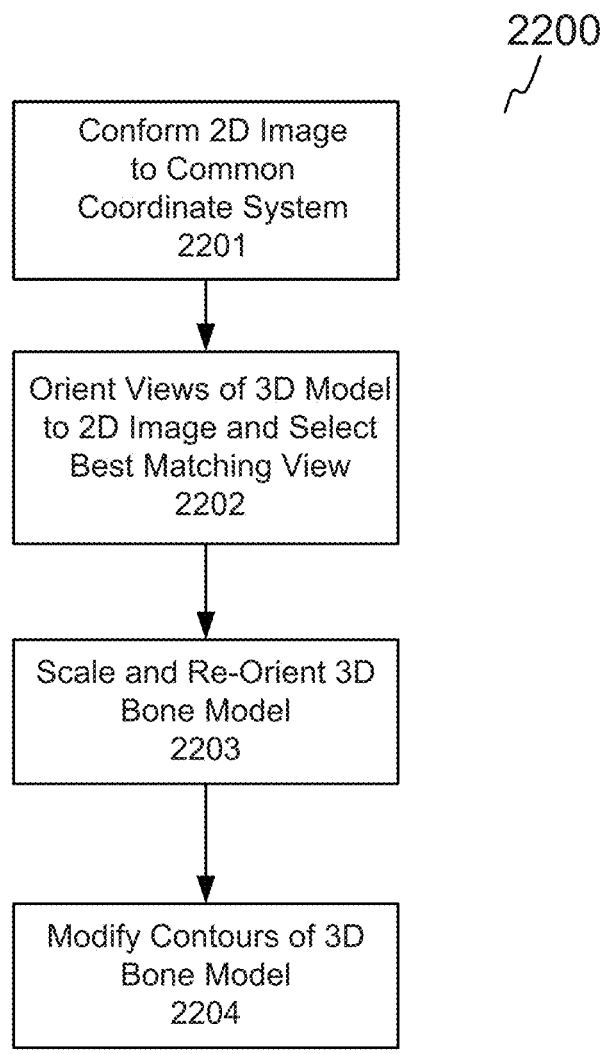
FIG. 22 depicts an illustrative method of generating a custom three-dimensional bone model in accordance with an embodiment.

Referring briefly to FIG. 22, an illustrative method for generating a custom 3D bone model 2200 for a candidate bone of the patient is shown. In some embodiments, a system performing the method may conform the candidate bone to a common, or known, coordinate system 2201 using the 2D images. Thus, in a further embodiment, a representative bone (e.g., from a library of representative bones) substantially matching the candidate bone may be presented from a plurality of views, and an ideal view may be selected 2202. The representative bone (e.g., a 3D bone model corresponding to the selected representative bone) may then be adjusted 2203, for example, by repositioning, scaling and/or re-orienting the 2D images of the bone of the patient to more closely match the 3D bone model. Alternatively, the 3D bone model may be repositioned, scaled, and/or re-oriented with respect to the 2D images to accomplish the same result. Finally, the 3D bone model may be modified 2204 by altering one or more contours to more closely match the candidate bone.

Figure 23A:
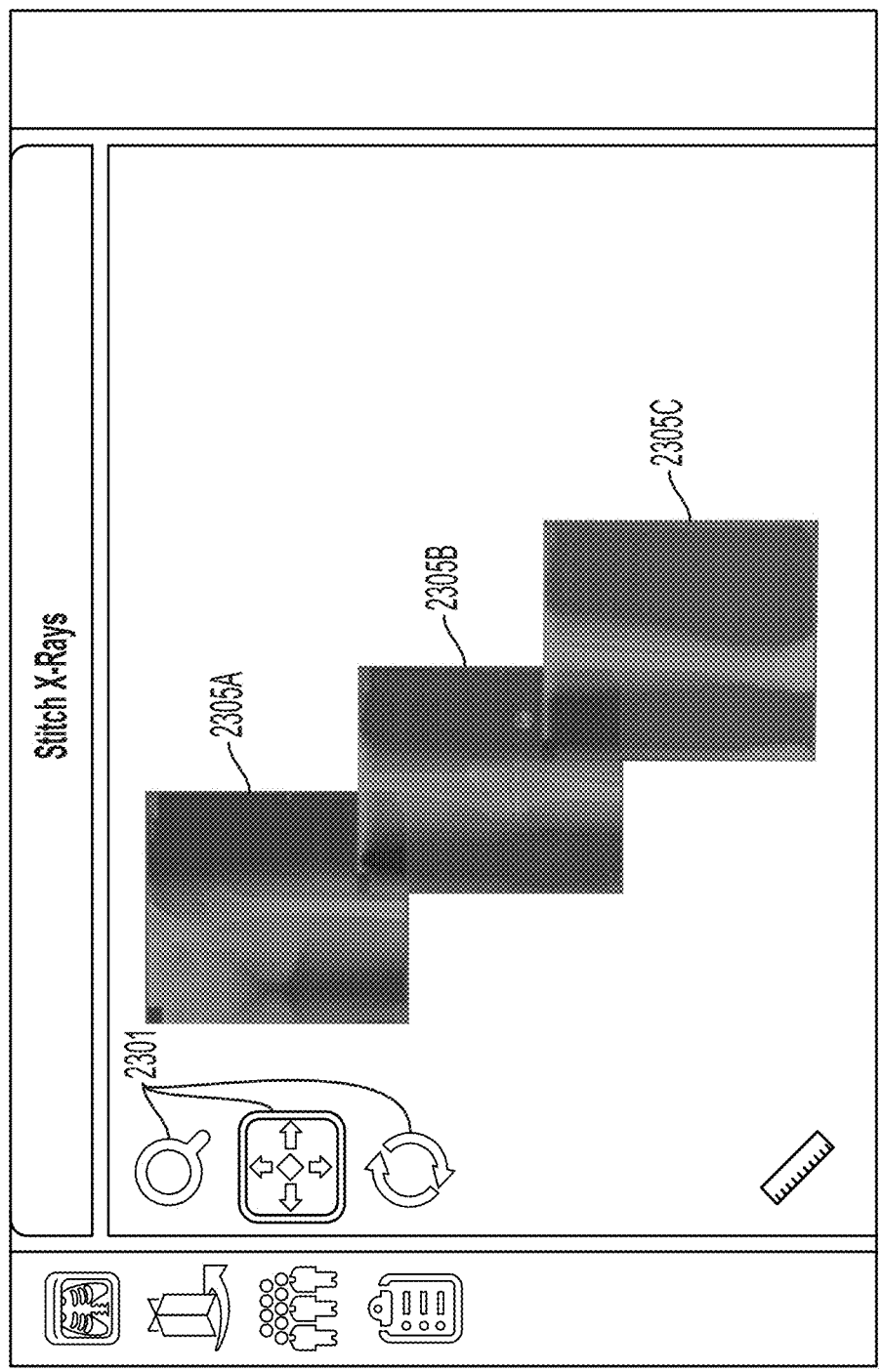
FIGS. 23A-23C depict a process of co-registering a plurality of 2D images in accordance with an embodiment.

Referring now to FIG. 23A, an illustrative example of a plurality of received 2D images are shown (i.e., 2305A, 2305B, and 2305C) as radiograph "X-ray" images. However, as discussed, various forms of 2D images are contemplated. In further embodiments, the 2D images may comprise fluoroscopy images, projectional radiographs, 2D computed tomography images, 2D echocardiography images, ultrasound images, and the like. Each of the plurality of 2D images may provide one or more sectional fields of view of a region of the patient's body, such that, in sum, the plurality of 2D images capture the entirety of the bones forming the anatomy of interest (e.g., the joint).

By way of non-limiting example, when a knee joint is the anatomy of interest, the plurality of 2D images may include a first image capturing an upper portion of a patient's femur 2305A, a second image capturing a lower portion of the femur and an upper portion of the tibia 2305B, and a third image capturing a lower portion of the tibia 2305C. Further, while a single view may be sufficient, additional views of the plurality of bones may be provided. In some embodiments, for example, images of a femur and/or a tibia may be provided from an anterior-posterior (AP) view and/or a medial-lateral (ML) view. Thus, embodiments may have a corresponding 2D image from a second view for each of the 2D images shown. In other embodiments, only some of the 2D images from a first view may have a corresponding 2D image from a second view.

Figure 23B:
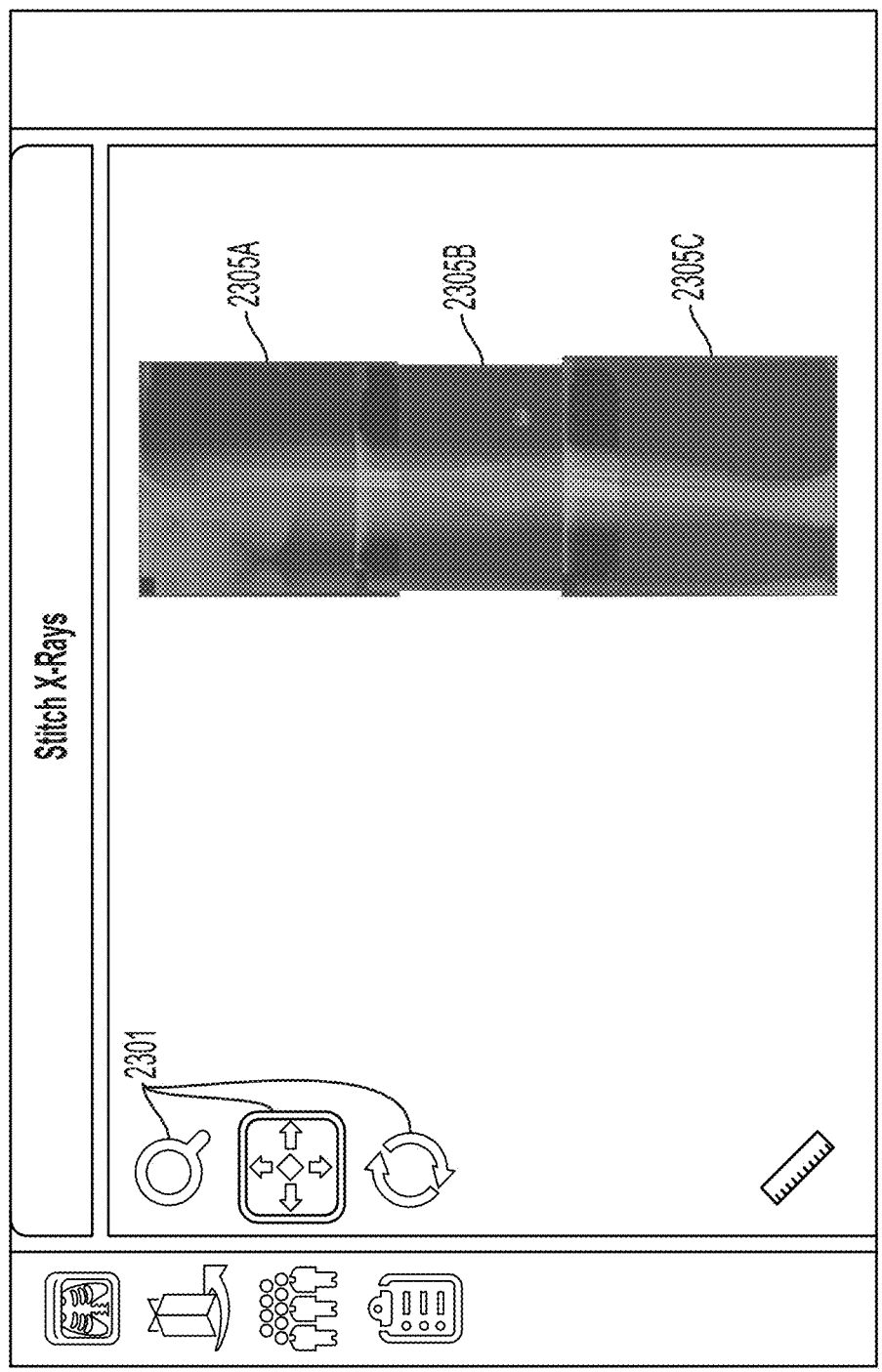
Figure 23C:
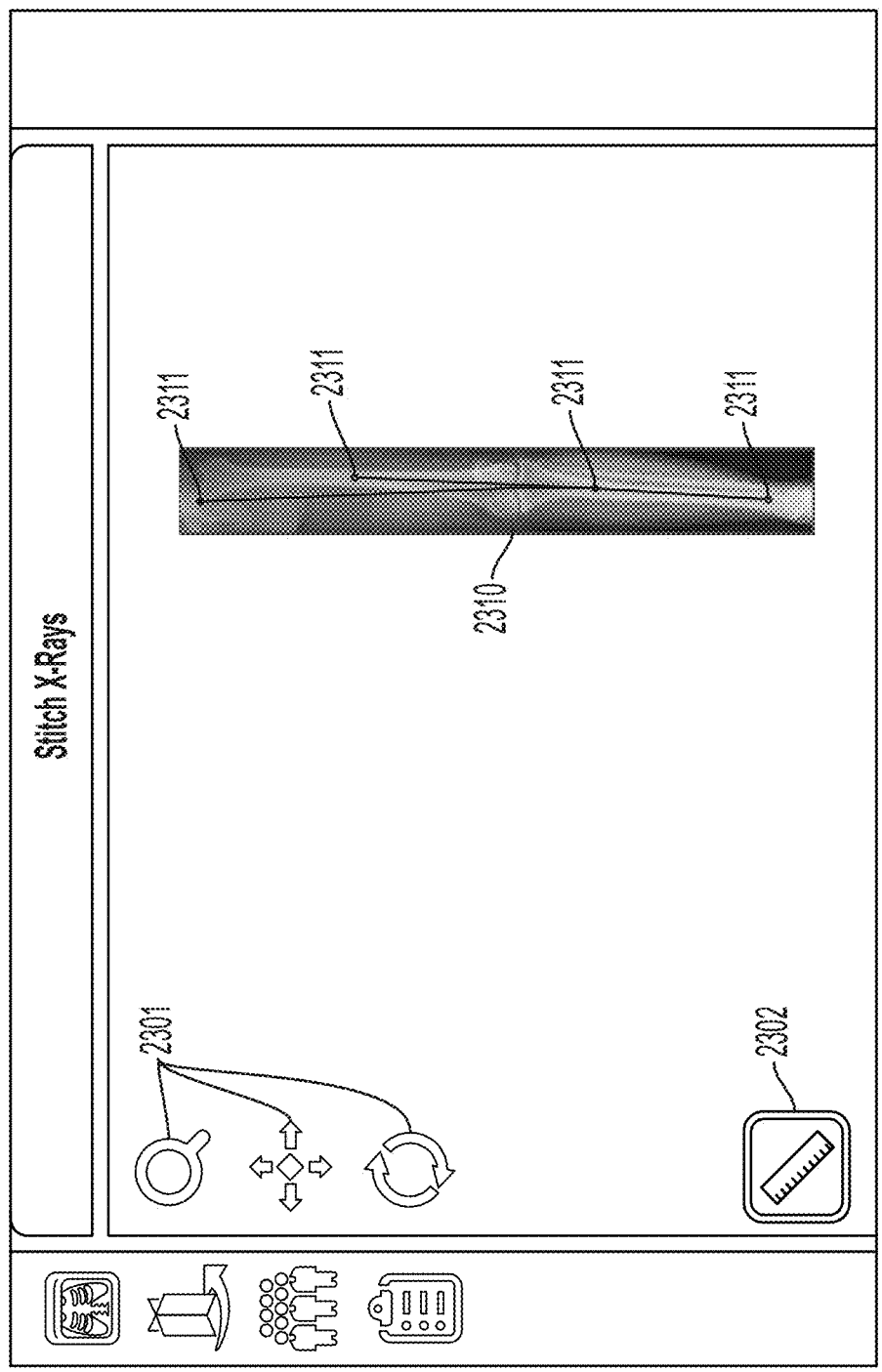

In some embodiments, as shown in FIGS. 23A-23C, alignment of the 2D images may require repositioning, rotating, and/or scaling each 2D image to align with other images. As depicted, the composite image 2310 may also be cropped to isolate the bones of the joint. In some embodiments, the co-registration may be performed manually through the user interface via alignment tools 2301 (e.g., move, rotate, scale, etc.). In a further embodiment, the co-registration may be performed by a computing device which recognizes one or more anatomical features. In some embodiments, a user may make manual adjustments to the computer-generated co-registration.

In some embodiments, and as shown in FIG. 23C, the composite image 2310 may be used to determine bone size, bone alignment, bone deformities, mechanical axis, joint line, etc. In some embodiments, and as shown, one or more key points 2311 may be identified (e.g., manually or autonomously). By way of non-limiting example, in an embodiment where the key points are selected manually, a user may select a measurement tool/guide 2302 to enable the points to be selected, as well as the ability to associate one or more points with one or more other points (e.g., to create an axis line (e.g., a mechanical axis or anatomical axis), best fit curve line, etc.). In other embodiments, a computing device may identify (i.e., auto-segment and/or auto-landmark) the one or more key points (e.g., based on machine learning, artificial intelligence, artificial neural networks, or the like). The user may make manual adjustments to the automatically identified key points. In some embodiments, the set of key points are a pre-determined set which are desired for calculating a pre-determined set of properties of the bones. For example, the system and/or the user may identify the center of the femoral head, one or more articular surfaces, one or more condyles, the intercondylar notch, the center of the shaft, one or more additional points along an axis of the shaft, and the like. The system may calculate one or more properties of the bones of the patient, such as bone size, bone length, anatomical axis, mechanical axis, etc. The system may also identify a deformity of the bone and/or calculate a degree of deformity. For example, a varus, valgus, and/or bow angle deformity of the femur, tibia, and/or entire leg may be calculated.

Figure 24A:
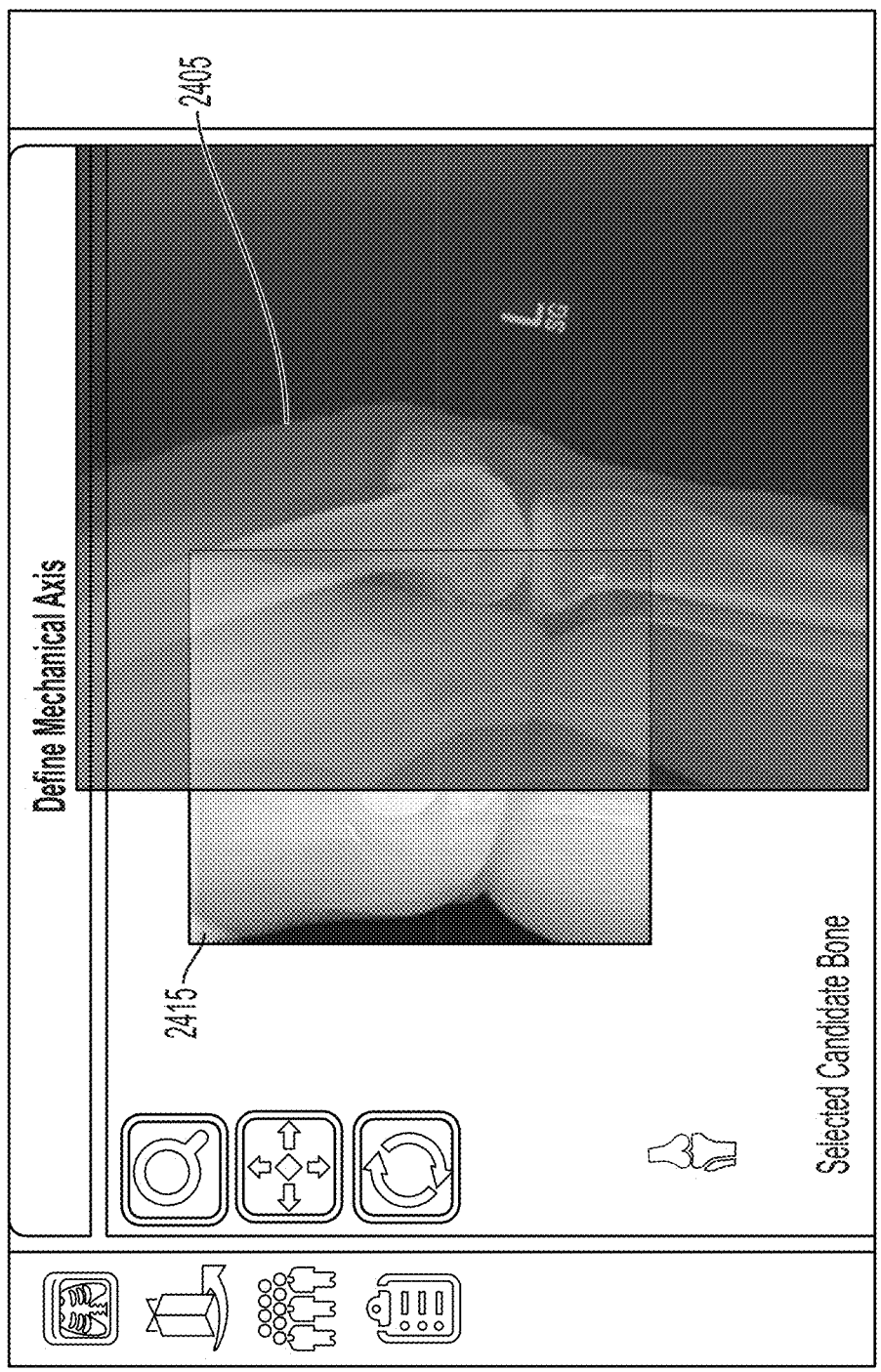
FIGS. 24A-24B depict a process of aligning a bone relative to a common coordinate system in accordance with an embodiment.
Figure 24B:
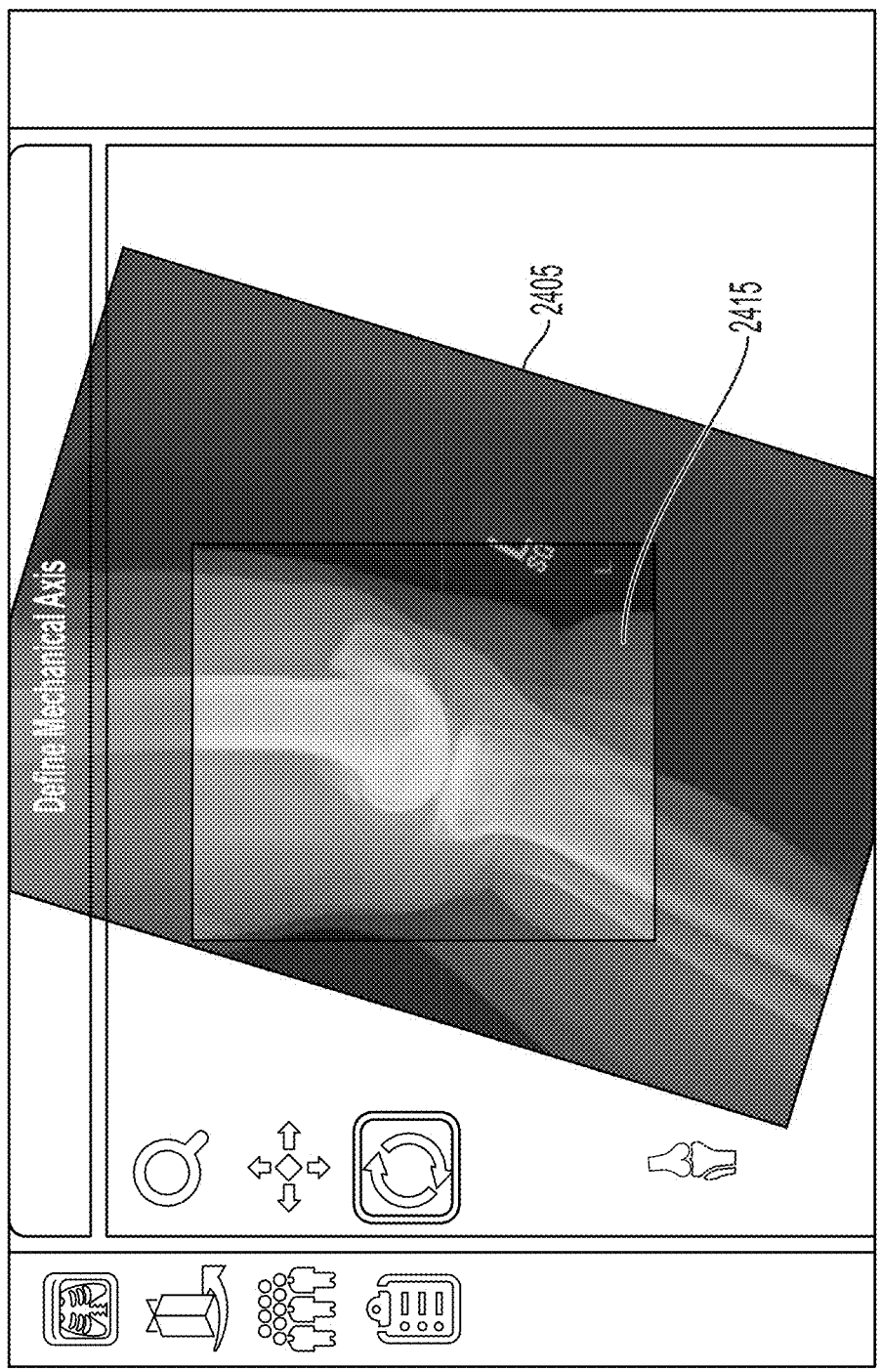

Referring now to FIGS. 24A and 24B, the candidate bone may be conformed to a common, or known, coordinate system (i.e., FIG. 22 at 2201). For example, as seen in FIG. 24A, a 2D image 2405 (i.e., the composite image 2310, a portion thereof, or one of the plurality of 2D images 2305A-2305C) of the candidate bone may be compared (e.g., overlaid) and aligned with a template bone 2415 so as to place the candidate bone in a pre-determined orientation. The template bone 2415, which has a known position, orientation, and scale with respect to the common coordinate system (e.g., a coordinate system based on the key points), provides a representation to which the candidate bone may be aligned. In some embodiments, the template bone 2415 may be an idealized bone or preferred bone utilized by default for an initial comparison. In other embodiments, the template bone 2415 may be an initial representative bone selected from a library of representative bones, as discussed further herein. In some instances, the representative bone is selected to closely match the candidate bone based on any and/or all known data (key points, landmarks, axes, anatomy size, orientation, angle, and/or the like of the 2D images, demographic data collected from the patient, historical medical images, and/or the like). Alignment of the 2D image 2405 may include repositioning, rotating, and/or scaling of the 2D image 2405 to substantially match and align with the template bone 2415, as shown in FIG. 24B, such that the candidate bone of the 2D image 2405 is placed in the pre-determined orientation. Alternatively, the template bone 2415 may be repositioned, rotated, and/or scaled to match and align with the 2D image 2405, thus achieving the same result. As discussed herein, alignment of the 2D image may be performed by a user and/or software (e.g., based on image analysis, artificial intelligence systems, or other neural network based systems).

Based on the repositioning, rotating, and/or scaling of the 2D image 2405 with respect to the template 2415 (i.e., FIG. 22 at 2201), the system may identify the location of the various identified key points 2311 with respect to known key points of the template 2415. Accordingly, in some embodiments, the system may identify one or more potential representative bones for comparison with the patient bone utilizing any and/or all available patient data (as briefly described with respect to template bone 2415). The potential representative bones may be identified from a library of representative bones (e.g., a library of historical bone image data). By way of non-limiting example, the system may utilize one or more key points (and their locations relative to one another and/or corresponding key points of the template 2415) and/or any calculated properties of the patient bone, including, but not limited to, bone dimensions, bone deformities, bone thickness, mechanical axis, and anatomical axis to identify substantial matches among the historical bone image data. In some embodiments, the system may also collect a variety of biometric and demographic data, such as age, height, weight, ethnicity, activity level, previous injuries and medical data, and the like, which may be cross-referenced with the historical bone image data. It should be understood that the representative bones may only be roughly equivalent to the patient's anatomy.

In some embodiments, as the user and/or AI system aligns the 2D image, it may be determined that the template 2415 and the 2D image 2405 differ enough in shape, size, position, rotation, etc. such that further alignment is required. For example, as a user aligns the 2D image 2405 with the template 2415, further incongruities may become evident, prompting the user to further position, rotate, and/or scale the 2D image to more suitably match the template 2415.

In some embodiments, the process described with respect to FIGS. 24A-24B may be performed iteratively. In a further embodiment, the user and/or AI system may review the identified potential representative bones and choose to return to the alignment step 2201. In some embodiments, this may occur because the user and/or AI system determines that the potential representative bones do not match the 2D image 2405 to an acceptable degree.

In other embodiments, the AI system may prompt the user to return to the alignment step 2201, for example, if suitable potential representative bones are not identified. For any of the reasons herein, the user and/or AI system may return to the alignment step 2201 and further re-align the 2D image 2405. In some embodiments, this alignment is performed with respect to the same template 2415. In other embodiments, a new template 2415 is utilized herein, for example, the various templates could exist based on patient age, size, demographic, etc. Moreover, in a further embodiment, the new template 2415 may be one of the identified potential representative bones.

Using the iteratively updated alignment process, discussed herein, may result in one or more updated results/options (i.e. a new set of identified potential representative bones and/or a modified or updated template) based on any changes to the bone dimensions, calculated properties, position of the key points 2311 relative to one another, the key points of the template 2415, and any of the various factors discussed herein. In some embodiments, the user and/or AI system may choose to revert to the previous set of potential representative bones. This process may continue iteratively until acceptable results are identified.

In some embodiments, the new set of potential representative bones may, in whole or in part, include potential representative bones of the initial set. Further, in some embodiments, the new set of potential representative bones may be, in whole or in part, "neighbors" (i.e., bones identified in the library as showing substantial similarity to the initial set of potential representative bones based on the key points and all other available data as described herein) of the initial set of potential representative bones based on the common coordinate system. In some embodiments, the similarity of bones in the library may be quantified by a magnitude of similarity, such that the potential representative bones may be arranged and/or presented in a ranking order of similarity to one another.

The library may include historical bone image data from a plurality of patients. For example, the library may comprise bone image data received from a plurality of physicians across a plurality of hospitals and locations. The historical bone image data may be processed in various manners to allow for more accurate comparison with a 2D image of a candidate bone. For example, in some embodiments, the historical bone image data may include 2D images, which may be directly presented (e.g., 2510A, 2520A, 2530A, and 2540A) for comparison with the 2D image 2405 of the patient bone. In alternative embodiments, the library may include at least one 3D image, 3D image data, 3D solid, or other 3D data representing a bone without having corresponding 2D image data. For example, in some cases, a historical 3D representation (e.g., MRI or CT) of the anatomy of a patient may be included in the library without a corresponding 2D image (e.g., when patients only undergo 3D medical imaging). In such cases, an embodiment may utilize a conversion module that can transform the 3D image data into a representation of a 2D image or a recreation of a 2D image that is visually similar to a standard, or existing, 2D image style (e.g., an X-ray).

In a further embodiment, representative bone(s) in the library may be conformed or aligned to the common coordinate system (i.e., have a pre-determined orientation, angle, and/or view) such that the representative bones have a known initial orientation, angle, and/or view. In some embodiments, the initial orientation/angle of the representative bone conforms to a pre-determined view. The pre-determined view may be a standard imaging view, such as a view commonly utilized in clinical scenarios or according to textbook directions. By orienting the view with respect to the anatomy and/or the clinical environment (e.g. an X-ray table or X-ray cassette) in the same manner that a clinician may commonly orient patients, the user may be initially presented with a view that is similar to clinical scenarios and thus familiar to an individual having experience with medical imaging. As a result, the user may be able to better evaluate the potential representative bones, for example by identifying features or landmarks of the bone from the same viewpoint as they commonly appear in the clinical setting. In some embodiments, the pre-determined view may correspond to a specific pose of the patient that is common in clinical settings, e.g. supine position, standing position, or seated position. In further embodiments, the pre-determined view may be a view that distinctly displays one or more anatomical features or landmarks to allow for clear visualization and comparison.

Figure 25A:
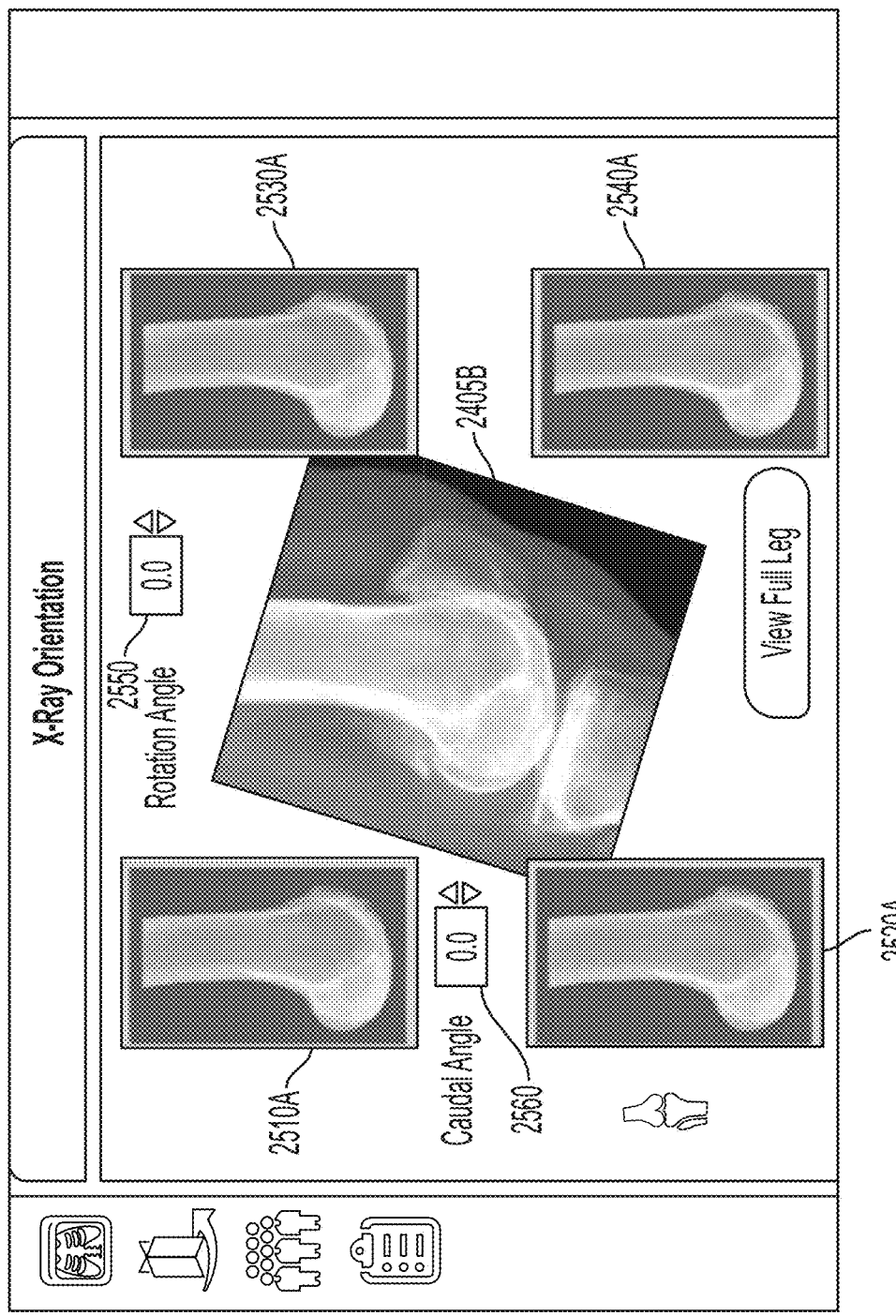
Figure 25B:
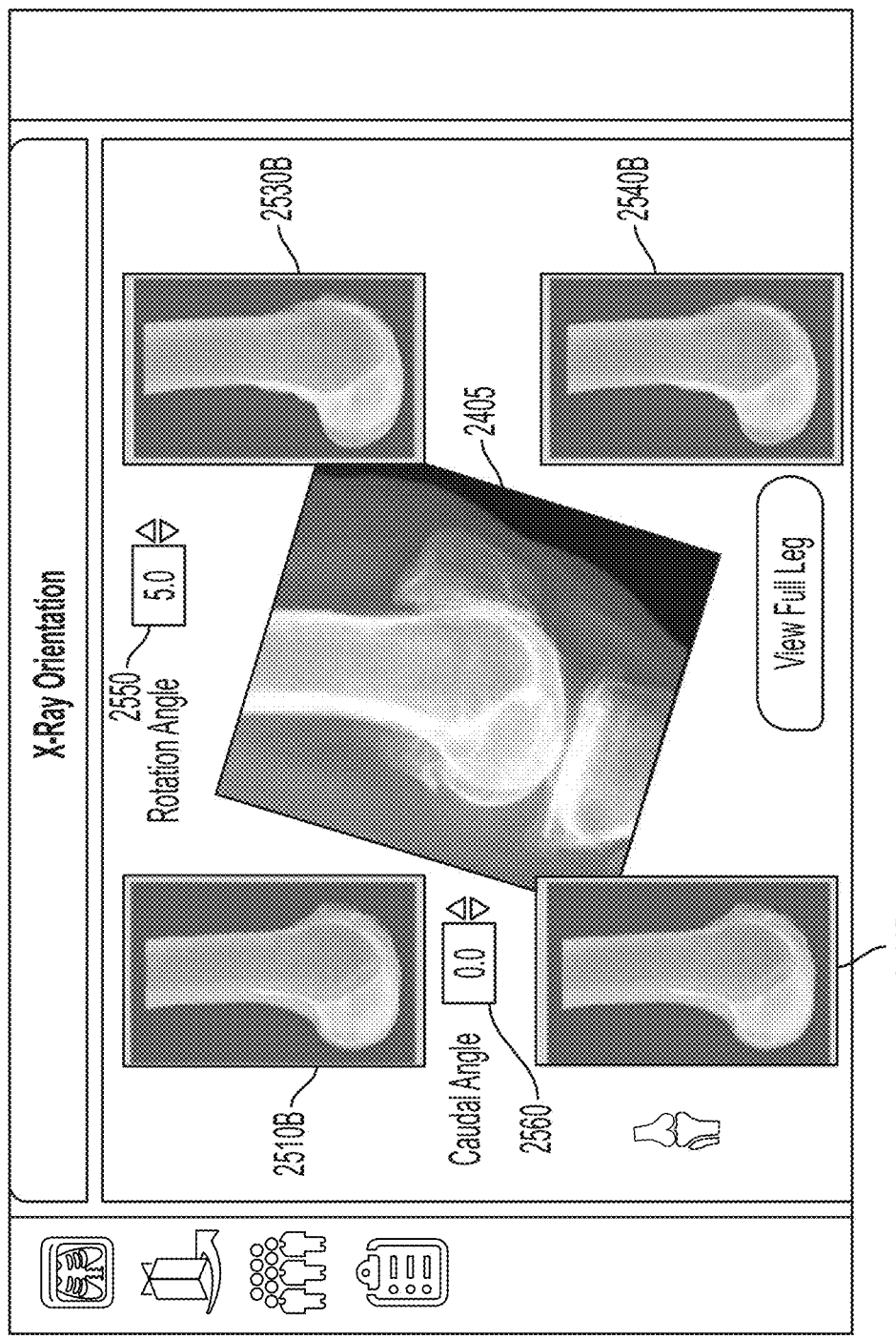

Referring now to FIGS. 25A-25C, an embodiment is shown illustrating step 2202 of FIG. 22, where a plurality of views of a representative bone are reviewed to select a best match to the candidate bone of the 2D image 2405. In some embodiments, a representative bone may be chosen by the user and/or AI system based on the review of the set of potential representative bones. For example, as shown in FIG. 14, the system presents a set of potential representative bones (i.e. one or more representative bones 1402) meeting a threshold of similarity from which the user and/or AI system may select a representative bone. In some embodiments, the system presents a 2D image 1401 of the candidate bone of the patient (e.g. 2D image 2405) in addition to the one or more representative bones 1402 for ease of comparison such that the user may select a representative bone therefrom by comparison. In other embodiments, the representative bone may be chosen by the system from the set of potential representative bones based on a quantified magnitude of similarity to the 2D image 2405 (e.g., a representative bone exhibiting the greatest magnitude of similarity). As seen in FIG. 25A, the representative bone may be presented from a plurality of views (e.g., 2510A, 2520A, 2530A, and 2540A) in order to minimize or eliminate ambiguities which may presented when observing the representative bone from a single 2D view.

As demonstrated in FIGS. 25A-25C, a 2D image (i.e., of the patient bone) 2405 may be analyzed with respect to one or more presented views of the representative bone (e.g., 2510A-C, 2520A-C, 2530A-C, and 2540A-C) to identify a suitably matching view. In doing so, a user and/or automation software may directly compare corresponding anatomical features, key points, or landmarks of the bones. For example, a condyle may be compared across the representative bones and the 2D image of the patient with respect to its size, shape, and position. While the views 2510A-C, 2520A-C, 2530A-C, and 2540A-C are aligned with the candidate bone of the 2D image 2405 to the common coordinate system, the images may need further orientation, or refinement, in terms of their rotation angle 2550 and/or caudal angle 2560. For example, it may be useful to compare the anatomical feature, key point, or landmark as it appears from different viewpoints in order to eliminate ambiguities in the 2D views. Thus, in some embodiments, a user and/or automation software may be able to adjust the rotation angle 2550 and/or caudal angle 2560 of the views (e.g., 2510A-C, 2520A-C, 2530A-C, and 2540A-C, individually or in unison) in order to identify and determine a better potential match between a view and the candidate bone of the 2D image.

Figure 25D:
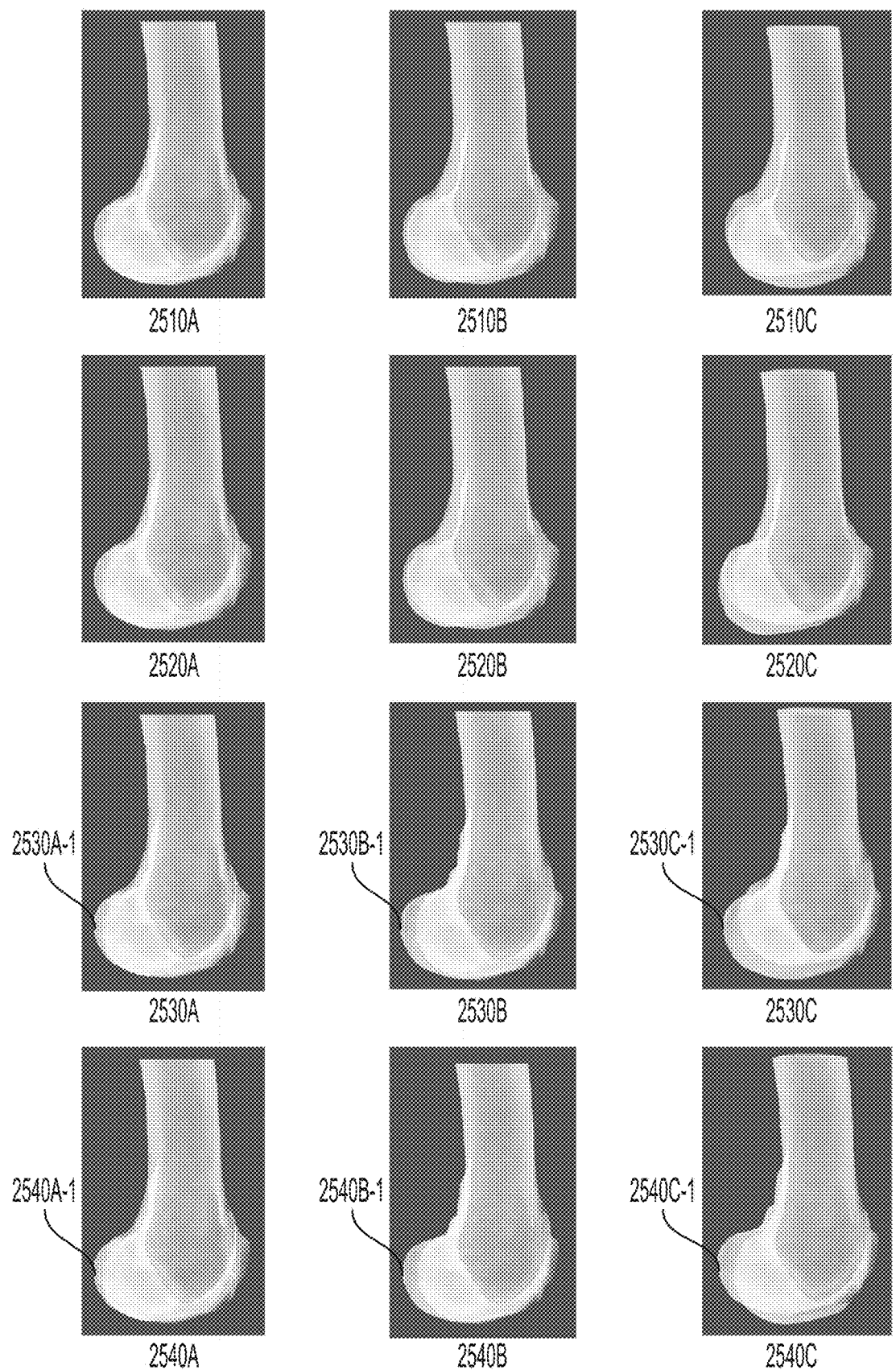

A non-limiting illustration of the 2D views is shown in FIG. 25D. Thus, as shown, the first column (i.e., 2510A, 2520A, 2530A, and 2540A) represents each of the four views with no adjustment (i.e., as shown in FIG. 25A). The second column (i.e., 2510B, 2520B, 2530B, and 2540B) represents each of the four views with a five degree (5°) adjustment to the rotation angle. As shown in FIG. 25B, views 2510 and 2520 have been adjusted 5° rotationally in a first direction from their original orientation (2510A and 2520A as seen in FIG. 25A) while views 2530 and 2540 have been adjusted 5° rotationally in the opposing direction from their original orientation. Finally, the third column (i.e., 2510C, 2520C, 2530C, and 2540C) represents each of the four potential views with a five degree (5°) adjustment to the rotation angle and a five degree (5°) adjustment to the caudal angle. As shown in FIG. 25C, views 2510 and 2530 have been adjusted 5° caudally in a first direction from their original orientation (2510A and 2530A as seen in FIG. 25A) while views 2520 and 2540 have been adjusted 5° caudally in the opposing direction from their original orientation. As a result, four unique views of the representative bone are presented (as shown in FIG. 25C).

Accordingly, as shown in FIG. 25D, closer matching of at least one of the 2D views to the 2D image 2405 may be achieved by adjusting the views. While presentation of similarly sized and shaped bones may provide adequate comparison for selecting a suitably matching representative bone and/or view, ambiguities may still exist in the 2D comparison. For example, as shown in 2530A, a small shadowed area 2530A-1 is depicted. In some embodiments, the shadowed area may be too small to discern whether it represents soft tissue or the edge of a condyle. Thus, in some embodiments, the views may be rotated to better determine the depicted anatomy. As discussed herein, the determination that the orientation/angle should be altered may be made by a user and/or software (e.g., based on image analysis, artificial intelligence systems, or other neural network based systems). Thus, as shown, 2530B is a 2D representation in which the view shown in 2530A has been rotated five degrees (5°). As shown in 2530B, the shadowed area 2530B-1 is much larger than shadowed area 2530A-1. This is because, in this particular example, the two condyles (i.e., medial condyle and lateral condyle) overlap one another in a 2D image. Thus, as the bone is rotated, the alignment of the condyles is shifted to permit a better view.

In a further embodiment, as discussed with reference to FIG. 25C, the 2D views may be further modified (e.g., the caudal angle may be adjusted) to further increase or enhance the 2D view of the anatomy. Thus, as shown, the original view 2530A may be modified by adding a five degree rotation and adjusting the caudal angle by five degrees as depicted in view 2530C. Accordingly, based on this modification, it can clearly be seen that the small, difficult-to-discern shadow 2530A-1 may be enhanced, or better viewed, 2530C-1 by making minor adjustments to the potential representative bones. Additional examples of these visual enhancements may exist (e.g., 2540A-1, 2540B-1, and 2540C-1).

It should be noted that the illustrations of FIGS. 25A-25D are intended to be non-limiting examples. Thus, while FIGS. 25A-25D depict the rotation and caudal angle being adjusted by 5°, the rotation angle and/or the caudal angle may be adjusted by up to 10°, up to 15°, or greater than 15°. Further, all possible increments are contemplated herein. The rotation angle and/or the caudal angle may be adjusted in smaller increments (e.g. a single degree or fraction of a degree) or larger increments (e.g. 10° or more). In some embodiments, increments may be chosen that enact a demonstrable and clinically relevant change in the angles, while still providing the level of granularity required to precisely match the view to the 2D image of the patient bone. Additionally, while the adjusting the rotation angle and the caudal angle is discussed herein in terms of degrees, the angles may be adjusted in other incremental units. One or more non-limiting examples may include, adjusting by a percentage of the angle, an arc length, an arbitrary or best fit unit, and the like.

As discussed herein, view 2530A depicts a potential representative bone in an original orientation. It should be understood that although the initial views are depicted as being the same, the initial views of the potential representative bones may vary. In some embodiments, any original orientation/angle, as long as such are known or defined by the system, may be accommodated. Multiple distinct initial views may allow a more rapid and more clear comparison to the 2D image 2405.

In some embodiments, as the user and/or AI system orients the views to the 2D image 2405, it may be determined that the views and the 2D image 2405 differ enough in rotation and/or caudal angle that further alignment is required. For example, as a user orients the views 2510/2520/2530/2540 to match the 2D image 2405, further incongruities may become evident that prompt the user to further orient the views.

In some embodiments, the user and/or AI system may elect to return to the set of potential representative bones (e.g., as shown in FIG. 14), and select a new representative bone.

The process described with respect to FIGS. 25A-25D may be performed iteratively. In a further embodiment, as a user orients the views 2510/2520/2530/2540 to match the 2D image 2405, the system may utilize the orientation of the views as indicative of the orientation (i.e., rotation angle and caudal angle) present in the 2D image 2405. The orientation information may result in updated results (i.e. a new set of identified potential representative bones) based on the orientation information and any of the various factors discussed herein. The user and/or AI system may review the new set of identified potential representative bones (e.g., as shown in FIG. 14) and select a new representative bone. Accordingly, the user and/or AI system may return to the orientation step with the new representative bone. Further, the user and/or AI system may choose to return to the alignment step 2201. Alternatively, the user and/or AI system, upon review, may choose to continue with the initial representative bone. In other embodiments, the AI system may prompt the user to perform any of the described actions. The process may continue iteratively until a 2D view of a representative bone can be identified that meets or exceeds a similarity threshold (i.e., an ideal view). In some embodiments, if no representative bone and/or corresponding view can be found that meets the threshold, a user or AI system may reduce or modify various factors associated with the threshold until a suitable view of a representative bone is found.

Figure 26A:
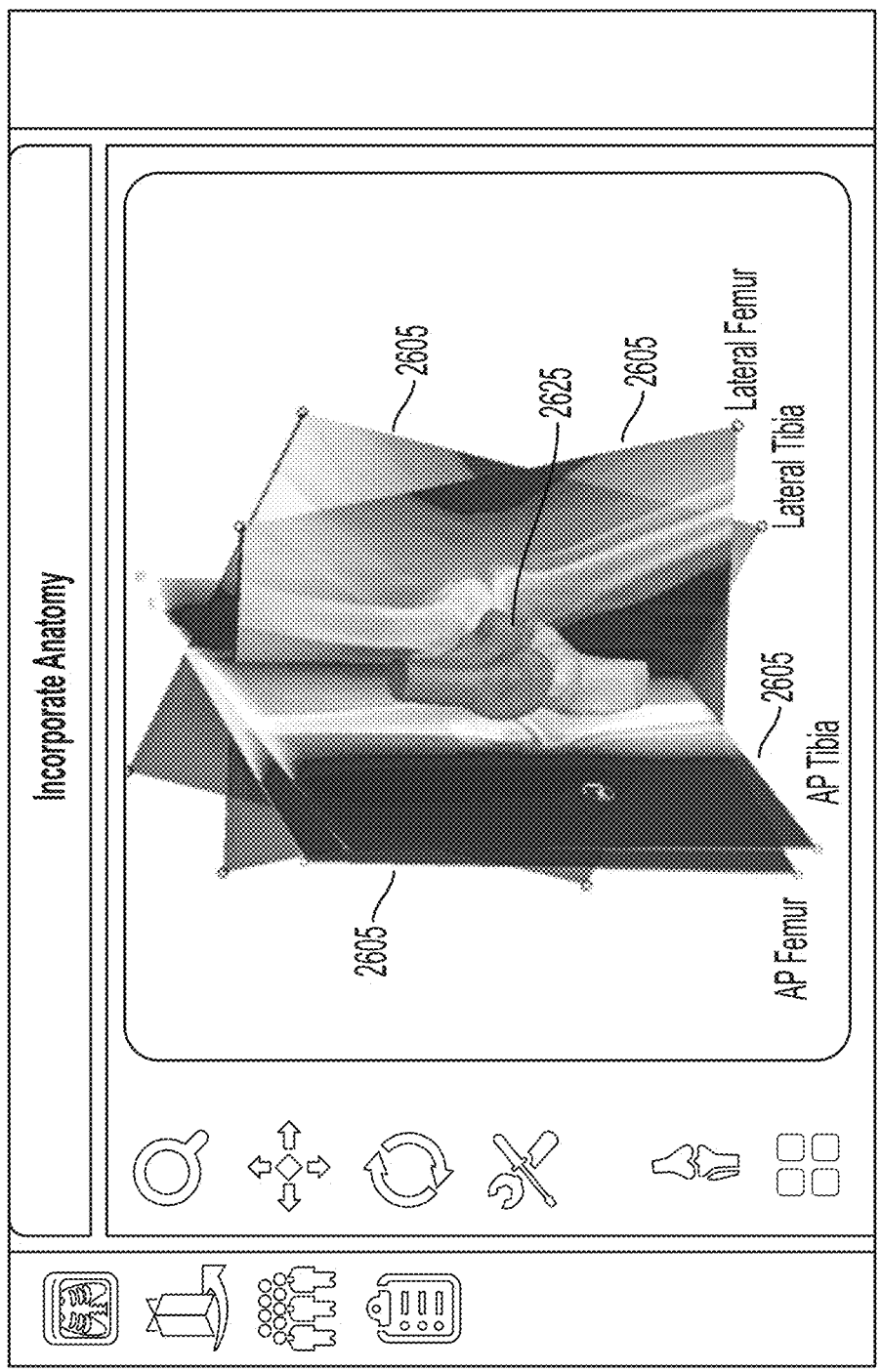
FIGS. 26A-26B depict a process of scaling and re-orienting a 3D bone model with respect to at least one 2D image in accordance with an embodiment.
Figure 26B:
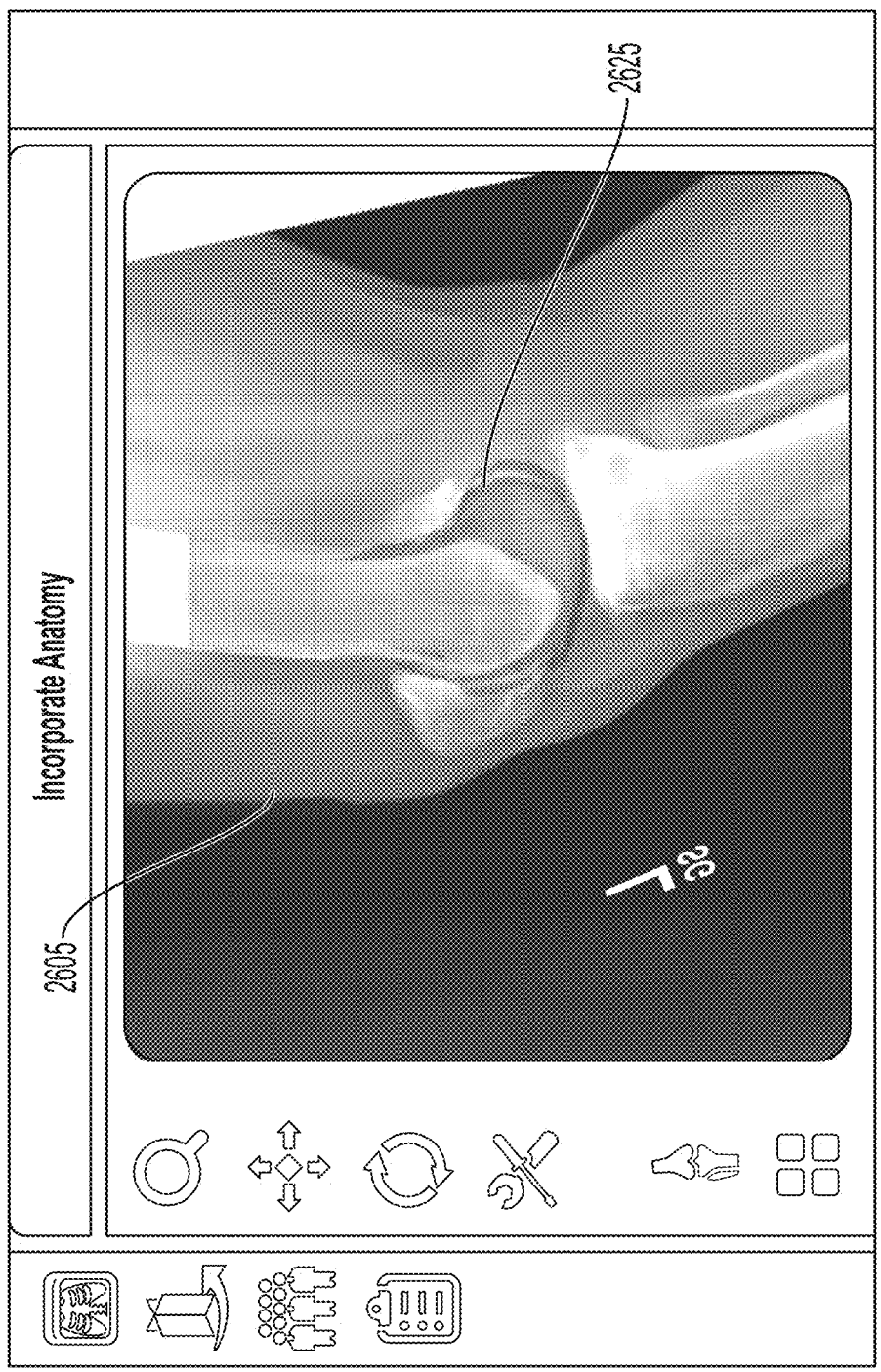

FIGS. 26A and 26B provide a non-limiting example of step 2203, regarding adjusting the 3D bone model (i.e., the 3D bone model corresponding to the selected representative bone). As shown in FIG. 26A, the 3D bone model 2625 is overlaid on one or more 2D images 2605 (e.g., 2D images 2305A-2305C) based on the selected ideal view. In some embodiments, one of the 2D images (e.g., AP Femur, AP Tibia, Lateral Tibia, Lateral Femur, etc.) may be selected individually for a direct comparison, as shown in FIG. 26B, where the 2D image may be further re-positioned, re-scaled and/or re-oriented to match the 3D bone model to a greater degree. Alternatively, the 3D bone model 2625 may be further re-positioned, re-scaled, and/or re-oriented to match the 2D image to a greater degree, thus achieving the same relative position, orientation, and scale. This process may be repeated with one or more additional 2D images, such that the 3D model is further adjusted to a best fit. In a further embodiment, the selected 2D image 2605 may move along a single axis in a locked plane (e.g., in the A to P, P to A, L to M, or M to L) in order to confirm and/or evaluate the 3D model at various points.

Figure 27:
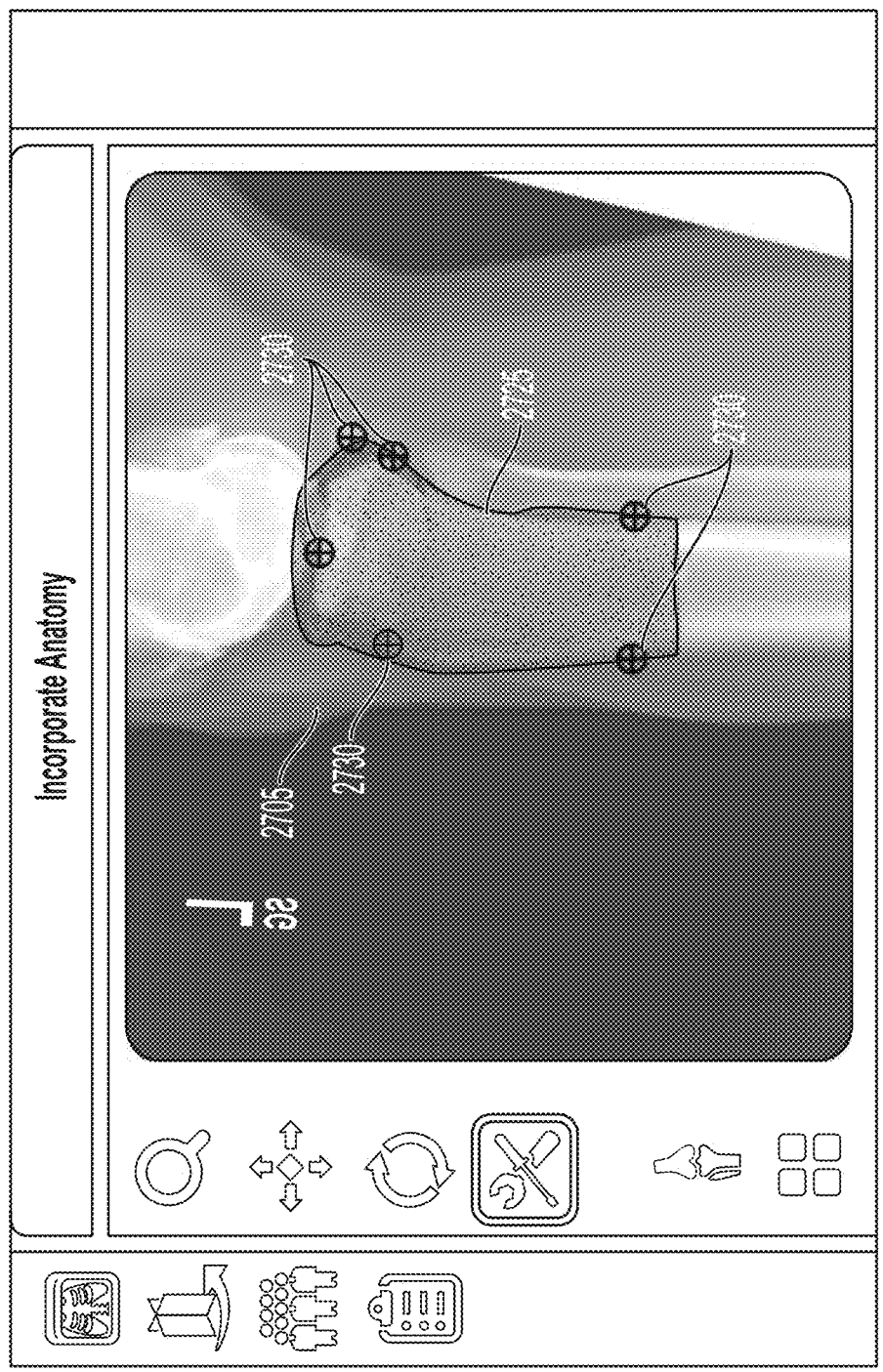
FIG. 27 depicts a process of modifying the contours of the 3D bone model in accordance with an embodiment.

Referring now to FIG. 27, an illustrated embodiment is shown that is associated with the step of modifying the 3D bone model 2204. As shown in FIG. 27, some incongruity may persist between the representative 3D bone model 2725 and the 2D images 2705 (e.g., 2D images 2305A-2305C). Thus, in some embodiments, one or more contours of a 3D bone model may be altered by adjusting one or more points 2730 on the 3D bone model. These alterations may be reliant upon a library of bone image data (not shown). Thus, in some embodiments, a contour of the 3D bone model may only be adjustable to a particular point in space if that point corresponds to a contour of a known 3D bone model (e.g., from the library).

For example, when a point 2730 on the 3D bone model is selected for adjustment, the system may access and/or create a proximity-based point cloud that determines any and all potential positions for the corresponding points across a plurality of 3D bone models in the library. When the selected point 2730 is adjusted in a given direction (e.g., up, down, left, right, etc.), it may "snap" to an adjacent position within the point cloud. Thus, because the new position for the selected point 2730 corresponds to an existing point on at least one 3D image stored in the library, the data therefrom is used to adjust the contour of the 3D bone model to account for the new position of the selected point 2730. In an embodiment where a user manually modifies one or more contours of the 3D bone model, visual assistance may be provided by the system. For example, as the selected point 2730 is adjusted, the new contour resulting from the instant position of the selected point 2730 may be displayed to the user in real time. The new contour may be illustrated by superimposing the resulting cutout or additional bone mass upon the 3D bone model (e.g., displayed as an opaque or semi-transparent feature mimicking the appearance of the bone, the 3D model, or a simulated X-ray). While a discrete set of points 2730 is demonstrated in FIG. 27, this is only illustrative. It is contemplated that any point along the periphery of the 3D bone model may be selected and repositioned according to the corresponding point cloud. Once all contour modifications are complete, the result is a custom 3D model representing the candidate bone of the patient.

The manner of representing the 3D bone model described herein is intended to be exemplary and non-limiting. The 3D bone model could alternatively be represented in any of a variety of manners for the purpose of modifying a contour or region. For example, the 3D bone model could be represented as joined chips or segments of corresponding X-ray data from the library, such that the various chips or segments may be repositioned to match a 2D image 2705. In some embodiments, fine tuning adjustments may be performed in the manner described herein with respect to FIG. 16. For example, fine tuning adjustments may result in subsections from multiple 3D bone models being combined and normalized to form the 3D model of the bone of the patient. Any of the various techniques for modifying, updating, and/or combining 3D models described herein may be utilized in step 2204.

In a further embodiment, the 3D bone model may be based on statistical shapes (i.e., a statistical shape model). In addition to scaling or otherwise adjusting the 3D bone model as a whole, individual statistical shapes may be scaled or adjusted in order to modify a discrete portion or region of the 3D bone model to better match the 2D image 2705. For example, in some embodiments, the size of a specific condyle of the 2D image may not match that of the 3D bone model, while other features of the bone are matched to a high degree of accuracy. In this case, one or more individual statistical shapes of the 3D bone model corresponding to the condyle may be scaled as a whole to better match the condyle of the 2D image. In another embodiment, a deformity may be misrepresented or not represented at all by the selected 3D bone model (e.g., the library may contain little data representing a rare deformity). In such a case, one or more individual statistical shapes of the 3D bone model corresponding to a region including the deformity may be scaled and/or adjusted to better represent the deformity and better match the 2D image.

It should be noted that the resulting custom 3D model of the candidate bone may be accurate to a greater degree with respect to some features of the candidate bone than others. In some embodiments, where the custom 3D model is produced with a known purpose, particular features or regions of the bone may be of greater significance to the utility of the custom 3D model, whereas other features or regions may be less significant or entirely irrelevant. For example, where a custom 3D model is being produced for further use in designing and manufacturing a custom cut guide, the particular surfaces and regions of the bone that the cut guide will sit against and contact the bone are of great importance to assure proper fit and orientation with the bone. However, other regions may not contact the cut guide when in use and may be irrelevant for designing the cut guide beyond ensuring that these regions do not interfere with the fit and seating of the cut guide. As such, in some embodiments, the user and/or AI system may focus on achieving a high degree of similarity between the 2D images and the custom 3D model with respect to the features, surfaces, and regions of interest. Further features, surfaces, and regions may have a lower threshold of similarity, which may be implemented in the custom 3D model in various manners (e.g. gaps or tears in the surfaces of the custom 3D model, generic or approximated surface shapes with an indicated margin of error) such that a system utilizing the custom 3D model could account for these uncertainties. For example, a cut guide may be produced which limits contact to any uncertain surfaces or regions so as to prevent improper or ambiguous seating of the cut guide against the bone.

In some embodiments, the system may repeat each step of process 2200 for each candidate bone. For example, in the non-limiting example of a knee joint, the process 2200 could be separately performed for both the femur and the tibia. Additionally or alternatively, in the case of a hip joint, the process 2200 could be separately performed for both the femur and the acetabulum. For other joints, each bone of interest could be modeled through the process 2200 in a separate step. It is also contemplated that more than one bone could be modeled simultaneously in a single process. It is contemplated that, for each candidate bone, a different set of key points may be utilized in calculating properties as well as referencing to and comparing with the historical bone data. In a further embodiment, the process may be accelerated for additional bones. During the process 2200 for a first bone, once a representative 3D bone model is selected from the library, one or more 3D bone models of the corresponding additional bones of the joint from the same historical record (i.e., the same historical patient) may also be presented such that steps 2201 and 2202 may be skipped or simplified for subsequent bones. Adjustments to scale and orientation and modifications to contours may still be performed on an individual basis for each 3D bone model.

In an alternative embodiment, the system and/or user may simply repeat the disclosed process for each additional bone in the joint or each additional bone potentially involved in the surgical procedure. Referring back to FIG. 21, the process 2100 may be completed by producing a custom three-dimensional model of the joint 2105. After generating each of the custom 3D bone models, the models may be combined to produce the custom three-dimensional model of the joint. As the various axes of each joint have been defined and adjusted throughout this process, the alignment of each 3D bone model may be known such that they may be automatically oriented with respect to one another.

The three-dimensional model of the joint may be subsequently packaged by the system and transmitted to a variety of locations and systems. As non-limiting examples, the three-dimensional model of the joint may be transmitted to a patient record database, a clinical study database, a surgical planning system, an implant planning or manufacturing system, a guide planning or manufacturing system, a tool planning or manufacturing system, and/or a training system. Further, the library of historical bone image data may include additional information with respect to the historical bones from which the representative bones are derived and/or the historical patients associated therewith. In some embodiments, the representative bones may be associated with notes or indications by a surgeon. The notes or indications may include disease diagnosis, such as assessments of soft-tissue surrounding the historical bones and/or osteophytes which indicate a cause of disease (e.g. indicating that a bone deformity was caused by trauma or osteoarthritis). The notes or indications may additionally or alternatively include treatment plan information related to the historical bones. For example, a surgeon may indicate a degree of deformity. In a case where the deformity was not comprehensively treated (e.g., an extreme deformity may not be treated because the soft tissues may not sufficiently adapt to such treatment), the notes may indicate the extent of treatment as well. As a further example, the notes or indications may describe the choice of femoral head implant size utilized to maximize the range of motion. As an additional example, the notes or indications may include planned bone corrections using 2D or 3D digital templating software. In a further embodiment, the representative bones may be associated with implant information. The implant information may be descriptive of the specific implant (e.g., size) or descriptive of patient or bone preparation (e.g., locations of cut planes, reamed surfaces, pins, or plates). The implant information may also indicate usage of additional tools, guides, or components in the surgery or the surgical history of the patient. For example, the implant information may indicate which augments, wedges, stems, trauma plates, screws, etc. were utilized for the historical patient. Any of the additional information described herein may be predictive of an implant, an additional component, or a course of action best suited for the current patient. In another embodiment, the representative bones may be associated with surgical plans or surgical outcome data, implant design data, and the like. It should be noted that the embodiments of additional information described herein are intended to be non-limiting examples. This additional information may be relayed to external locations and systems along with the three-dimensional model of the joint. Due to the similarity of the patient's joint to the representative bones, the additional information may not only be informative and assist future decisions by medical professionals, but may further assist in planning related to a surgical procedure. In some cases, the additional information may entirely alleviate one or more steps of a planning or manufacturing process.

It is contemplated that some steps of the processes 2100 and 2200 described herein may be disregarded without halting or interrupting the process. For example, the co-registration step 2102 may be pre-performed or disregarded altogether (e.g., the process could continue utilizing a single short-film 2D X-ray image 2305 in place of the composite 2D image 2310). As a further example, the landmarking step 2103 may be disregarded without halting the process. It should be noted, however, that inclusion of the landmarking step 2103 provides further information to the system (i.e., the key points 2311) for use in identifying potential representative bones. As a further example, the modifying step 2204 may be performed separately at a later time or disregarded altogether. In some embodiments, the 3D bone model may be sufficiently representative of the candidate bone without further modifications. In other embodiments, the resulting three-dimensional model of the joint may be completed without performing the step 2204. The three-dimensional model may be packaged and transferred to another system where such modifications could occur.

It is also contemplated that one of the alignment step 2201 (i.e., the step illustrated by FIGS. 24A-24B) and the orientation step 2202 (i.e., the step illustrated by FIGS. 25A-25D) could be disregarded. In such a case, the system may nonetheless be able to identify a view of a representative bone with sufficient similarity to the 2D image 2405 for the process to continue. It is additionally contemplated that the alignment step 2201 and orientation step 2202 could be performed in reverse order.

In the case that the orientation step 2202 is performed first and/or the alignment step is disregarded, the iterative process of the orientation step 2202 may vary in some respects. For example, the views 2510/2520/2530/2540 may be views of a template 3D bone model. The template 3D bone model, which has a known position, orientation, and scale with respect to the common coordinate system (e.g., a coordinate system based on the key points), provides a representation that may be oriented to match candidate bone of the 2D image. In some embodiments, the template 3D bone model may be an idealized bone or preferred bone utilized by default for an initial comparison. In other embodiments, the template 3D bone model may be an initial representative bone selected from a library of representative bones, as discussed herein. In some instances, the representative bone is selected to closely match the candidate bone based on any and/or all known data (e.g., key points, landmarks, axes, anatomy size, orientation, angle, and/or the like based on the 2D images, demographic data collected from the patient, historical medical images, and/or the like).

Based on the re-orienting as described herein, the system is able to identify the location of the various identified key points 2311 with respect to known key points of the template 3D bone model. Accordingly, in some embodiments, the system may identify one or more potential representative bones for comparison with the patient bone utilizing any and/or all available patient data. For example, as shown in FIG. 14, the system presents a set of potential representative bones (i.e. one or more representative bones 1402) meeting a threshold of similarity from which the user and/or AI system may select a representative bone. Further, the user and/or AI system may review the identified potential representative bones and choose to return to the orientation step 2202. In some embodiments, this may occur because the user and/or AI system determines that the potential representative bones do not match the 2D image 2405 to an acceptable degree. In other embodiments, the AI system may prompt the user to return to the orientation step 2202, for example if suitable potential representative bones are not identified. For any of the reasons described herein, the user and/or AI system may return to the orientation step 2202 and further orient the template 3D bone model to the 2D image 2405. In some embodiments, this orienting is performed with respect to the same template 3D bone model. In other embodiments, a new template 3D bone model is utilized herein, for example one of the identified potential representative bones. The updated orientation may result in updated results based on changes to any of the various factors discussed herein. The new set of potential representative bones may be related to the initial set of representative bones in the same manner described herein (i.e., neighboring bones in the library) and may be arranged or presented in the same manner described herein (i.e., by ranking magnitude of similarity). In some embodiments, the user and/or AI system may choose to revert to the previous set of potential representative bones. This process may continue iteratively until acceptable results are identified.

Based on the results of the orientation step 2202, the alignment step 2201 could then proceed. The alignment of the 2D image 2405 with respect to the selected representative bone may lead to updated results (i.e., a new set of identified potential representative bones) based on the alignment information and any of the various factors discussed herein. The user and/or AI system may review the new set of identified potential representative bones (e.g., as shown in FIG. 14) and select a new representative bone. Accordingly, the user and/or AI system may return to the alignment step 2201 with the new representative bone. Further, the user and/or AI system may choose to return to the orientation step 2202. Alternatively, the user and/or AI system, upon review, may choose to continue with the initial representative bone. In other embodiments, the AI system may prompt the user to perform any of the described actions.

It is further contemplated that any of the steps in the processes 2100 and 2200 described herein may be performed by a computing device. Through machine learning, the computing device may be able to perform several steps without intervention from a user. For example, the computing device may be able to co-register the plurality of 2D images by automatically recognizing common features and aligning the 2D images accordingly. In some embodiments, the computing device may automatically identify key points (i.e., auto-landmarking). For example, a computing device utilizing machine learning may be able to more consistently and accurately identify the key points. Even further, the computing device may be able to identify a greater number of key points than may be feasibly identified manually (e.g., due to time constraints, lack of consistency, lack of accuracy, etc.). This additional landmarking may lead to more accurate generation of 3D bone models. In further embodiments, the system may automatically align candidate bones and orient the views of representative bones. Automation of all of the steps described herein is contemplated. Additionally, in embodiments incorporating one or more automated steps, the user may also have the option to make adjustments to the steps completed by the system. A user may wish to modify the position of automatically identified key points, adjust the alignment of the plurality of 2D images, or the like.

The process as described herein is not intended to be limited in terms of the particular embodiments described, which are intended as illustrations of various features. Many modifications and variations to the process can be made without departing from its spirit and scope, as will be apparent to those skilled in the art. For example, while various steps of the processes described herein may comprise re-positioning, scaling, orienting, rotating, or otherwise modifying a 2D image to better match an additional visual representation (e.g., an additional 2D image, a 3D model, a template, etc.), it is contemplated that the additional visual representation may instead be modified in a corresponding manner to better match the 2D image. Further, while various steps of the processes described herein may comprise comparing, landmarking, aligning, orienting, adjusting, or otherwise modifying a composite 2D image, it is contemplated that the modifications may be made with respect to one or more individual 2D images or a 2D image which comprises a portion of the composite 2D image.

Figure 28A:
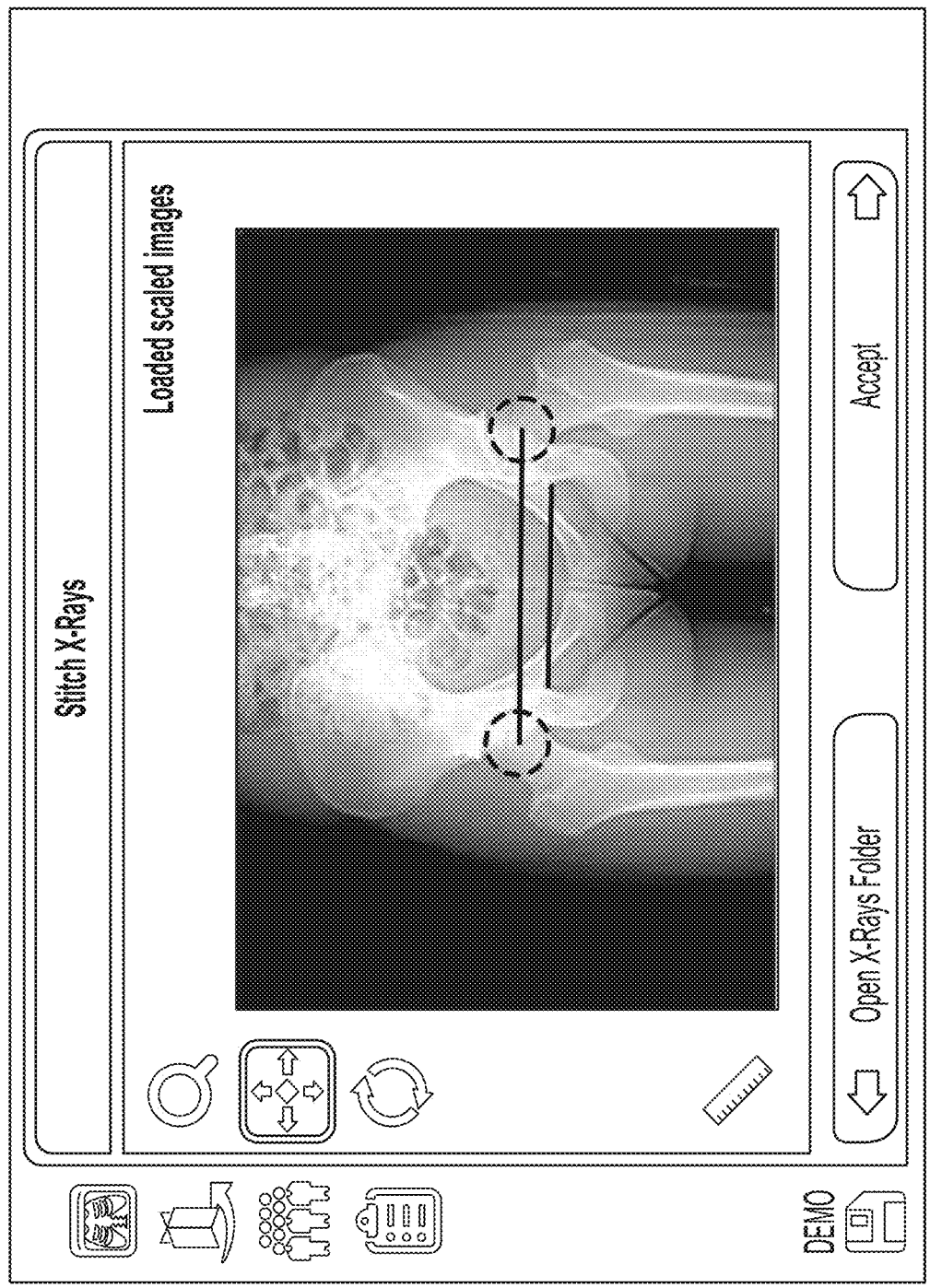
FIGS. 28A-28D depict various stages of a process of producing a custom three-dimensional model of a joint with respect to an acetabulofemoral joint in accordance with an embodiment.
Figure 28B:
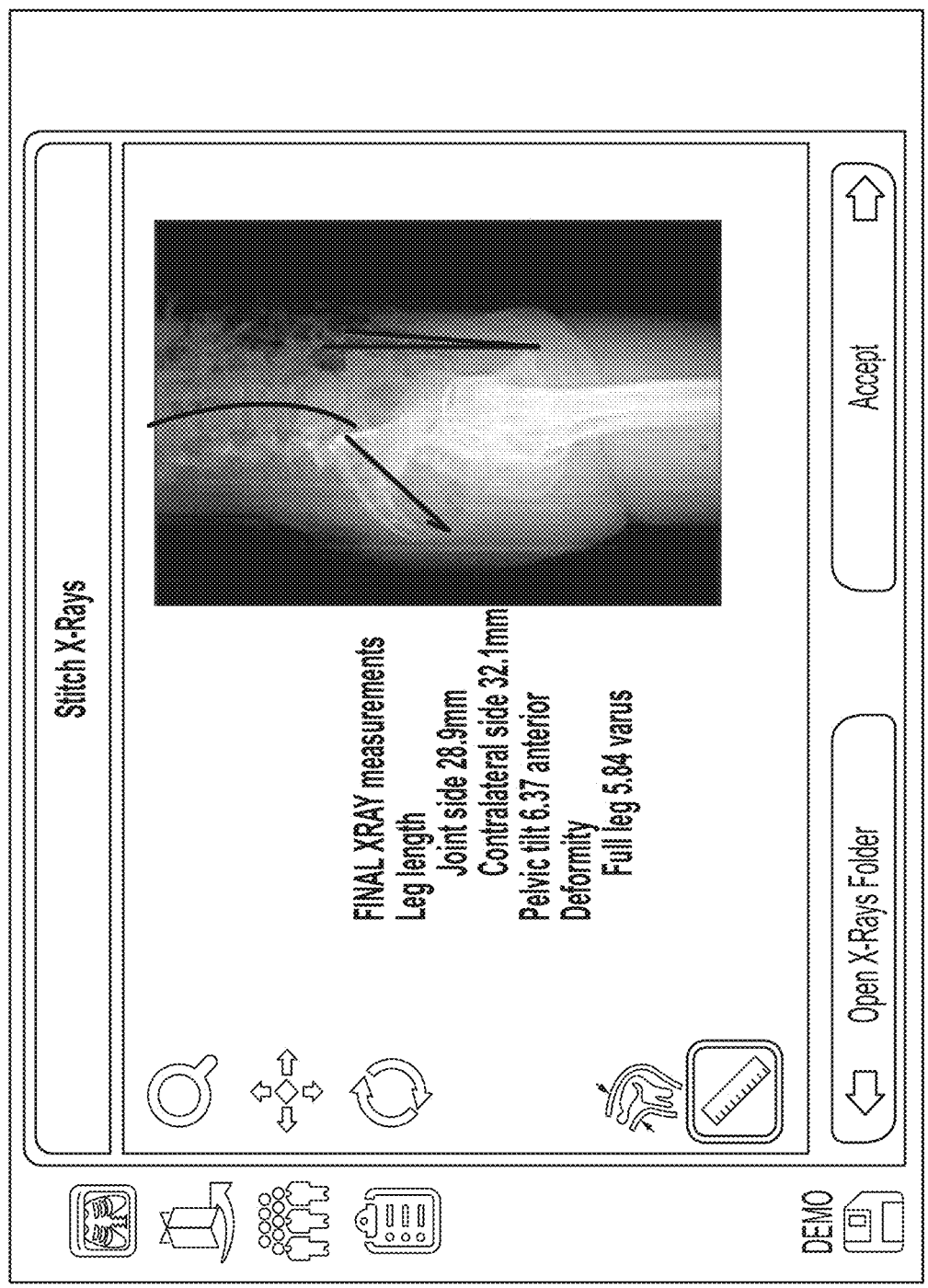
Figure 28C:
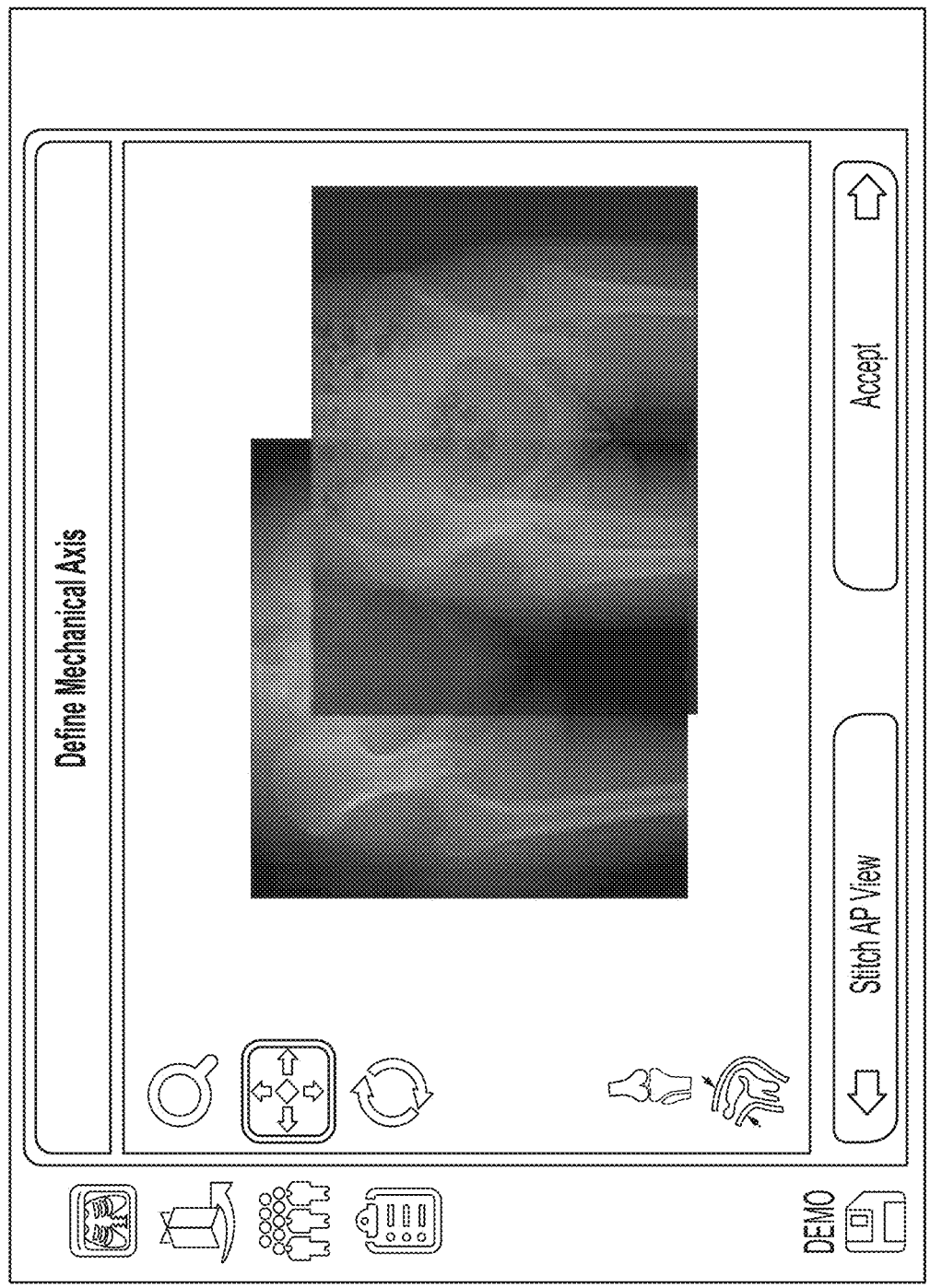
Figure 28D:
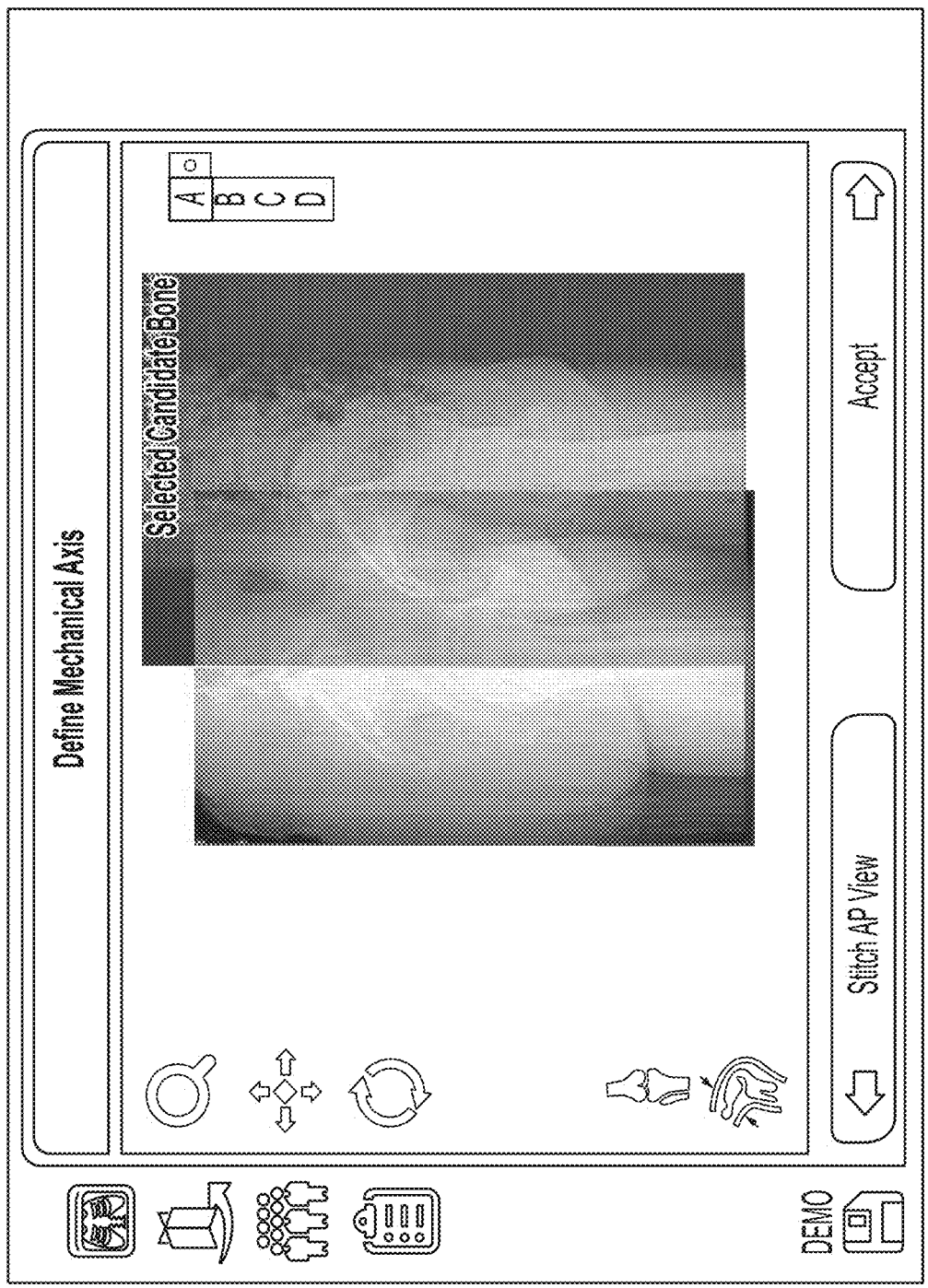

Further, while the process outlined herein has been illustrated with respect to a knee joint, it is contemplated that the procedure can be performed to produce a custom three-dimensional model of various other types of joints, including but not limited to the hip, the shoulder, the spine, and extremities such as the wrist and the ankle. For example, FIGS. 28A-28D demonstrate various steps of the processes 2100 and 2200 being performed upon an acetabulofemoral joint (i.e., hip). A custom three-dimensional model of a hip joint may be desired for planning a total hip arthroplasty or a revision total hip arthroplasty. FIGS. 28A and 28B demonstrate the co-registration 2102 and landmarking 2103 steps upon 2D images of a hip joint. FIGS. 28C and 28D demonstrate the step 2201 of conforming the candidate bone to a common coordinate system. While the previously disclosed embodiments are presented in the context of total knee arthroplasty instrumentation, it should be appreciated that similar techniques can be used to create instrumentation for the reconstruction of other joints. Furthermore, the image registration techniques could be applied to patient specific implant design. For example, the resulting 3D anatomical models could be used for design of a custom flange acetabular component for total hip arthroplasty, or custom cranial, facial, or mandibular components.

Various embodiments described herein may be applicable to other areas of orthopaedic medicine including trauma extremity reconstruction and spine. In the trauma space, 2D to 3D conversion could be used to create models of long bones. These models could facilitate the manufacture of patient specific osteotomy guides for segmental defect removal, limb lengthening, limb deformity correction, high-tibial osteotomy, etc. Furthermore, the 3D models could be used as fracture guides to restore alignment in the long bones and/or wrist after injury. In some embodiments, the 3D models may be used for patient specific pedicle screw guides and custom 3D printed spinal cages.

There are also opportunities to utilize alternate embodiments in the sports medicine space. Specifically, 2D to 3D conversion could be used to create patient specific guides for ligament tunneling used in ACL reconstruction and similar procedures and/or bone preparation for focal-defect repair.

Further, as discussed herein, while a single view may be sufficient, additional 2D images providing additional views of the plurality of bones can be provided. FIGS. 28A and 28C demonstrate the use of an AP view of the hip, while FIGS. 28B and 28D depict the use of an ML view of the hip. The images of each view may be co-registered, landmarked, and utilized in the production of custom 3D bone models. As will be apparent to one having ordinary skill in the art, the views provided may vary based on a variety of factors, including but not limited to the type of joint, the expected type of procedure, availability, and radiation exposure. For example, in the case of a hip joint, multiple views of each bone may be utilized. In some embodiments, an AP view of the pelvis and a lateral view of the pelvis may be utilized. In some embodiments, the AP view may be a low pelvic view. Further, an oblique view may also be substituted for one of the views. Additionally, an AP view and a Lauenstein (i.e., frog leg) view of the femur may be utilized. Further, multiple images from the same view (e.g., an AP view from one side of the joint and an AP view from the opposite side of the joint) may be utilized together. In some cases, views may be limited to one acetabulofemoral joint, as opposed to both acetabulofemoral joints of the pelvis. In some cases, one or more bones at a particular view (e.g., an AP view of the pelvis and an AP view of the femur) may be captured in a single 2D image. The embodiments described are intended to be non-limiting examples, and it is contemplated that the system may be utilized with any 2D views or combinations of 2D views. Due to the variance in patient imaging, various types of images and various views may be provided, and thus the system is designed to utilize any such 2D images.

While the processes herein are described and illustrated as utilizing a plurality of 2D images, in some embodiments only a single 2D image of a single view of a patient may be provided. For example, the system may identify key points and features of the 2D image, which are cross-referenced through the library of historical bone image data to identify substantially similar historical bone image data. In some embodiments, the library contains 3D models and/or additional 2D views corresponding to the identified historical bone image data, which may be utilized to synthesize alternate views of the single 2D image of the patient. The single 2D image may be utilized with the synthesized alternate views to produce a custom three-dimensional model of the joint, as otherwise described herein.

As discussed herein, the set of key points chosen for identification will vary based on the type of joint. As shown in FIG. 28A, for example, the key points for a hip joint may include the centers of the femoral heads (e.g., approximated as spheres), the pelvic teardrops, the ischial points, and/or the trochanters. Further non-limiting examples of key points for a hip joint are the iliac spines, the anterior superior iliac spine (ASIS), iliac points, the lowest point of the ischiatic bone, the greater trochanter, the lesser trochanter, the acetabulum, the saddle points, the acetabular roof, the obturator foramen, the symphysis, the sacrum, the sacrococcygeal joint, and the femoral shaft. Further, in addition to key points, the system may further utilize lines between any two key points described herein. In some embodiments, lines between corresponding features on opposing sides of the pelvis may be utilized, such as a line between femoral heads, an inter-ischial line, an inter-trochanteric line, or a teardrop line. For further types of joints, different key points and lines may be of interest for landmarking, as would be known to one having ordinary skill in the art. Additionally, different calculations may be performed for different types of joints. For example, in the case of a hip joint as seen in FIG. 28B, calculations may include pelvic tilt, deformity, and femoral displacement, among other measurements depicted by lines upon the X-ray images.

Computer readable program instructions for carrying out operations disclosed herein may include assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a LAN or WAN, or the connection may be made to an external computer (for example, through the Internet using an Internet Service Provider).

Aspects of the present invention are described herein with reference to flowchart illustrations and/or block diagrams of methods, apparatuses (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which are executed on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 29:
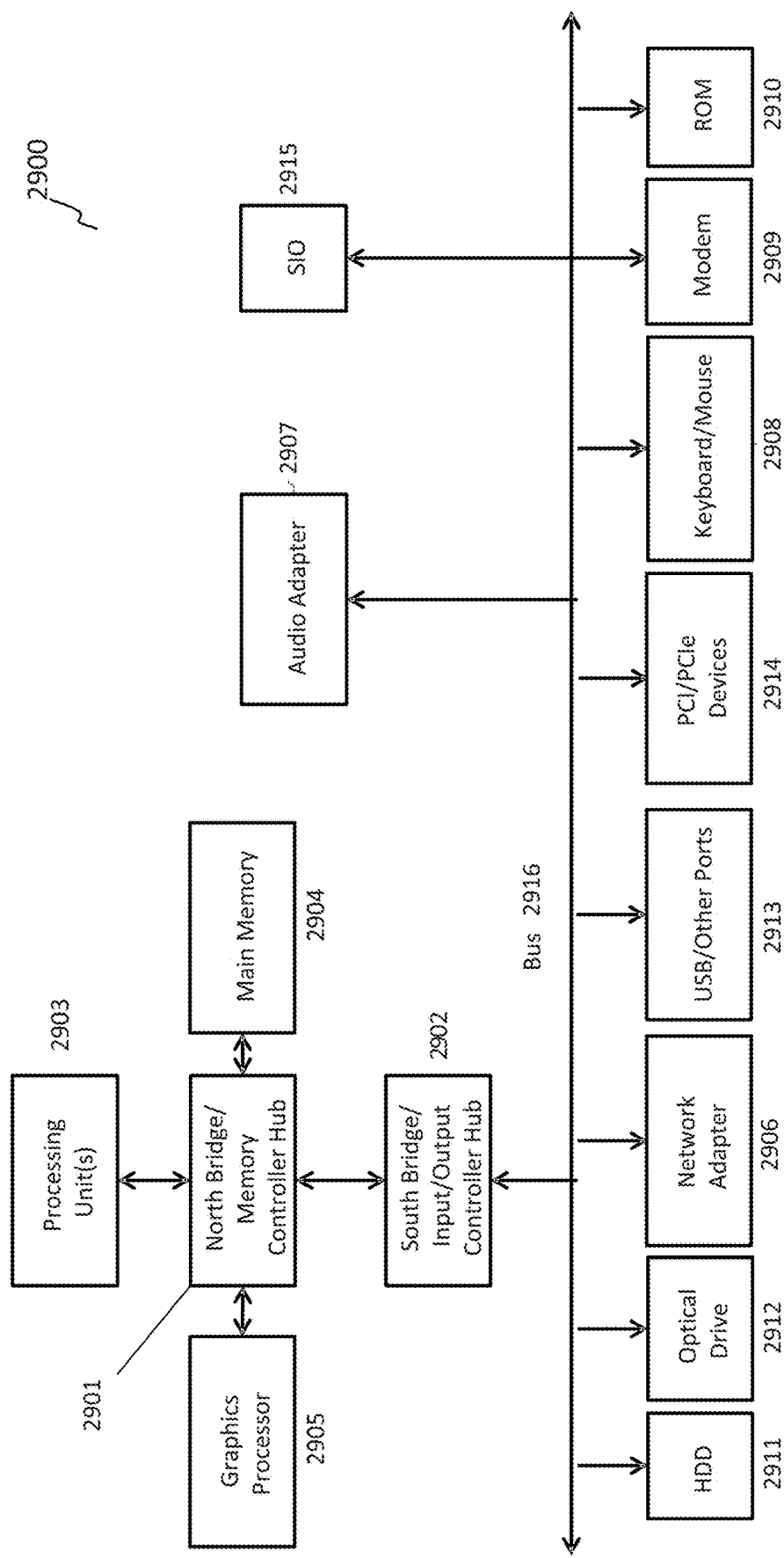
FIG. 29 illustrates a block diagram of an illustrative data processing system in which aspects of the illustrative embodiments are implemented.

FIG. 29 illustrates a block diagram of an illustrative data processing system 2900 in which aspects of the illustrative embodiments are implemented. The data processing system 2900 is an example of a computer, such as a server or client, in which computer usable code or instructions implementing the process for illustrative embodiments of the present invention are located. In some embodiments, the data processing system 2900 may be a server computing device. For example, data processing system 2900 can be implemented in a server or another similar computing device operably connected to a surgical system 100 as described above. The data processing system 2900 can be configured to, for example, transmit and receive information related to a patient and/or a related surgical plan with the surgical system 100.

In the depicted example, data processing system 2900 can employ a hub architecture including a north bridge and memory controller hub (NB/MCH) 2901 and south bridge and input/output (I/O) controller hub (SB/ICH) 2902. Processing unit 2903, main memory 2904, and graphics processor 2905 can be connected to the NB/MCH 2901. Graphics processor 2905 can be connected to the NB/MCH 2901 through, for example, an accelerated graphics port (AGP).

In the depicted example, a network adapter 2906 connects to the SB/ICH 2902. An audio adapter 2907, keyboard and mouse adapter 2908, modem 2909, read only memory (ROM) 2910, hard disk drive (HDD) 2911, optical drive (e.g., CD or DVD) 2912, universal serial bus (USB) ports and other communication ports 2913, and PCI/PCIe devices 2914 may connect to the SB/ICH 2902 through bus system 2916. PCI/PCIe devices 2914 may include Ethernet adapters, add-in cards, and PC cards for notebook computers. ROM 2910 may be, for example, a flash basic input/output system (BIOS). The HDD 2911 and optical drive 2912 can use an integrated drive electronics (IDE) or serial advanced technology attachment (SATA) interface. A super I/O (SIO) device 2915 can be connected to the SB/ICH 2902.

An operating system can run on the processing unit 2903. The operating system can coordinate and provide control of various components within the data processing system 2900. As a client, the operating system can be a commercially available operating system. An object-oriented programming system, such as the Java™ programming system, may run in conjunction with the operating system and provide calls to the operating system from the object-oriented programs or applications executing on the data processing system 2900. As a server, the data processing system 2900 can be an IBM® eServer™ System® running the Advanced Interactive Executive operating system or the Linux operating system. The data processing system 2900 can be a symmetric multiprocessor (SMP) system that can include a plurality of processors in the processing unit 2903. Alternatively, a single processor system may be employed.

Instructions for the operating system, the object-oriented programming system, and applications or programs are located on storage devices, such as the HDD 2911, and are loaded into the main memory 2904 for execution by the processing unit 2903. The processes for embodiments described herein can be performed by the processing unit 2903 using computer usable program code, which can be located in a memory such as, for example, main memory 2904, ROM 2910, or in one or more peripheral devices.

A bus system 2916 can be comprised of one or more busses. The bus system 2916 can be implemented using any type of communication fabric or architecture that can provide for a transfer of data between different components or devices attached to the fabric or architecture. A communication unit such as the modem 2909 or the network adapter 2906 can include one or more devices that can be used to transmit and receive data.

Those of ordinary skill in the art will appreciate that the hardware depicted in FIG. 29 may vary depending on the implementation. Other internal hardware or peripheral devices, such as flash memory, equivalent non-volatile memory, or optical disk drives may be used in addition to or in place of the hardware depicted. Moreover, the data processing system 2900 can take the form of any of a number of different data processing systems, including but not limited to, client computing devices, server computing devices, tablet computers, laptop computers, telephone or other communication devices, personal digital assistants, and the like. Essentially, data processing system 2900 can be any known or later developed data processing system without architectural limitation While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., +10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of generating a custom three-dimensional model of a bone, the method comprising:
    obtaining at least one 2D image of the bone;
    aligning an orientation and scale of the at least one 2D image to a pre-determined coordinate system;
    identifying, based on the at least one 2D image, a first representative bone from a library of historical bones, each of the historical bones in the library being aligned to the pre-determined coordinate system;
    selecting, based on the at least one 2D image, an ideal view of a first 3D model of the first representative bone; and
    performing one or more modifications to the first 3D model to generate the custom three-dimensional model of the bone, wherein performing each modification comprises:
        receiving user input related to a relocation of a first surface point set of the first 3D model,
        identifying, based on the at least one 2D image and the relocation, a second representative bone from the library of historical bones, and
        replacing a first fragment of the first 3D model including the first surface point set with a second fragment of a second 3D model of the second representative bone, wherein the second fragment comprises a second surface point set corresponding to the relocation.

2. The method of claim 1, wherein the first surface point set comprises at least one of a point on a surface of the first 3D model, a curve on the surface of the first 3D model, a line on surface of the first 3D model, a control point associated with a subdivided segment of the first 3D model, a key point associated with the first 3D model, and a landmark associated with the first 3D model.

3. The method of claim 1, wherein aligning an orientation and scale of the at least one 2D image comprises one or more iterations, each iteration comprising:
    modifying the orientation and scale of the at least one 2D image to align the at least one 2D image with a bone template; and
    selecting, based on the modified at least one 2D image, a potential representative bone from the library.

4. The method of claim 3, wherein the potential representative bone is the bone template for a subsequent iteration.

5. The method of claim 3, wherein the first representative bone is the potential representative bone of one of the one or more iterations.

6. The method of claim 1, wherein identifying a first representative bone comprises:
identifying, based on the at least one 2D image, a plurality of potential representative bones from the library of representative bones; and
selecting the first representative bone from the plurality of potential representative bones.

7. The method of claim 1, further comprising identifying one or more key points on the at least one 2D image.

8. The method of claim 7, wherein identifying a first representative bone is further based on the one or more key points.

9. The method of claim 7, wherein each of the one or more key points corresponds to at least one of a portion of a bony anatomy, a location of ligament attachment, a bony landmark, an anatomic landmark, a positional extreme, a knee center, a posterior point on a condyle, an anterior notch point, an epicondyle, a point on a femoral AP axis, a mid plane, an intersection point, an expected resection location, an expected position for placement of a surgical tool, a mechanical axis, and an anatomical axis.

10. The method of claim 1, wherein selecting an ideal view comprises:
comparing one or more views of the first 3D model of the first representative bone to the at least one 2D image, each of the one or more views comprising a rotation angle and a caudal angle; and
selecting, based on the at least one 2D image, an ideal view of the first representative bone from the one or more views.

11. The method of claim 10, wherein comparing one or more views comprises adjusting at least one of a rotation angle and a caudal angle of the one or more views,
wherein the custom three-dimensional model is based on the ideal view.

12. The method of claim 1, wherein receiving user input related to a relocation comprises:
presenting, via a graphical user interface, one or more locations for the first surface point set, wherein each location is associated with a corresponding surface point set of an additional 3D model in the library; and
receiving, via an input device, a selected new location from the one or more locations, wherein the second surface point set comprises the corresponding surface point set of the selected new location.

13. The method of claim 12, wherein receiving user input related to a relocation further comprises:
receiving, via the input device, a potential location from the one or more locations; and
displaying, via the graphical user interface, a corresponding fragment of the additional 3D model corresponding to the potential location superimposed over the first 3D model,
wherein receiving the selected new location comprises confirming the potential location as the selected new location.

14. A system for generating a custom three-dimensional model of a bone, the system comprising:
an input device;
a processor; and
a non-transitory, processor-readable storage medium that stores instructions executable by the processor to:
obtain at least one 2D image of the bone,
align an orientation and scale of the at least one 2D image to a pre-determined coordinate system,
identify, based on the at least one 2D image, a first representative bone from a library of historical bones, each of the historical bones in the library being aligned to the pre-determined coordinate system,
select, based on the at least one 2D image, an ideal view of a first 3D model of the first representative bone, and
perform one or more modifications to the first 3D model to generate the custom three-dimensional model of the bone, wherein performing each modification comprises:
receiving user input related to a relocation of a first surface point set of the first 3D model via the input device,
identifying, based on the at least one 2D image and the relocation, a second representative bone from the library of historical bones, and
replacing a first fragment of the first 3D model including the first surface point set with a second fragment of a second 3D model of the second representative bone, wherein the second fragment comprises a second surface point set corresponding to the relocation.

15. The system of claim 14, wherein the first surface point set comprises at least one of a point on a surface of the first 3D model, a curve on the surface of the first 3D model, a line on surface of the first 3D model, a control point associated with a subdivided segment of the first 3D model, a key point associated with the first 3D model, and a landmark associated with the first 3D model.

16. The system of claim 14, wherein the instructions are executable by the processor to complete one or more iterations, each iteration comprising:
modifying the orientation and scale of the at least one 2D image to align the at least one 2D image with a bone template; and
selecting, based on the modified at least one 2D image, a potential representative bone from the library.

17. The system of claim 16, wherein the potential representative bone is the bone template for a subsequent iteration.

18. The system of claim 16, wherein the first representative bone is the potential representative bone of one of the one or more iterations.

19. The system of claim 14, wherein the instructions are executable by the processor to:
identify, based on the at least one 2D image, a plurality of potential representative bones from the library of representative bones; and
select the first representative bone from the plurality of potential representative bones.

20. The system of claim 14, wherein the instructions are further executable by the processor to identify one or more key points on the at least one 2D image.

21. The system of claim 20, wherein the instructions executable by the processor to identify the first representative bone based on the one or more key points.

22. The system of claim 20, wherein each of the one or more key points corresponds to at least one of a portion of a bony anatomy, a location of ligament attachment, a bony landmark, an anatomic landmark, a positional extreme, a knee center, a posterior point on a condyle, an anterior notch point, an epicondyle, a point on a femoral AP axis, a mid plane, an intersection point, an expected resection location, an expected position for placement of a surgical tool, a mechanical axis, and an anatomical axis.

23. The system of claim 14, wherein the instructions are executable by the processor to:
compare one or more views of the first 3D model of the first representative bone to the at least one 2D image, each of the one or more views comprising a rotation angle and a caudal angle; and
select, based on the at least one 2D image, an ideal view of the first representative bone from the one or more views.

24. The system of claim 23, wherein the instructions are executable by the processor to adjust at least one of a rotation angle and a caudal angle of the one or more views, wherein the custom three-dimensional model is based on the ideal view.

25. The system of claim 14, wherein receiving user input related to a relocation comprises:
presenting, via a graphical user interface, one or more locations for the first surface point set, wherein each location is associated with a corresponding surface point set of an additional 3D model in the library; and
receiving, via the input device, a selected new location from the one or more locations, wherein the second surface point set comprises the corresponding surface point set of the selected new location.

26. The system of claim 25, wherein receiving user input related to a relocation further comprises:
receiving, via the input device, a potential location from the one or more locations; and
displaying, via the graphical user interface, a corresponding fragment of the additional 3D model corresponding to the potential location superimposed over the first 3D model,
wherein receiving the selected new location comprises confirming the potential location as the selected new location.

* * * * *